US 10,045,780 B2

(12) United States Patent
Adams et al.

(10) Patent No.: US 10,045,780 B2
(45) Date of Patent: Aug. 14, 2018

(54) METHOD OF APPLYING STAPLES IN LOWER ANTERIOR BOWEL RESECTION

(71) Applicant: Ethicon Endo-Surgery, LLC, Guaynabo, PR (US)

(72) Inventors: Thomas Adams, Cincinnati, OH (US); Hector Chow, Cincinnati, OH (US); Steven Dickinson, Cincinnati, OH (US); Douglas B. Hoffman, Cincinnati, OH (US); Barry T. Jamison, Fairfield, OH (US); John S. Kimsey, Hebron, KY (US); Disha V. Labhasetwar, Cincinnati, OH (US); Anil K. Nalagatla, Mason, OH (US); Sudhir Patel, Cincinnati, OH (US); Mary R. Towers, West Chester, OH (US)

(73) Assignee: Ethicon LLC, Gyaynabo, PR (US)

( * ) Notice: Subject to any disclaimer, the term of this patent is extended or adjusted under 35 U.S.C. 154(b) by 274 days.

(21) Appl. No.: 14/985,578

(22) Filed: Dec. 31, 2015

(65) Prior Publication Data
US 2017/0189022 A1    Jul. 6, 2017

(51) Int. Cl.
*A61B 17/072*    (2006.01)
*A61B 17/00*    (2006.01)

(52) U.S. Cl.
CPC ...... *A61B 17/072* (2013.01); *A61B 17/00234* (2013.01); *A61B 2017/00743* (2013.01); *A61B 2017/07221* (2013.01); *A61B 2017/07257* (2013.01); *A61B 2017/07278* (2013.01); *A61B 2017/07285* (2013.01)

(58) Field of Classification Search
CPC ............ A61B 17/072; A61B 17/00234; A61B 2017/07257; A61B 2017/07221; A61B 2017/00743; A61B 2017/07278; A61B 2017/07285
See application file for complete search history.

(56) References Cited

U.S. PATENT DOCUMENTS

| 3,795,034 A | * | 3/1974 | Strekopytov | ........ A61B 17/072 227/178.1 |
| 5,403,312 A | | 4/1995 | Yates et al. | |
| 6,817,508 B1 | * | 11/2004 | Racenet | ............... A61B 17/072 227/175.2 |

(Continued)

OTHER PUBLICATIONS

U.S. Appl. No. 12/031,573, filed Feb. 14, 2008.
U.S. Appl. No. 14/813,242, filed Jul. 30, 2015.

*Primary Examiner* — Julian W Woo
(74) *Attorney, Agent, or Firm* — Frost Brown Todd LLC

(57) ABSTRACT

A method for manipulating tissue of a patient includes a surgical instrument having a handle assembly, a shaft assembly, and an end effector. The method includes positioning a tissue within a gap between a cartridge and an anvil and against a guide pin to laterally position the tissue relative to the cartridge and the anvil. The method also includes moving a retaining pin from an open position to a closed position to capture the tissue and moving the cartridge toward the anvil in a closed configuration. Furthermore, the method includes inhibiting deflection of a distal end portion of the end effector wherein at least at least one of the guide pin or the retaining pin connects to the distal end portion. The method further includes forming a plurality of staples within the tissue and cutting the tissue with a knife.

20 Claims, 60 Drawing Sheets

(56) References Cited

U.S. PATENT DOCUMENTS

| | | |
|---|---|---|
| 6,988,650 B2 | 1/2006 | Schwemberger et al. |
| 7,000,818 B2 | 2/2006 | Shelton et al. |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,422,139 B2 | 9/2008 | Shelton et al. |
| 7,464,849 B2 | 12/2008 | Shelton et al. |
| 7,670,334 B2 | 3/2010 | Hueil et al. |
| 7,753,245 B2 | 7/2010 | Boudreaux et al. |
| 7,845,537 B2 | 12/2010 | Shelton et al. |
| 7,980,443 B2 | 7/2011 | Scheib et al. |
| 8,210,411 B2 | 7/2012 | Yates et al. |
| 8,308,040 B2 | 11/2012 | Huang et al. |
| 8,220,688 B2 | 12/2012 | Laurent et al. |
| 8,353,436 B2 * | 1/2013 | Kasvikis .............. A61B 17/072 227/175.1 |
| 8,393,514 B2 | 3/2013 | Shelton et al. |
| 8,561,870 B2 | 10/2013 | Baxter et al. |
| 8,608,045 B2 | 12/2013 | Smith et al. |
| 8,733,613 B2 | 5/2014 | Huitema et al. |
| 9,072,535 B2 | 7/2015 | Shelton et al. |
| 9,101,358 B2 | 8/2015 | Kerr et al. |
| 9,198,658 B2 | 12/2015 | Kasvikis |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2007/0175955 A1 | 8/2007 | Shelton et al. |
| 2014/0263551 A1 | 9/2014 | Hall et al. |
| 2014/0263552 A1 | 9/2014 | Hall et al. |
| 2016/0242767 A1 * | 8/2016 | Kasvikis .............. A61B 17/072 |

* cited by examiner

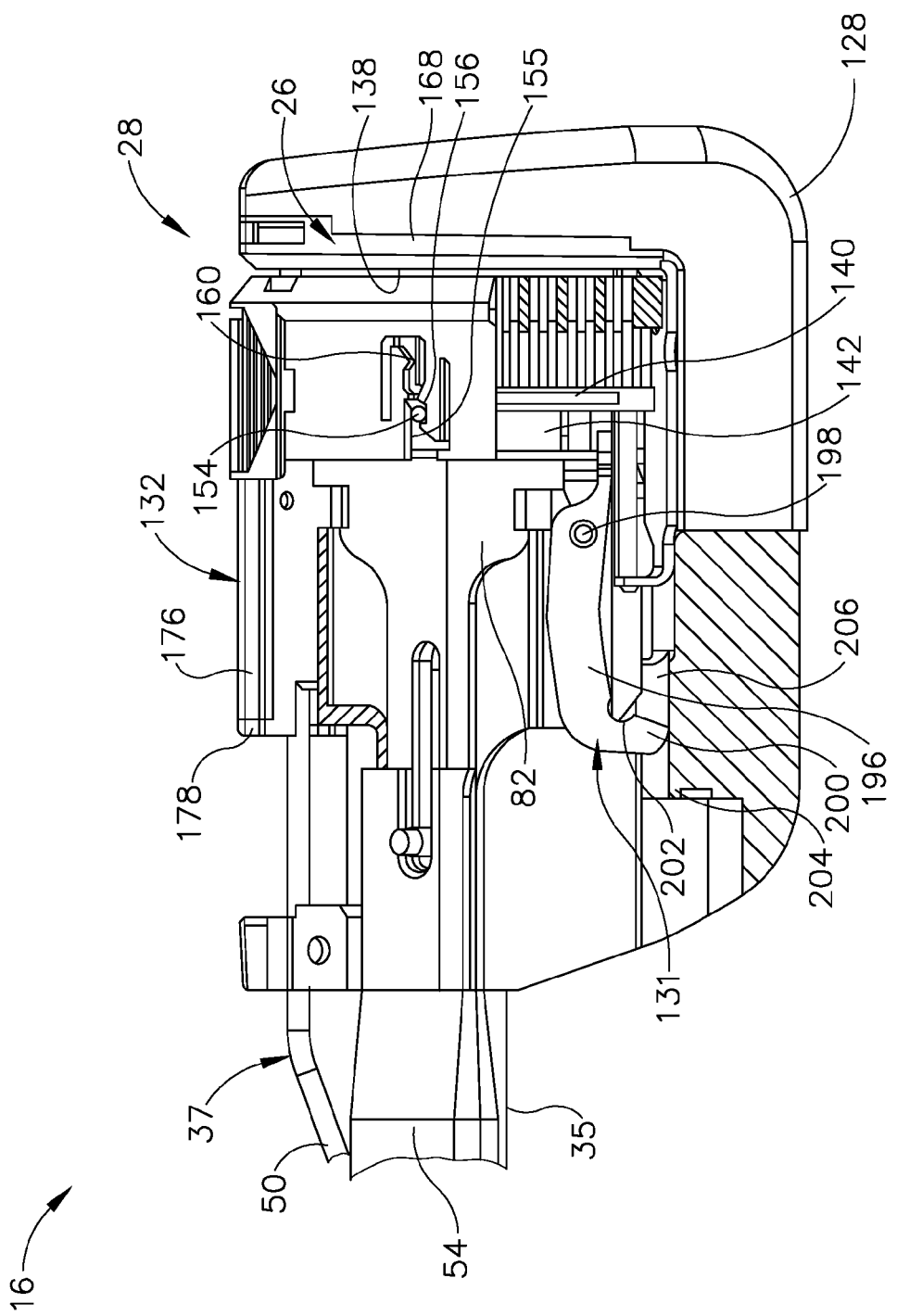

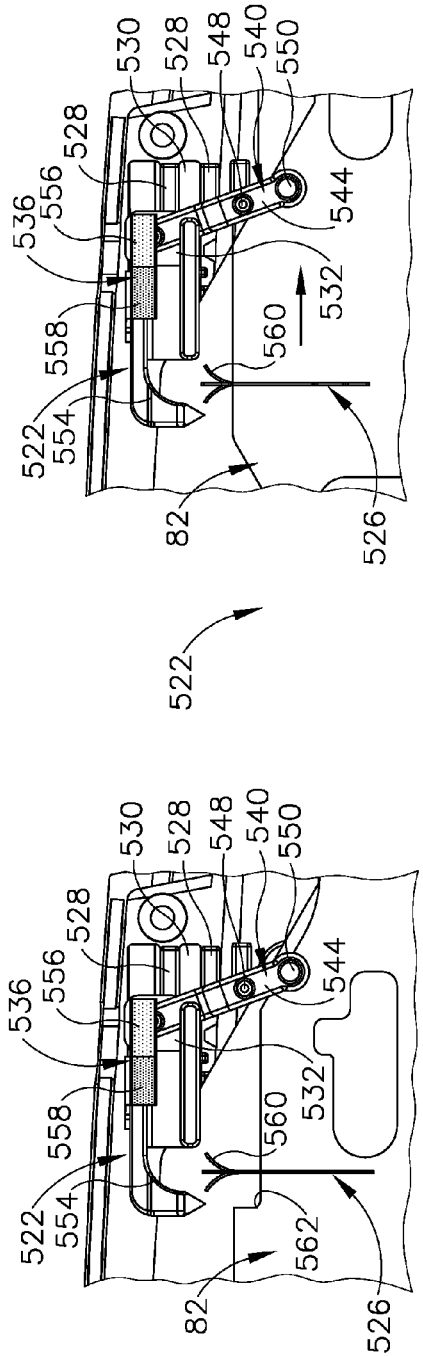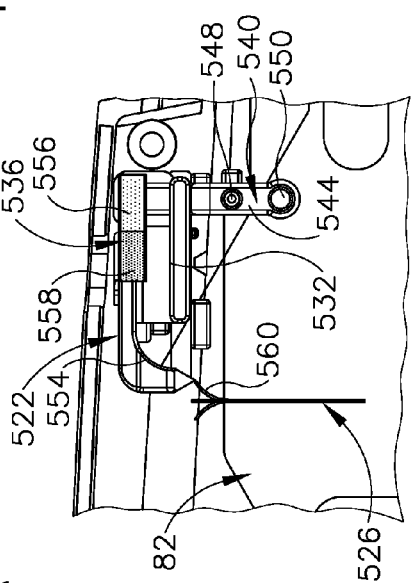

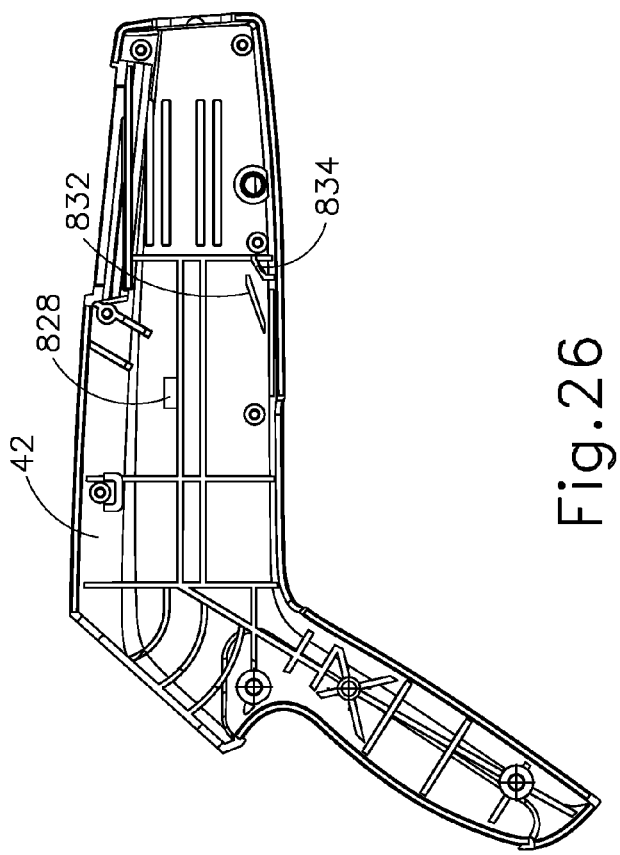
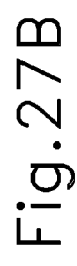
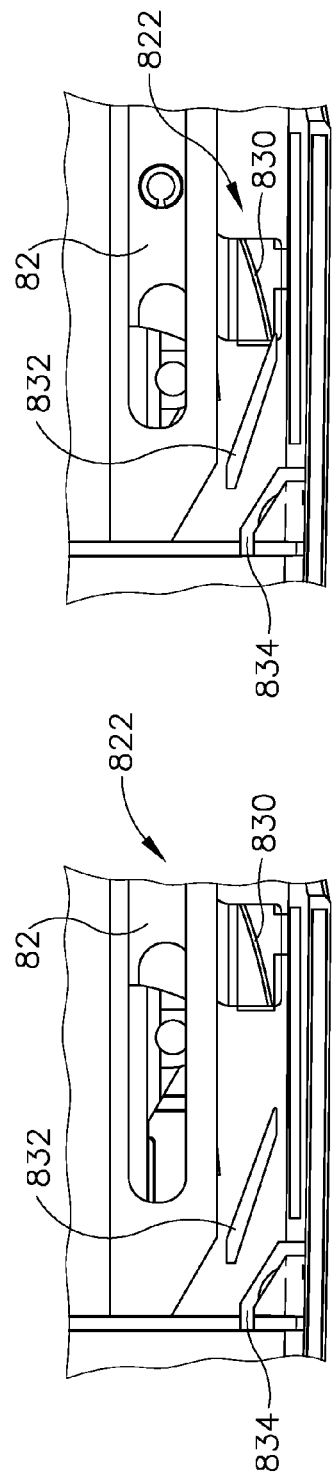

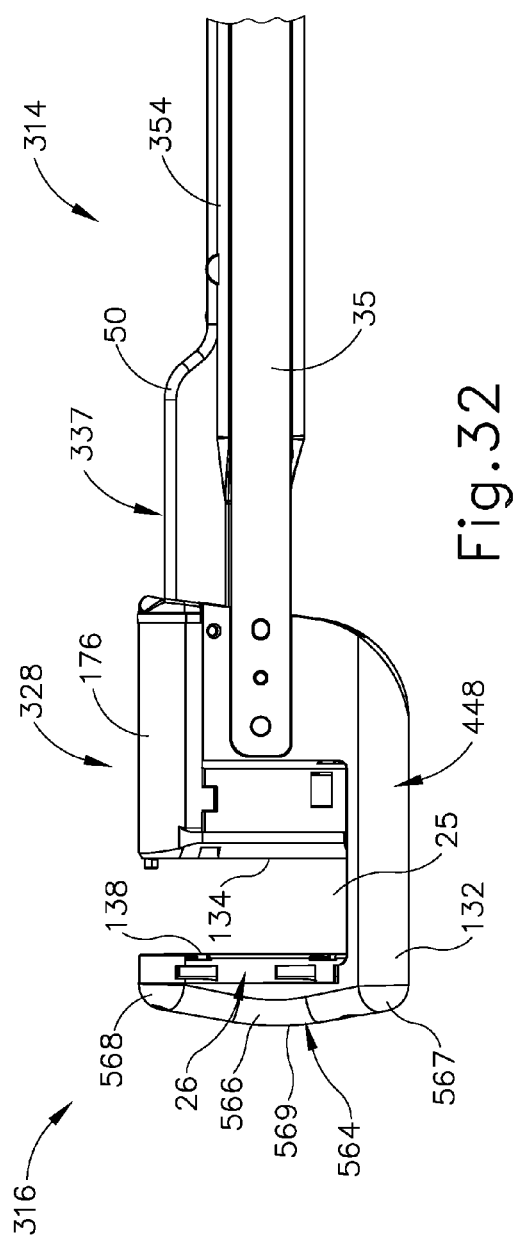
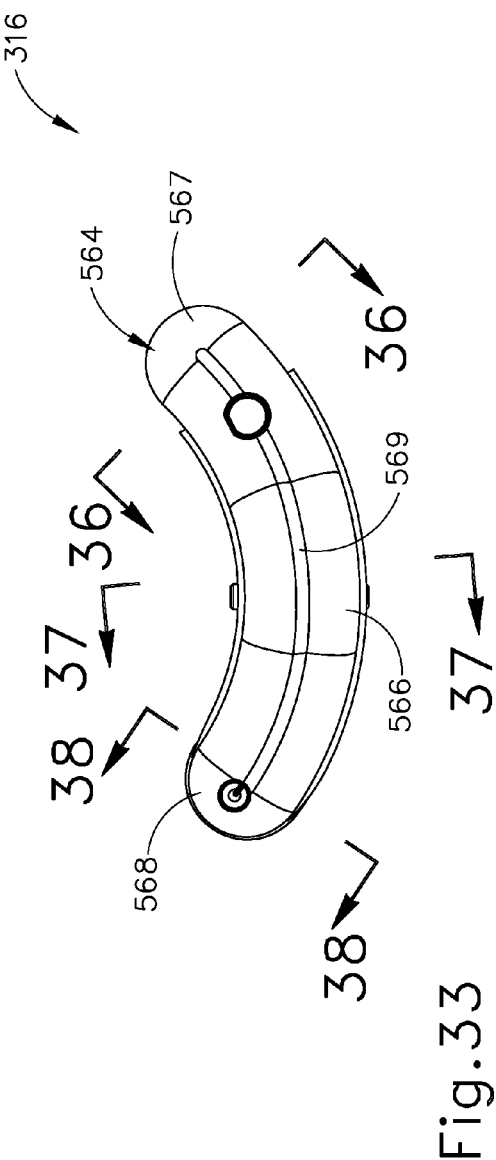
Fig.32
Fig.33

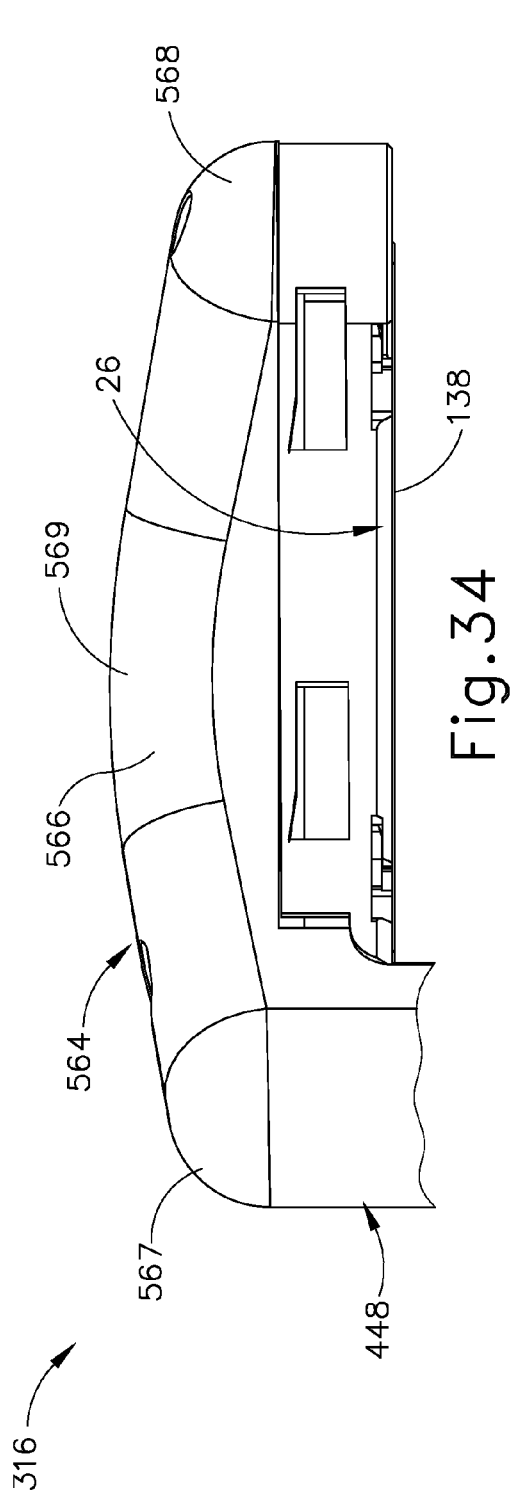
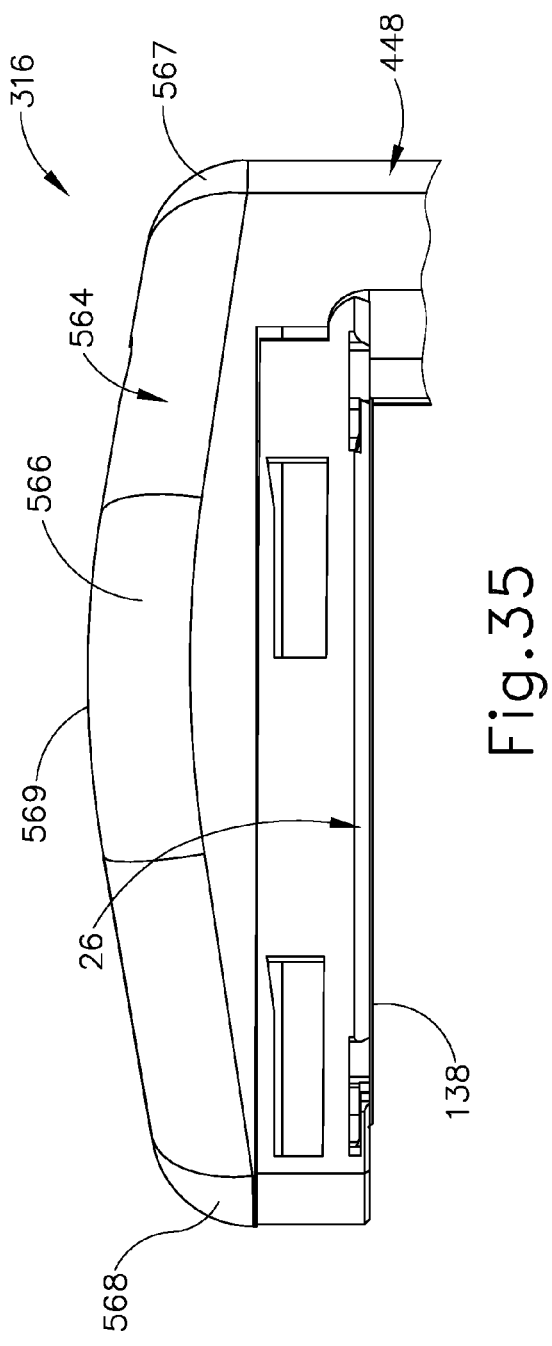

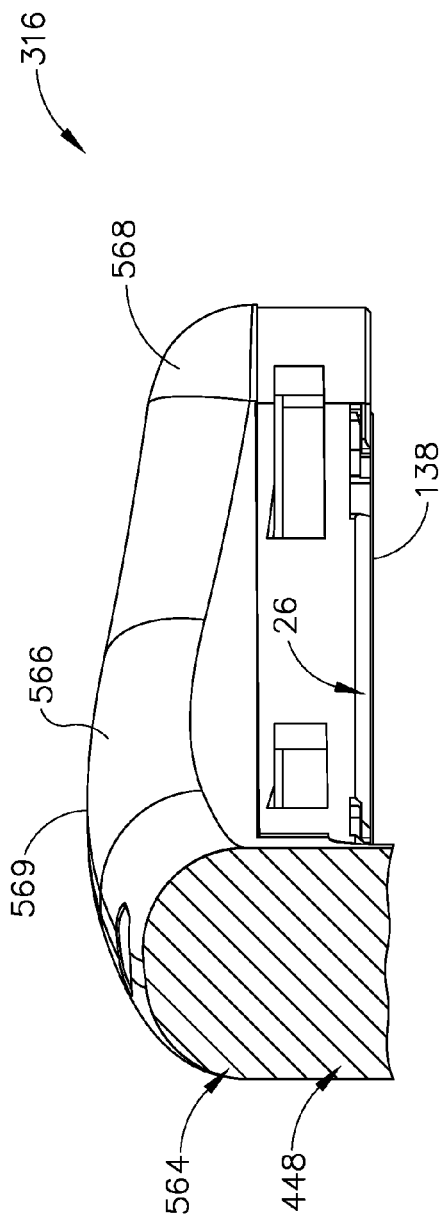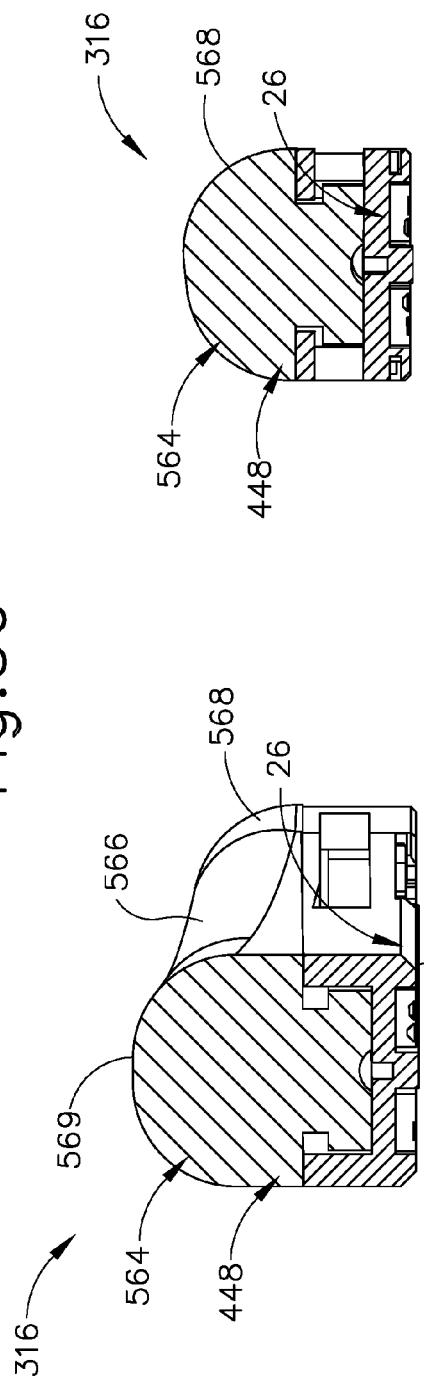

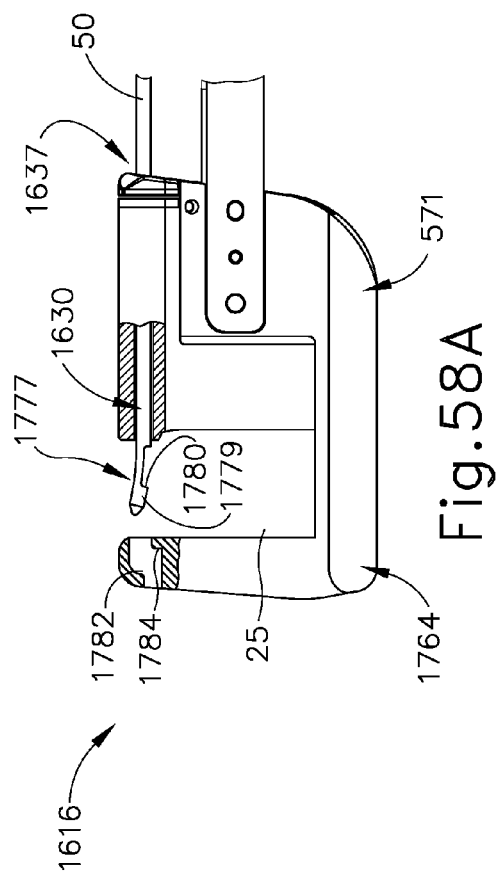
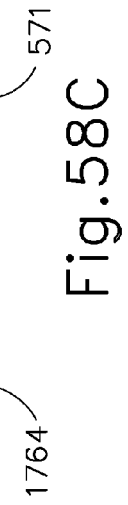
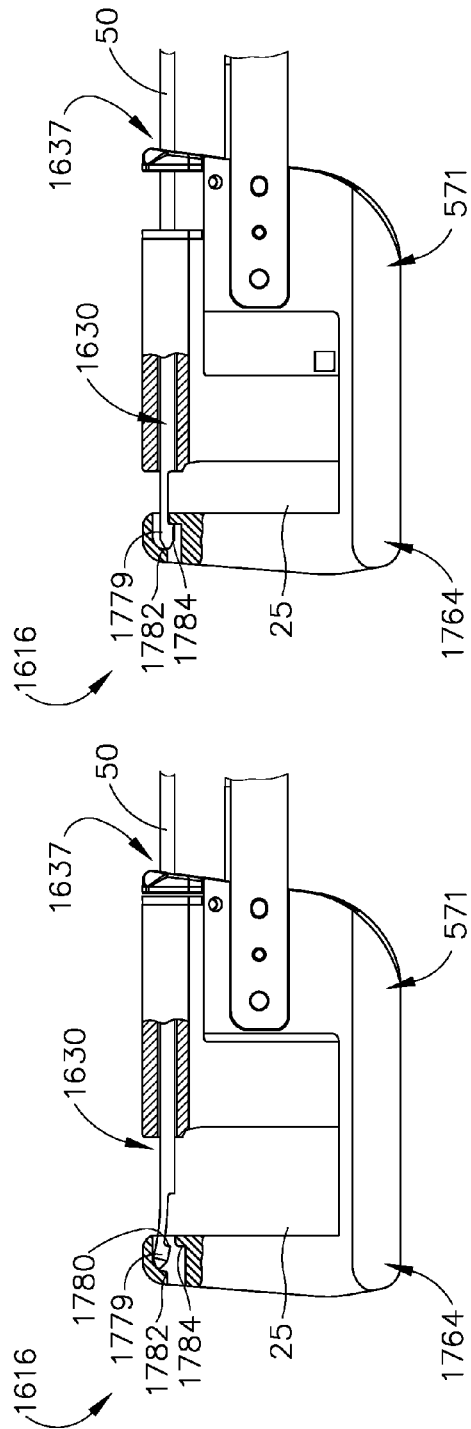

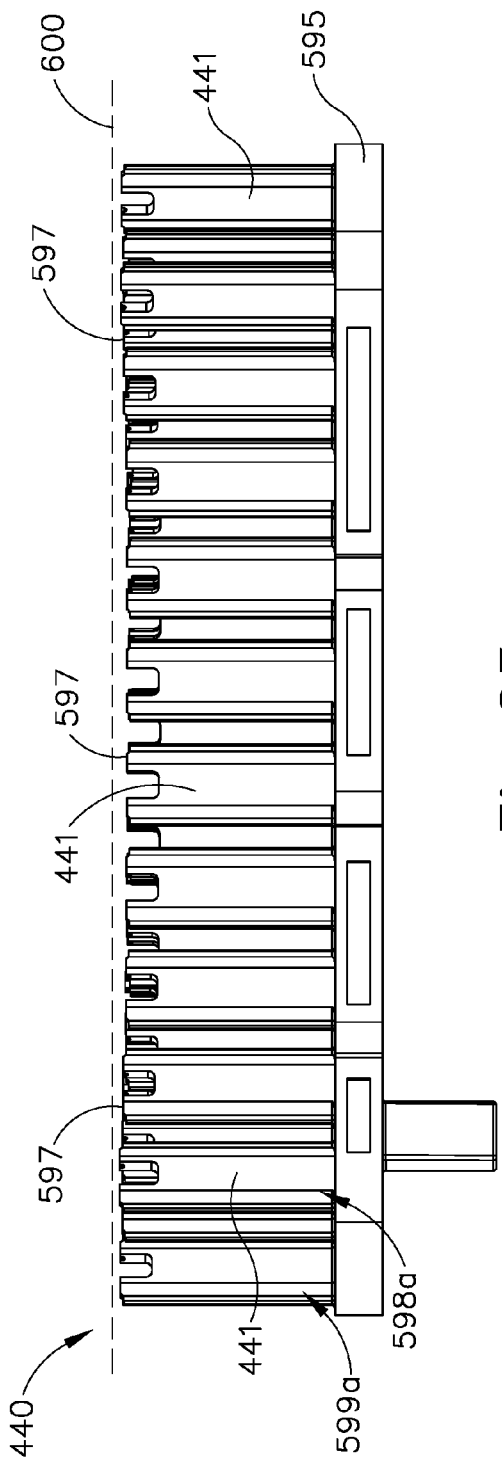
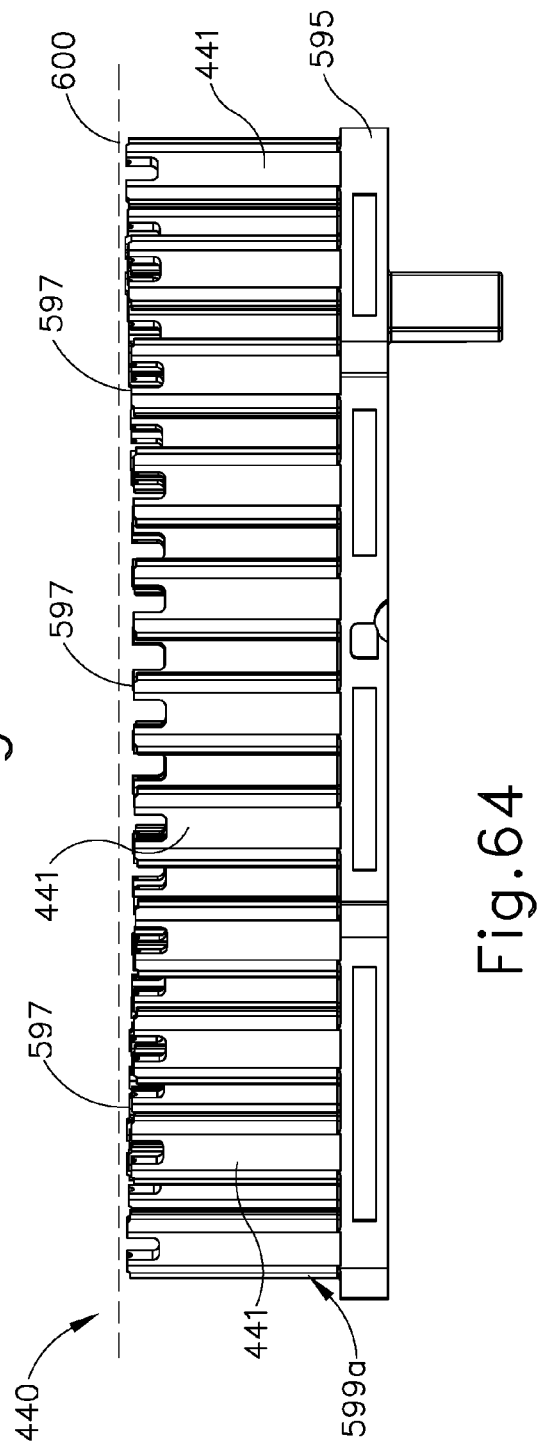

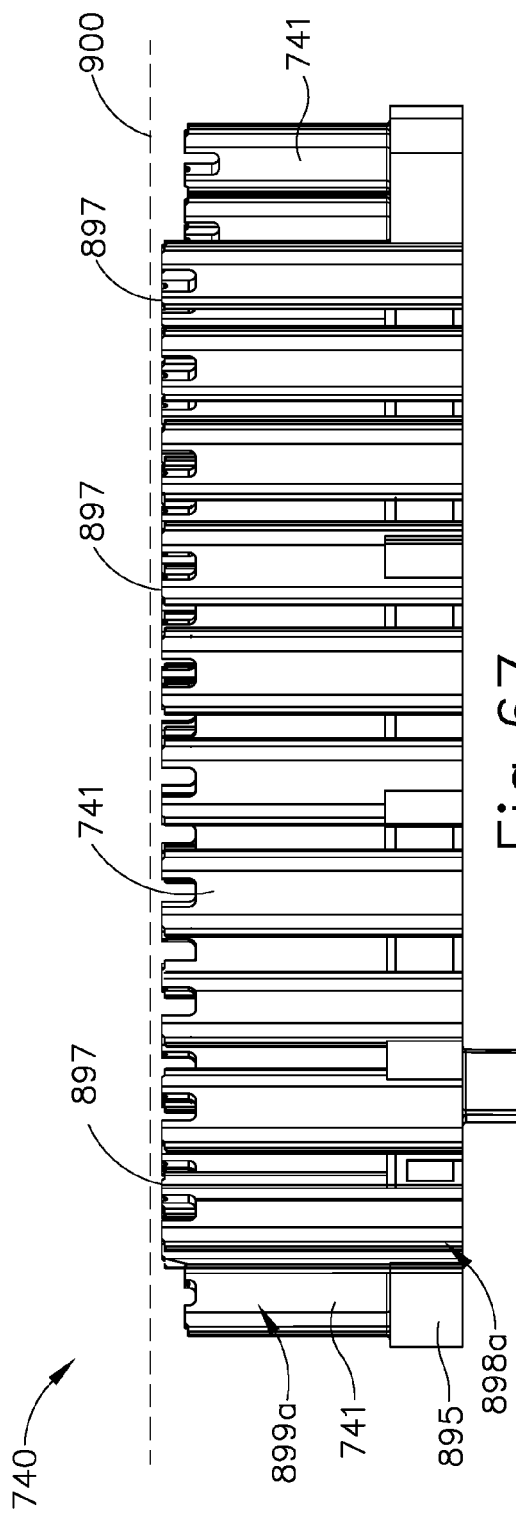
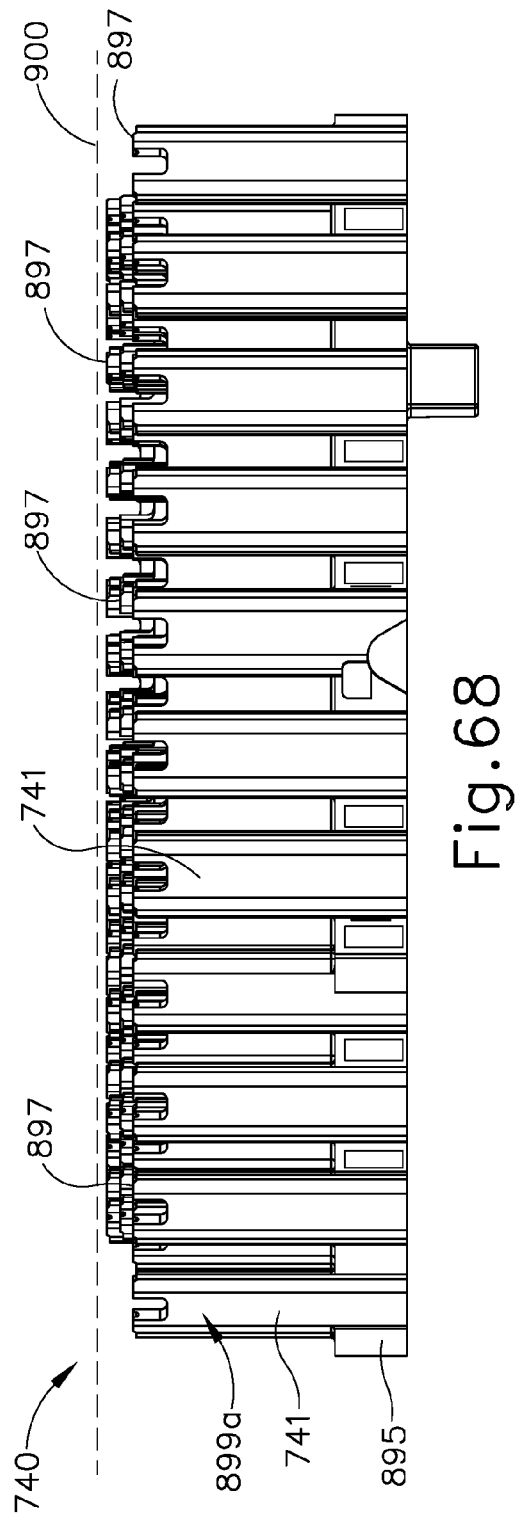

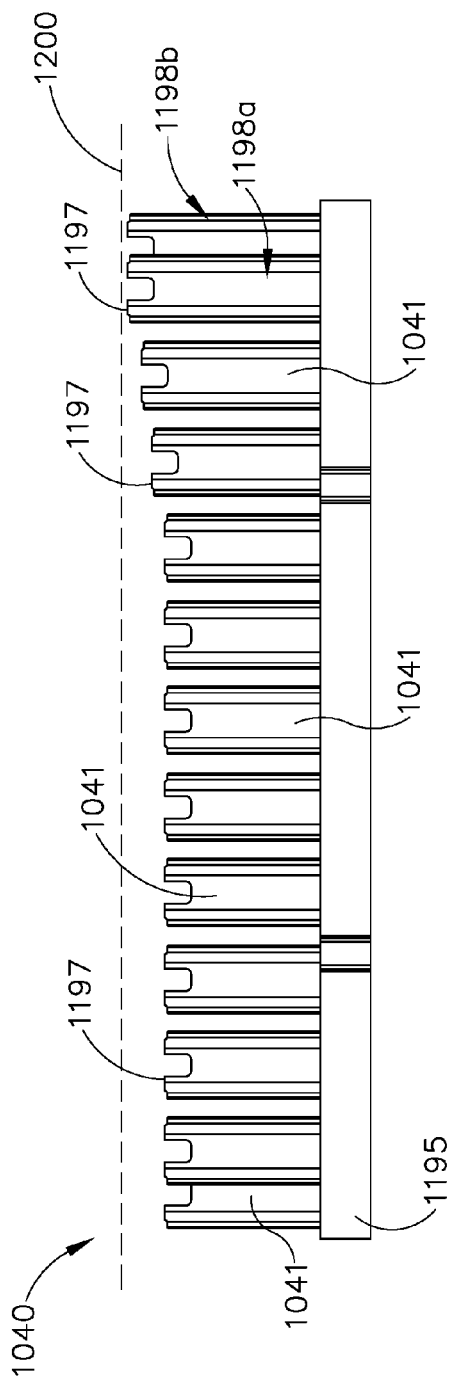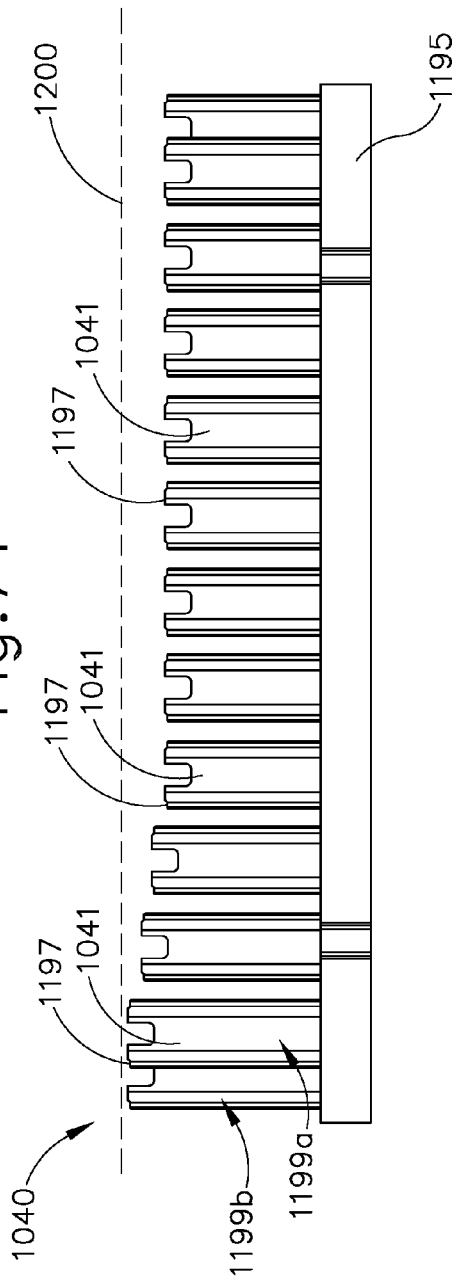

METHOD OF APPLYING STAPLES IN LOWER ANTERIOR BOWEL RESECTION

BACKGROUND

Some surgical staplers are operable to clamp down on one or more layers of patient tissue, form staples through the layers of tissue to substantially seal the layers of tissue together near the formed staples, and cut through the layers of tissue for forming severed ends of operatively sealed tissue. An exemplary stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely exemplary surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 4, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. Patents is incorporated by reference herein. Additional merely exemplary surgical staplers are disclosed in U.S. Pat. Pub. No. 2005/0139636, entitled "Replaceable Cartridge Module for a Surgical Stapling and Cutting Instrument," published on Jun. 30, 2005; U.S. Pat. Pub. No. 2005/0143759, entitled "Curved Cutter Stapler Shaped for Male Pelvis," published on Jun. 30, 2005; and U.S. Pat. Pub. No. 2005/0145672, entitled "Curved Cutter Stapler with Aligned Tissue Retention Feature," published on Jul. 7, 2005. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAR") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7C depicts a left side view of the end effector of FIG. 1A with various components removed for clarity, and with the pin actuation mechanism in the closed position and the staple cartridge in the closed position via actuation of the closure mechanism;

FIG. 23A depicts an enlarged left side view of the handle assembly of FIG. 17, with the translational feedback generator in an unfired position;

FIG. 23B depicts an enlarged left side view of the handle assembly of FIG. 17, with a firing bar moving from the unfired position toward a fired position;

FIG. 23C depicts an enlarged left side view of the handle assembly of FIG. 17, with the translational feedback generator in a fired position;

FIG. 26 depicts a left side view of a left shroud portion of the handle assembly of FIG. 25;

FIG. 27A depicts an enlarged right side view of the audible feedback generator of the handle assembly of FIG. 25, with various components removed for clarity, and with the audible feedback generator in an unfired position;

FIG. 27B depicts an enlarged right side view of the audible feedback generator of the handle assembly of FIG. 25, with various components removed for clarity, and with the audible feedback generator moving toward the fired position;

FIG. 32 depicts a right side view of another exemplary end effector of the surgical stapling instrument of FIG. 11;

FIG. 33 depicts a front end view of the end effector of FIG. 32;

FIG. 34 depicts an enlarged right side view of the end effector of FIG. 32;

FIG. 35 depicts an enlarged left side view of the end effector of FIG. 32;

FIG. 36 depicts an enlarged cross-sectional view of the end effector of FIG. 32, taken along section line 36-36 of FIG. 33;

FIG. 37 depicts an enlarged cross-sectional view of the end effector of FIG. 32, taken along section line 37-37 of FIG. 33;

FIG. 38 depicts an enlarged cross-sectional view of the end effector of FIG. 32, taken along section line 38-38 of FIG. 33;

FIG. 58A depicts a right side sectional view of another exemplary end effector having a retaining pin in the open position, taken generally along a centerline of the retaining pin, with various components removed for clarity;

FIG. 58B depicts a right side sectional view of the end effector of FIG. 58A, with the retaining pin being moving from the open position to the unlocked closed position;

FIG. 58C depicts a right side sectional view of the end effector of FIG. 58A, with the retaining pin in a locked closed position;

FIG. 63 depicts a right side view of the staple driver assembly of FIG. 60;

FIG. 64 depicts a left side view of the staple driver assembly of FIG. 60;

FIG. 67 depicts a right side view of the staple driver assembly of FIG. 65;

FIG. 68 depicts a left side view of the staple driver assembly of FIG. 65;

FIG. 71 depicts a right side view of the staple driver assembly of FIG. 69; and

FIG. 72 depicts a left side view of the staple driver assembly of FIG. 69.

Figure 1A:
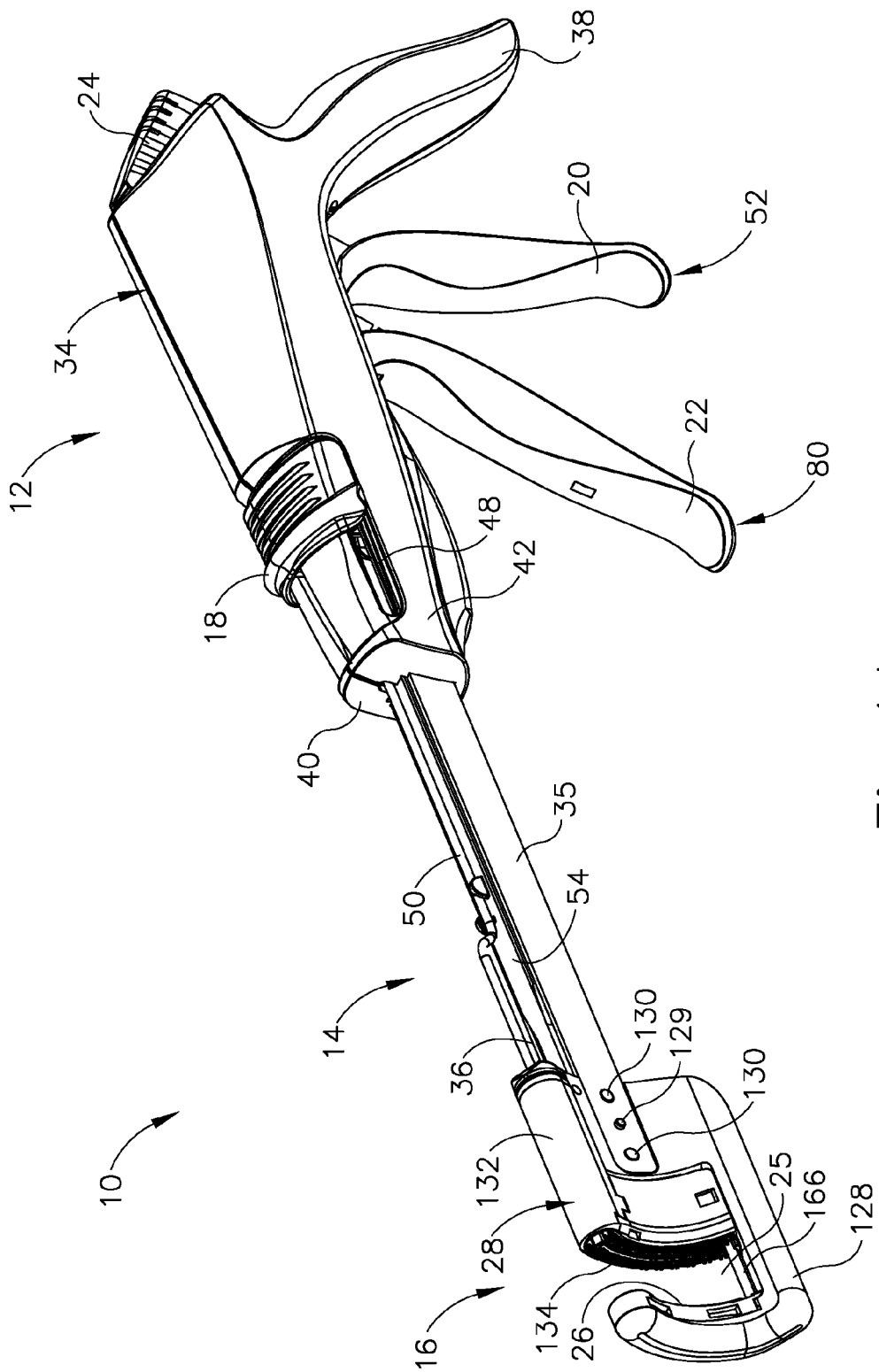
FIG. 1A depicts a right front perspective view of an exemplary surgical stapling instrument with a pin actuation mechanism in an open position and a staple cartridge in open position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

I. Exemplary Surgical Stapler

FIG. 1A depicts an exemplary surgical stapling and severing instrument (10) that includes a handle assembly (12), a shaft assembly (14), and an end effector (16) distally projecting from shaft assembly (14). It should be understood that terms such as "proximal," "distal," "right," and "left" are used herein with reference to a clinician gripping handle assembly (12) of surgical stapling instrument (10). Thus, end effector (16) is distal with respect to the relatively proximal handle assembly (14). Except as otherwise described herein, instrument (10) may be configured and operable in accordance with at least some of the teachings of U.S. Pat. Pub. No. 2005/0143759, entitled "Curved Cutter Stapler Shaped for Male Pelvis," published on Jun. 30, 2005, the disclosure of which is incorporated by reference herein; and/or U.S. Patent Application Publication No. 2017/0027571, entitled "Surgical Instrument Comprising Systems for Assuring the Proper Sequential Operation of the Surgical Instrument," published on Feb. 2, 2017, the disclosure of which is incorporated by reference herein.

Figure 1B:
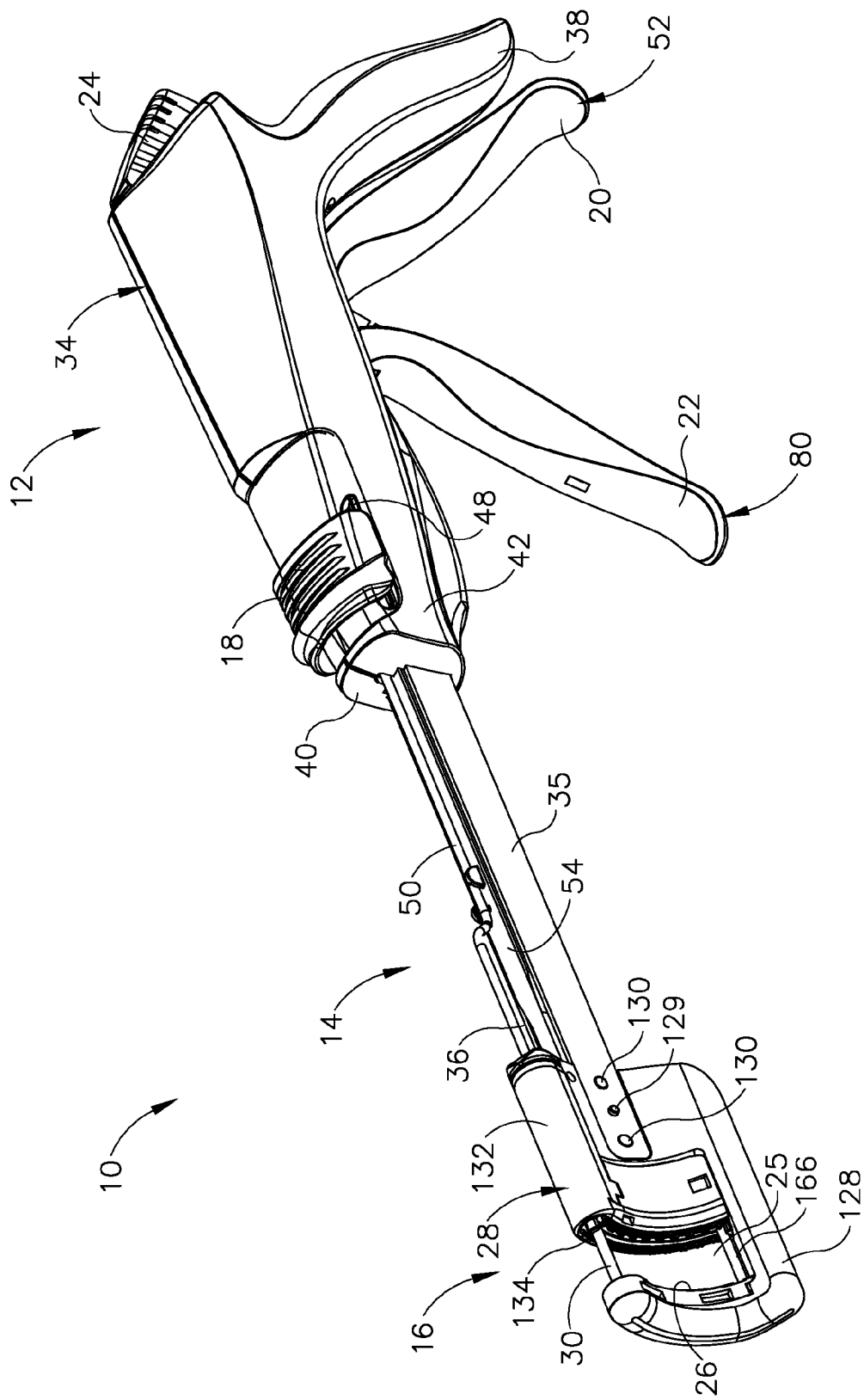
FIG. 1B depicts a right front perspective view of the surgical stapling instrument of FIG. 1A with the pin actuation mechanism in a closed position and the staple cartridge in the open position.

Handle assembly (12) includes several actuation mechanisms for operating end effector (16) during the surgical procedure. To this end, exemplary handle assembly (12) includes a saddle shaped slide (18), a closure trigger (20), and a firing trigger (22) in communication with end effector (16) via shaft assembly (14). As shown in FIG. 1A, slide (18) and closure trigger (20) are in open configurations such that end effector (16) is configured to receive tissue laterally within a gap (25) between an anvil (26) and a cartridge (28) of end effector (16). Translating slide (18) distally toward end effector (16) slides a retaining pin (30) of end effector distally as shown in FIG. 1B for capturing the tissue between anvil (26) and cartridge (28). With respect to FIGS. 1C and 1D, sequentially actuating closure trigger (20) and firing trigger (22) respectively compresses the tissue between anvil (26) and cartridge (28) in a closed configuration and then forms a plurality of staples (not shown) within the tissue and severs the tissue with a knife (32) (see FIG. 6) for treatment. Additional details regarding these exemplary actuation mechanisms will be provided below in greater detail.

A. Exemplary Handle Assembly and Shaft Assembly

Figure 2A:
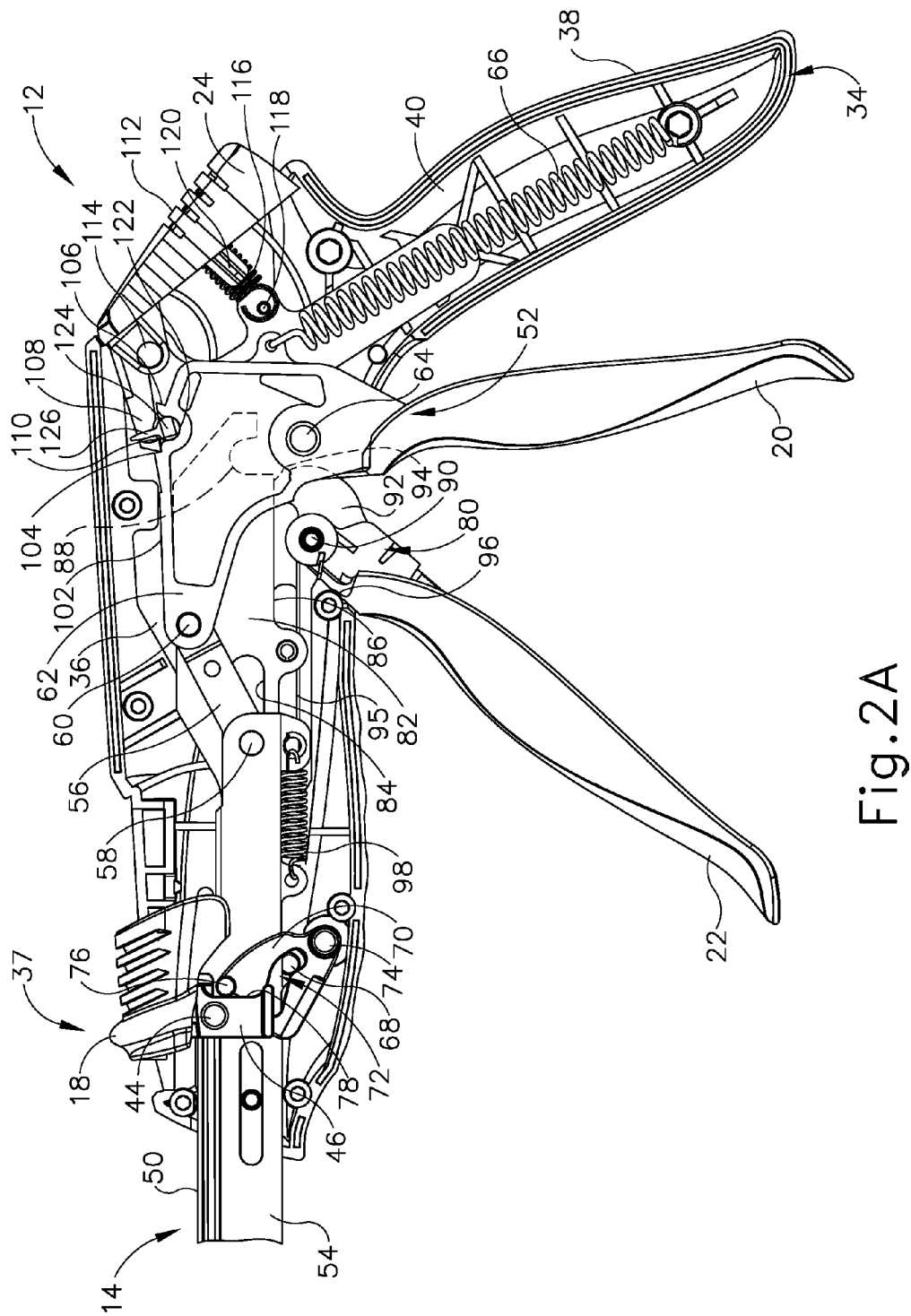
FIG. 2A depicts a right side view of a handle assembly of the surgical stapling instrument of FIG. 1A, with various components removed for clarity, and with the pin actuation mechanism in a closed position and the staple cartridge in the open position.

As shown in FIGS. 1A and 2A, handle assembly (12) has a handle housing (34), a pair of handle frame plates (35, 36) within handle housing (34) extending along shaft assembly (14), saddle shaped slide (18), closure trigger (20), and firing trigger (22) as briefly discussed above. Handle housing (34) defines a hand grip (38), which the operator, such as a surgeon, grasps with the palm of at least one hand. Handle housing (34) is formed by a right shroud handle portion (40) and a left shroud handle portion (42). Closure trigger (20) is proximally positioned relative to firing trigger (22) and each are pivotally mounted to frame plates (35, 36) to extend underneath a remainder of handle assembly (12) for manipulation by the fingers of the operator. Closure and firing triggers (20, 22) are shown in unactuated positions prior to closing end effector (16) and firing staples (not shown) and/or knife (32) (see FIG. 6). Consequently, cartridge (28) is spaced from anvil (26) for receiving tissue within gap (25) therebetween.

Surgical stapling instrument (10) captures tissue via a tissue retaining pin actuation mechanism (37) prior to actuation of the closure and firing triggers (20, 22). FIG. 1A shows retaining pin actuation mechanism (37), which includes slide (18), in the open configuration, whereas FIG. 2A shows retaining pin actuation mechanism (37) in the closed configuration in greater detail. With respect to FIG. 2A, slide (18) is mounted on an upper surface of handle housing (34) and is configured to linearly translate between proximal and distal positions. Slide (18) connects to posts (44), which extend laterally outwardly from a push rod driver (46), through slots (48) (see FIG. 1A). Push rod driver (46) is restrained within handle housing (34) along longitudinal movement by slots (48). Push rod driver (46) is connected to a proximal end of a push rod (50). A distal end of push rod (50) connects to retaining pin (30) (see FIG. 6) such that distal movement of slide (18) causes push rod (50) to similarly slide proximally along shaft assembly (14) for moving retaining pin (30) (see FIG. 6) to the closed configuration, which will be discussed below in greater detail.

A closure mechanism (52), which includes closure trigger (20), is configured to selectively move cartridge (28) toward the tissue positioned between anvil (26) and cartridge (28) in the closed configuration in anticipation of stapling and/or cutting the tissue. Closure mechanism (52) further includes an elongated closure member (54), with a generally U-shaped cross-section, extending distally from handle assembly (12), through shaft assembly (14), and into end effector (16) for receiving a cartridge (28) (see FIG. 3) at a distal end portion thereof as discussed below. A proximal end portion of closure member (54) is operatively connected to closure trigger (20) by a plurality of linkages configured to convert pivoting motion of closure trigger (20) into translation of closure member (54). More particularly, the intermediate and proximal end portions of closure member (54) extend through handle assembly (12) between left and right handle frame plates (35, 36). Right and left closure links (56) are respectively pivotally attached at the right and left proximal ends of closure member (54) by an integral closure link pin (58). At an opposite end of the closure links (56), closure links (56) are pivotally attached to another integral closure link pin (60). Closure link pin (60) connects closure links (56) to a slotted closure arm link (62), which is pivotally mounted to handle frame plates (35, 36) at a closure trigger pin (64). Closure trigger (20) descends from the slotted closure arm link (62) for pivotal rotation about closure trigger pivot pin (64) both toward and away from hand grip (38). A closure spring (66) housed within hand grip (38) is secured to the slotted closure arm link (62) to provide a desired resistance when the operator squeezes closure trigger (20) toward hand grip (38), and to bias closure trigger (20) toward the open position.

Closure member (54) is further configured for directing movement of tissue retaining pin actuation mechanism (37) to automatically direct movement of the retaining pin (30) to the closed configuration while the operator squeezes closure trigger (20). Such automation may be useful in the event that the operator did not manually move the slide (18) to the distal position before actuating trigger (20). Closure member (54) includes posts (68), which extend laterally on each opposing side of closure member (54) within handle housing (34). Posts (68) slidably connect to a yoke (70) via L-shaped slots (72). Yoke (70) is pivotally mounted within handle housing (34) by a pivot pin (74). Yoke (70) further includes cam pins (76) that are configured to push camming surfaces (78) on push rod driver (46). Thus, actuating closure trigger (20) to an intermediate position shown in FIG. 2A directs the closure member (52) distally and, in turn, causes yoke (70) to engage push rod driver (46) and force retaining pin (30) (see FIG. 1B) to the closed position. Slide (18) is thereby dragged along handle housing (34) from the proximal position to the distal position in the event that the operator did not manually manipulate slide (18) to the distal position before actuating trigger (20).

Figure 1C:
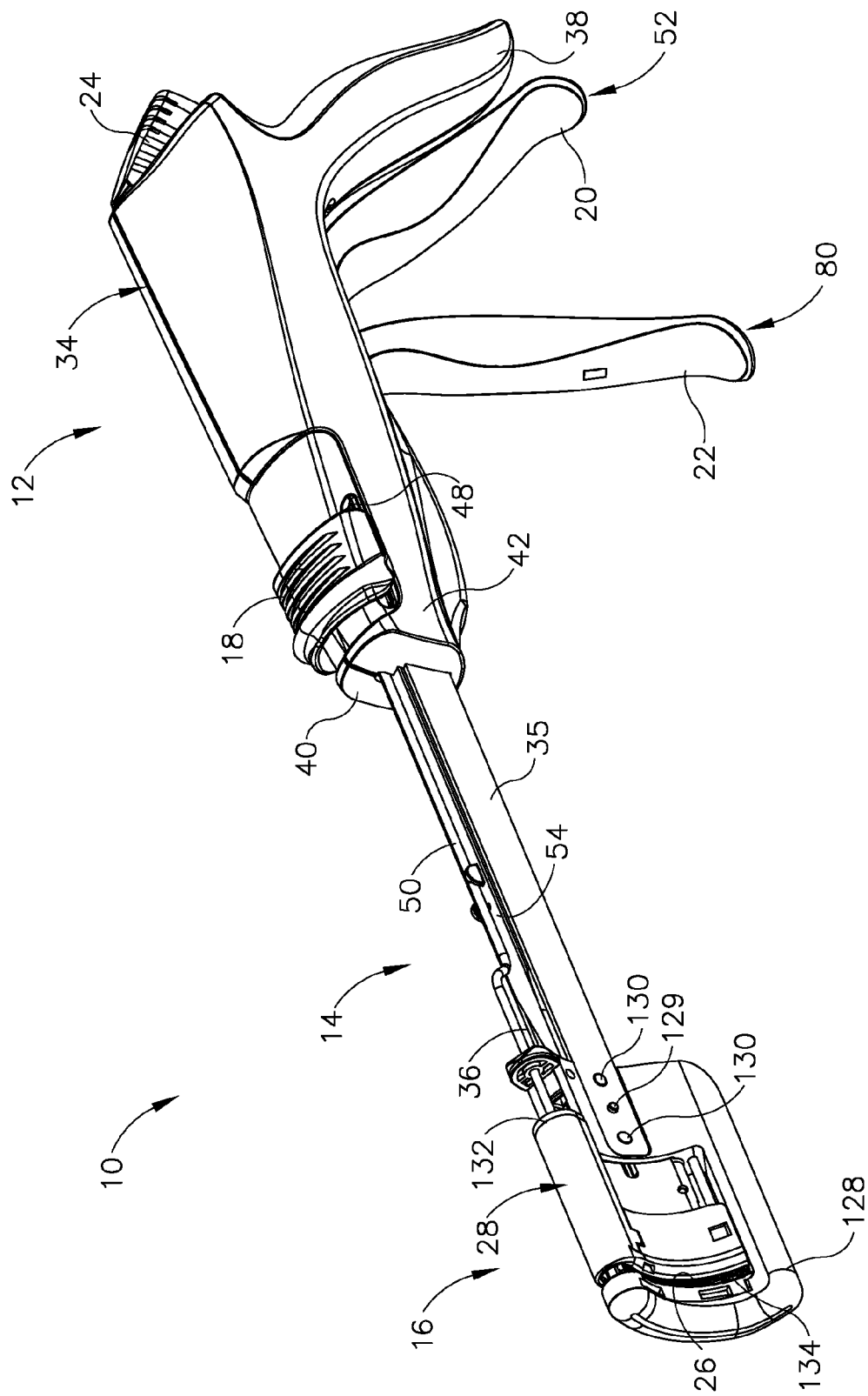
FIG. 1C depicts a right front perspective view of the surgical stapling instrument of FIG. 1A with the pin actuation mechanism in the closed position and the staple cartridge in a closed position via actuation of a closure mechanism.
Figure 1D:
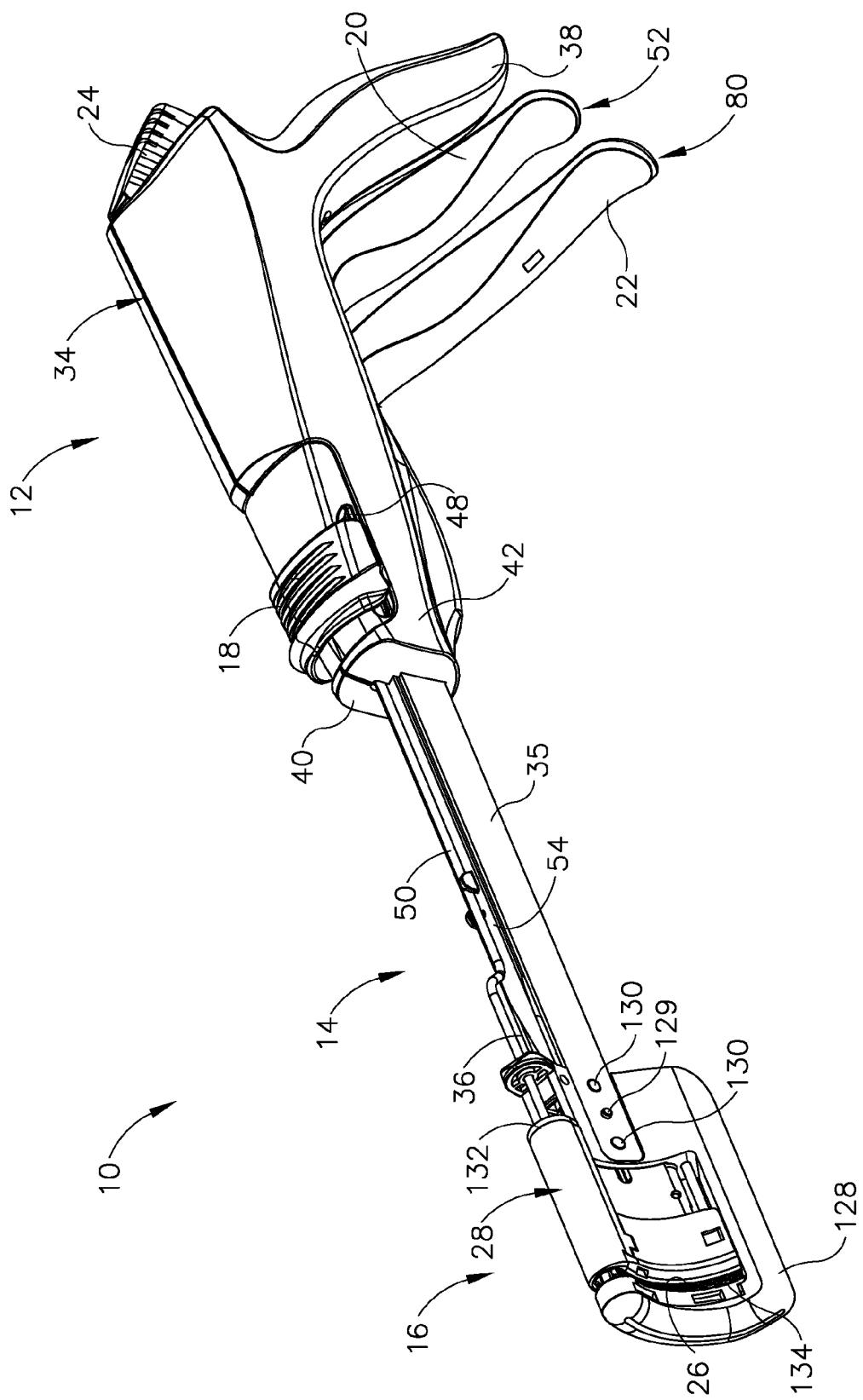
FIG. 1D depicts a right front perspective view of the surgical stapling instrument of FIG. 1A with the pin actuation mechanism and the staple cartridge in the closed positions and a firing trigger in a fired position for stapling and cutting tissue of a patient.
Figure 2B:
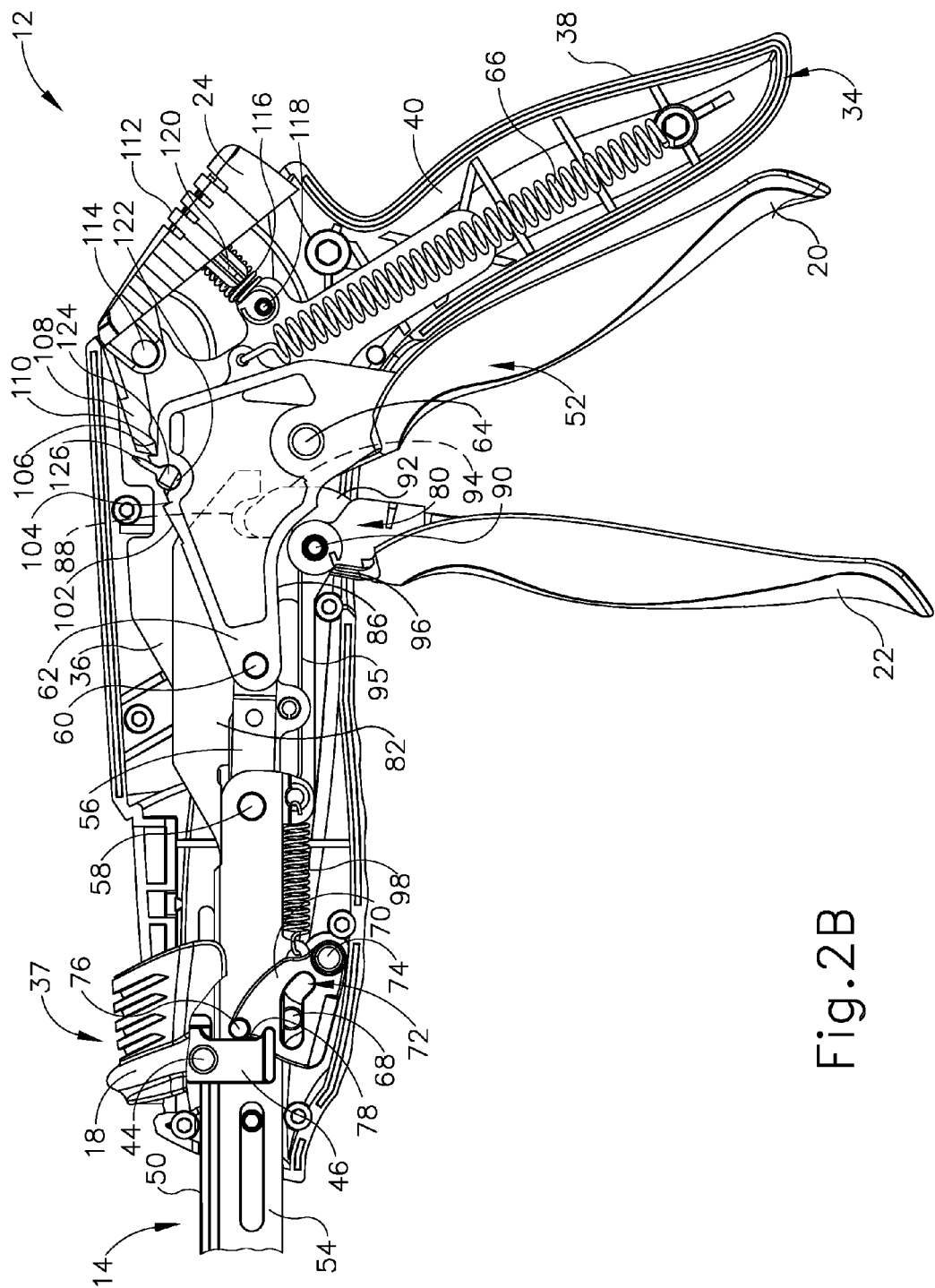
FIG. 2B depicts a right side view of the handle assembly of the surgical stapling instrument of FIG. 1A, with various components removed for clarity, and with the pin actuation mechanism in the closed position and the staple cartridge in the closed position via actuation of the closure mechanism.
Figure 2C:
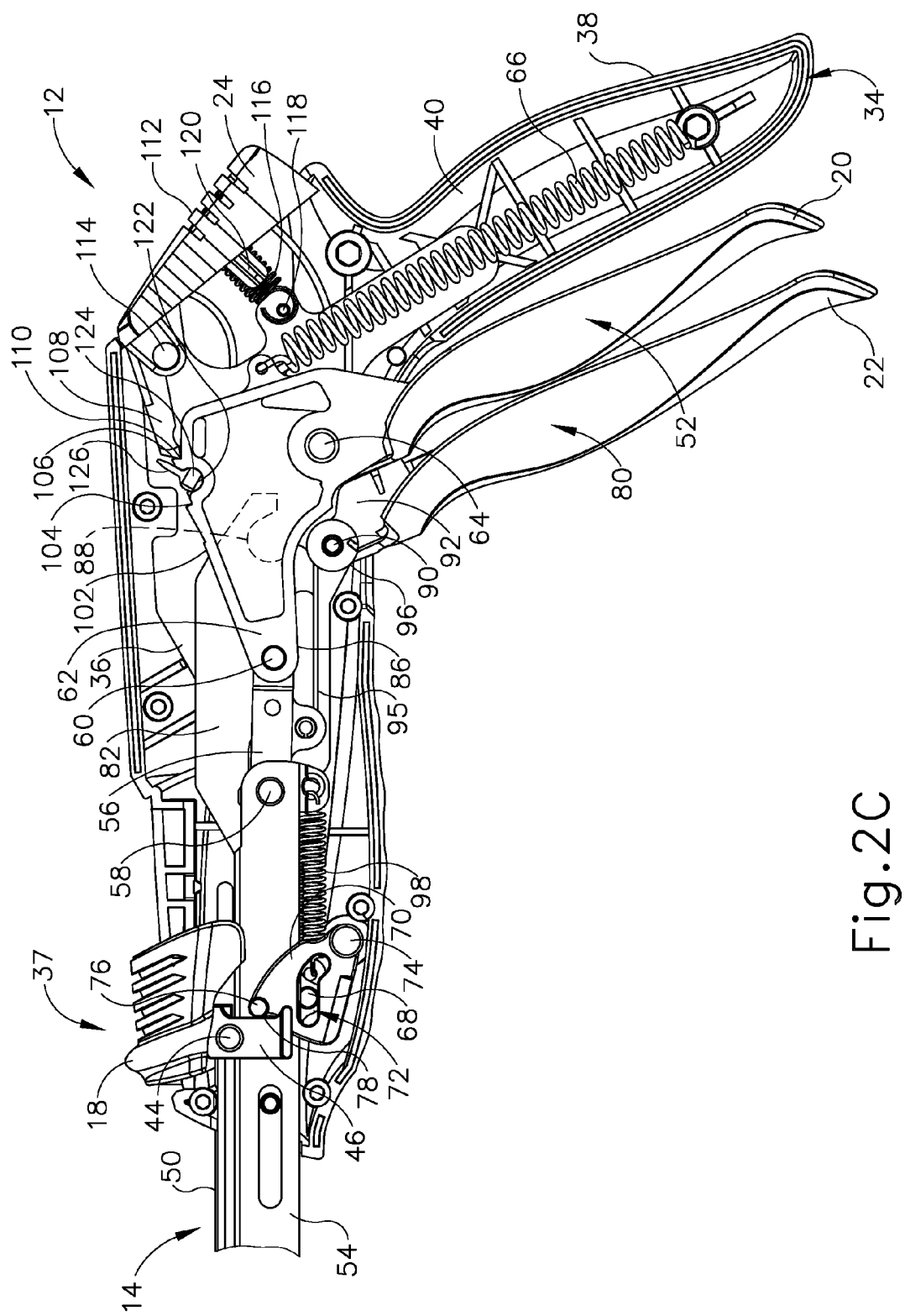
FIG. 2C depicts a right side view of the handle assembly of the surgical stapling instrument of FIG. 1A, with various components removed for clarity, and with the pin actuation mechanism and the staple cartridge in the closed positions and the firing trigger in the fired position for stapling and cutting tissue of a patient.

The operator further squeezes the closure trigger (20) to the hand grip (38) as shown in FIGS. 1C and 2B to effectively set surgical stapling instrument (10) in the closed configuration prior to forming the staples (not shown) and severing the tissue as discussed briefly above. Exemplary handle assembly (12) is configured to form the staples (not shown) and sever the tissue via a firing mechanism (80) upon operator manipulation of firing trigger (22) toward closure trigger (20) as shown in FIGS. 1D and 2C. With respect to FIGS. 1C, 1D, 2B, and 2C, firing mechanism (80), which includes firing trigger (22), has a firing bar (82) extending distally from handle assembly (12) and within end effector (16). A distal end of firing bar (82) cooperates with cartridge (28) as discussed below in greater detail, whereas a proximal end of firing bar (82) is operatively connected to firing trigger (80) for selective firing thereof.

Firing bar (82) has a rectangular receiving slot (84) (see FIG. 2A) in a portion of firing bar (82) positioned within handle housing (34). Integral closure link pin (58) extends through receiving slot (84). The underside of the proximal end portion of firing bar (82) has a sliding surface (86). The proximal end portion of firing bar (82) also has a terminal side engagement surface (82) extending from sliding surface (86). Firing trigger (22) is pivotally mounted to handle frame plates (35, 36) by a firing trigger pin (90) spaced from closure trigger pin (64) such that each of pins (90, 64) pivot about mutually independent axes. Firing trigger (22) includes an arcuate firing trigger link (92) extending from firing trigger (22) at firing trigger pin (90) to an apex (94), which rests on sliding surface (86) of the proximal end portion of firing bar (82). Within handle assembly (12), firing trigger (22) is attached to firing trigger spring arms (95, 96), respectively. Firing trigger spring arms (95, 96) support a torsion spring (not shown) on the right half of firing trigger (22). Finally, a firing bar return spring (98) is secured to the underside of firing bar (82) at the portion of firing bar (82) within handle assembly (12) to bias firing bar (82) toward its unactuated position.

As the operator squeezes closure trigger (20) toward hand grip (38), slotted closure arm link (62) and closure links (56) move distally within receiving slot (84) of firing bar (82). This distal movement causes closure member (54) to correspondingly move distally. Likewise, firing bar (82) concurrently moves distally with closure member (54), because integral closure link pin (58), to which closure links (56) are attached, extends through receiving slot (84) in firing bar (82) (see FIG. 2A). Thereby, firing bar (82) is forced distally to form the staples (not shown) in the tissue and/or sever the tissue with knife (32) (see FIG. 6). Finally, the operator may fully squeeze firing trigger (22) toward hand grip (38) to "fire" surgical stapling instrument (10) and force firing bar (82) further distally to form the staples (not shown) and sever the tissue. This distal movement of firing bar (82) may also be referred to herein as "firing" the firing bar (82) to the actuated or "fired" position.

Upon operator release of one or both of closure and firing triggers (20, 22) while one or both of triggers (20, 22) is/are in a fired position, or in an intermediate position between the unactuated and fired positions, surgical stapling instrument (10) may be further configured to releasably lock in one of a variety of configurations. The operator may then release the hand grip (38) to free one or more hands for another task during the surgical procedure and, when desired, release surgical stapling instrument (10) from its locked position by release button (24). By way of example, surgical stapling instrument (10) has an intermediate closure detent position and a closure detent position. With respect to FIGS. 2A-2C, the top side of the slotted closure arm link (62) has a clamp sliding surface (102) that displays an intermediate detent (104) and a closure detent (106). A release pawl (108) slides on clamp sliding surface (102) and may engage intermediate and closure detents (104, 106). Release pawl (108) has a laterally extending pawl lug (110) at its distal end.

Release pawl (108) is located within handle assembly (12) and is integrally formed with release button (24), which is situated exterior of handle housing (34) for manipulation by the operator. Release button (24) has a thumb rest (112) pivotally attached to handle housing (34) by a release trunnion (114). Release button (24) is biased outwardly from handle housing (34) and, therefore, release pawl (108) is biased downwardly toward clamp sliding surface (102) by a release spring (116). Release spring (116) is mounted to handle housing (34) by a spring retention pin (118) and is mounted to release button (24) by a button spring post (120). Slotted closure arm link (62) has an arcuate recess (122) located between intermediate and closure detents (104, 106). Resting within arcuate recess (122) for rotational movement are integrally connected left and right hand toggles (124). Each toggle (124) has a toggle arm (126) that is engageable with pawl lug (110).

In order to releasably lock handle assembly (12), toggle arms (126) from pawl lug (110) disengage from pawl lug (110) as closure trigger (20) is squeezed toward hand grip (38). Consequently, as toggle (124) continues to rotate in a clockwise direction, release pawl lug (108) rides up toggle arms (126) and, with continued motion of closure trigger (20), falls into one of intermediate and closure detents (104, 106), depending on the position of closure trigger (20) in use. As release pawl (108) rides up toggle arm (126), release pawl (108) rotates release button (24) clockwise. Release pawl (108) thereby falls into one of intermediate and detents (104, 106) and generates an audible clicking sound alerting the surgeon that one of the intermediate and closure positions have been reached.

In order to release handle assembly (12) from the intermediate or closure positions discussed herein, the surgeon depresses release button (24). In turn, release pawl (108) pivots about release trunnion (114) in a clockwise direction to dislodge pawl lug (110) from one of the intermediate and closure detents (104, 106). As pawl lug (110) is dislodged, pawl lug (110) rides on toggle arms (126) to another position, such as the unactuated position. Therefore, the operator may release closure and firing triggers (20, 22) such that each may return to the unactuated positions FIG. 1A and FIG. 3.

Surgical stapling instrument (10) of the present example includes each of handle frame plates (35, 36), push rod (50), closure member (54), and firing bar (82) extending continuously from handle assembly (12) to end effector (16), thereby defining shaft assembly (14) extending therebetween. Handle frame plates (35, 36), push rod (50), closure member (54), and firing bar (82) of surgical stapling instrument (10) provide merely a subset of elongated components extending distally from handle assembly (12) as shaft assembly (14). Alternatively, shaft assembly (14) may include additional components, such as an articulating joint, or may include a rearrangement of various components such that shaft assembly (14) may be modular relative to handle assembly (12). In any case, it will be appreciated that the invention is not intended to be limited to shaft assembly (14) described herein, and may include various alternative arrangements for operatively connecting end effector (16) to handle assembly (12). Of course, handle assembly (12) and shaft assembly (14) may have a variety of other components, features, and operabilities, in addition to or in lieu of any of those noted above. Other suitable configurations for handle and shaft assemblies (12, 14) will be apparent to those of ordinary skill in the art in view of the teachings herein.

B. Exemplary End Effector

Figure 3:
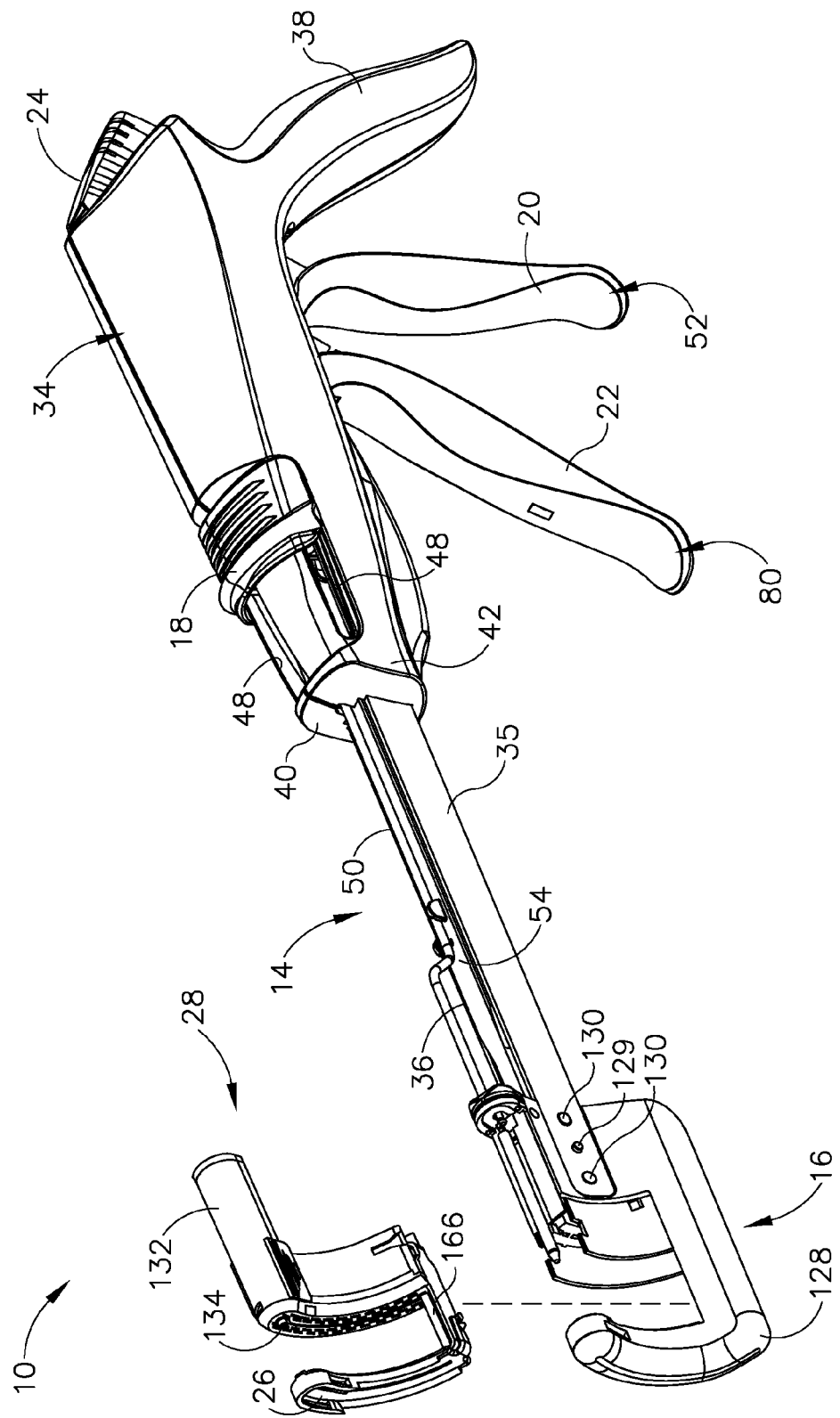
FIG. 3 depicts a partially exploded right front perspective view of the surgical stapling instrument of FIG. 1A showing the staple cartridge removed from a remainder of an end effector.
Figure 4:
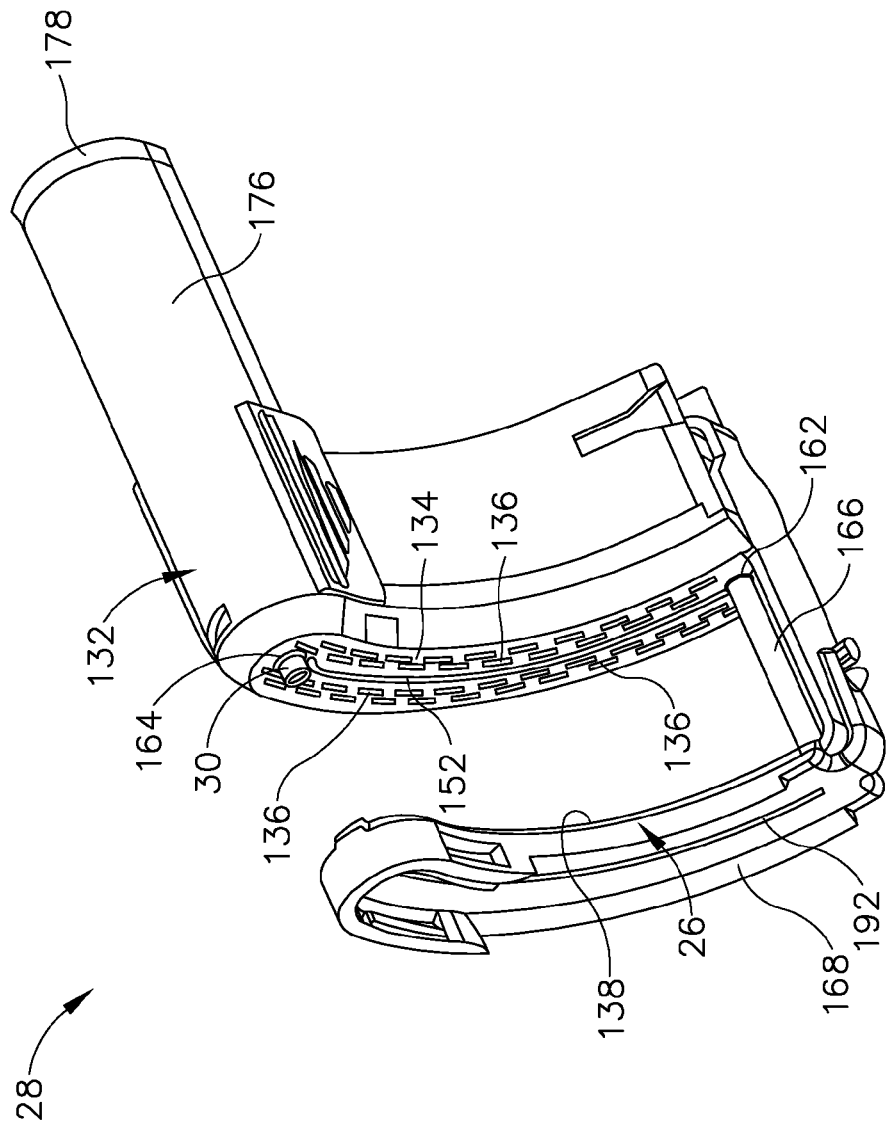
FIG. 4 depicts a right front perspective view of the staple cartridge of FIG. 3.
Figure 5:
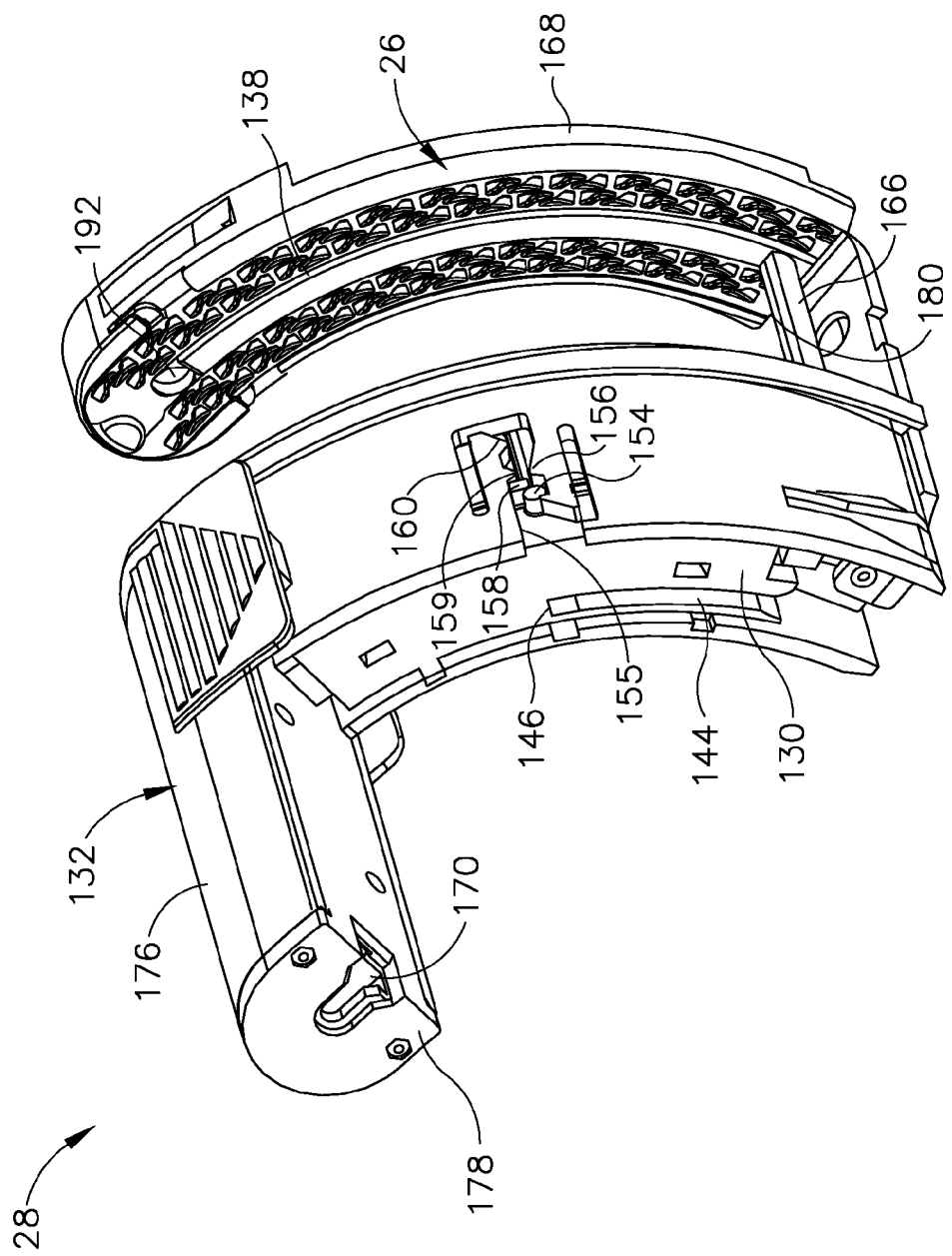
FIG. 5 depicts a rear perspective view of the staple cartridge of FIG. 3.

As also shown in FIGS. 3-5 and discussed briefly above, end effector (16) of the present example includes anvil (26), replaceable cartridge (28) including a plurality of staples (not shown) and knife (32) (see FIG. 6), and retainer pin (30). While end effector (16) of the present example is adapted for use in conjunction with replaceable cartridge (28) having various components, it will be appreciated that the concepts underlying the present invention could be applied to a variety of end effector and cartridge constructions for treating the patient.

End effector (16) provides a surgical fastening assembly that includes cartridge (28) received within a C-shaped supporting structure (128). The term C-shaped is used throughout the specification to describe the concave nature of supporting structure (128) and cartridge (28). The C-shaped construction facilitates enhanced functionality and access to tissue within the patient. The term "C-shaped" as used herein should be construed to include a variety of concave shapes that would similarly enhance the functionality of surgical stapling and cutting instruments. By way of example only, the C-shape of supporting structure (128) may be sized to promote access to the lower colon within the pelvic bowl of a patient, such as to perform a LAR in a proctocolectomy procedure.

Supporting structure (128) of end effector (16) is respectively attached to handle frame plates (35, 36) of shaft assembly (14) by a shoulder rivet (129) and posts (130) which extend from supporting structure (128) into receiving holes in handle frame plates (35, 36). The distal end of closure member (54) is disposed to receive cartridge (28) thereon for directing cartridge (28) to the closed configuration. Upon return of cartridge (28) from the closed configuration to the open configuration, cartridge (28) further includes a safety lockout mechanism (131) (see FIG. 7A) configured to inhibit inadvertently re-firing cartridge (28). Safety lockout mechanism (131) will be discussed below in additional detail.

Cartridge (28) includes anvil (26) coupled to a cartridge housing (132). Cartridge (28) also includes retaining pin (30) and a tissue contacting surface (34), which defines a plurality of staple-containing slots (136) in staggered formation in one or more rows on either side of knife (32) (see FIG. 6). Staples (not shown) are fired from cartridge housing (132) against a staple-forming surface (138) of anvil (26) that faces tissue-contacting surface (134) of cartridge housing (132). Cartridge (28) may also include a removable retainer (not shown) for storage between anvil (26) and tissue contacting surface (34) prior to and/or after use in order to inhibit unintended contact with various portions of cartridge (28).

Figure 6:
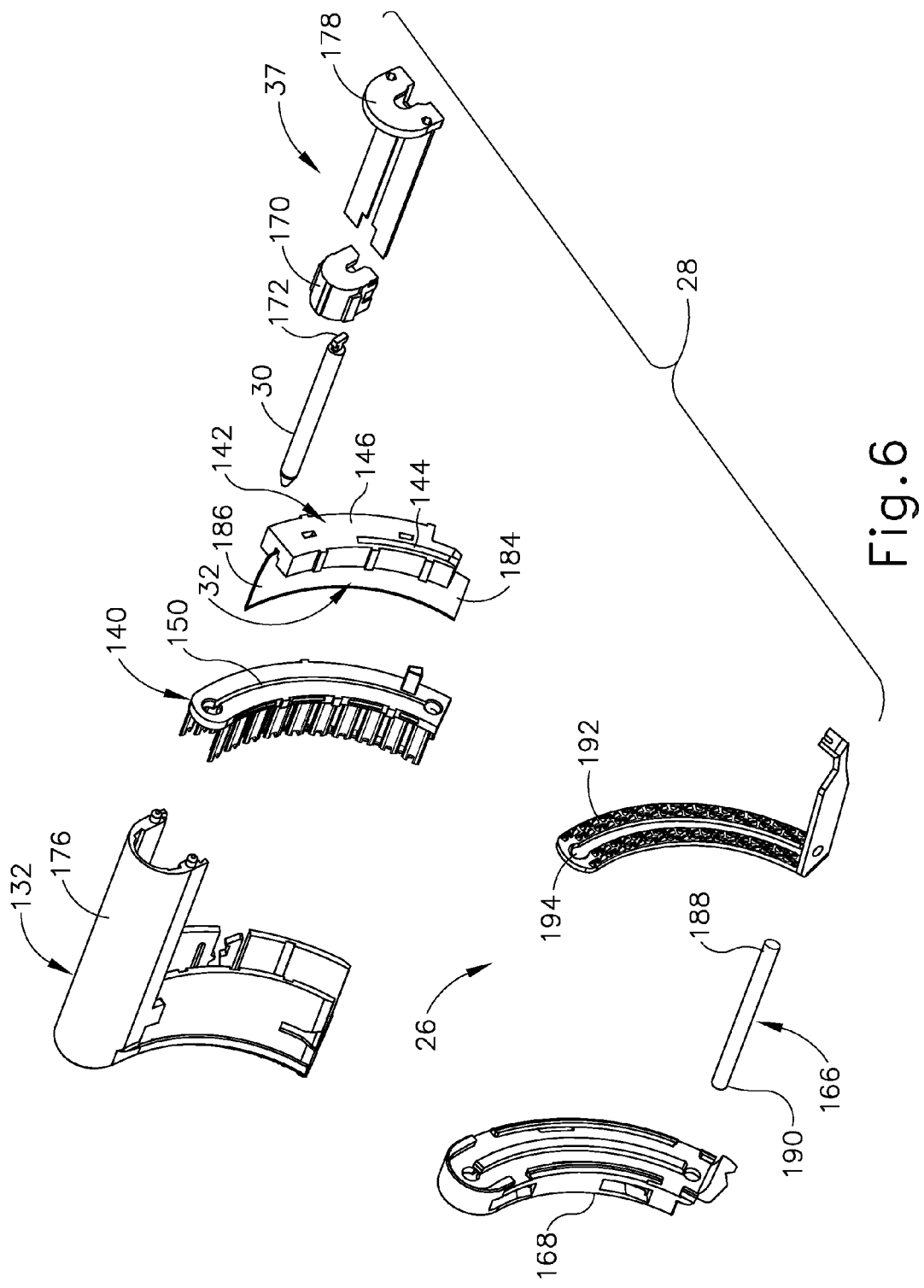
FIG. 6 depicts an exploded rear perspective view of the staple cartridge of FIG. 3.

As shown in FIGS. 4-6, cartridge (28) includes a staple driver assembly (140) within cartridge housing (132) and proximally positioned behind the plurality of staples (not shown) within staple-containing slots (136). Driver assembly (140) of the present example is formed as a unitary structure of a plurality of staple drivers (141). Thus, the term "assembly" is not intended to be limited to an assembly of individual components, but may also include integrally formed components with unitary structures. Driver assembly (140) is configured to push the staples (not shown) respectively out of staple containing slots (136) and toward anvil (26) for formation. A knife holder (142) is disposed immediately proximal of driver assembly (140) in cartridge housing (132) and defines a slot (144) and ledge (146) for interaction with a knife retractor hook (148) (see FIG. 10B), which is discussed below in greater detail. Knife holder (142) is attached to knife (32) such that knife (32) extends distally from knife holder (142) through a slot (150) in driver assembly (140) and through another slot (152) in cartridge housing (132). Although knife (32) is disclosed as being within cartridge housing (132) in the present example, other configurations may also be used. For example, it will be appreciated that cartridge (28) may alternatively not include knife (32) for alternative treatments.

Knife holder (142) has a detent post (154) that extends through a slot (155) in cartridge housing (132). Detent post (154) is positioned in order to contact a detent protrusion (156) of cartridge slot (155) during the longitudinal travel of knife (132) and knife holder (142). Similarly, driver assembly (140) has a detent post (158) positioned in order to contact proximal and distal detent protrusions (159, 160) of cartridge slot (155).

Knife (32) and slots (150, 152) are positioned such that there is at least one row of staples (not shown) on either side of knife (132). In some versions, two rows of staple slots (136) containing respective rows of staples (not shown) are provided on each side of slot (152) of cartridge housing (132).

Cartridge housing (132) defines two longitudinally extending, generally circular holes (162, 164) at respective ends of knife slot (152). More particularly, hole (162) at a lower portion of cartridge housing (132) is shaped and dimensioned to receive a guide pin (166) through cartridge housing (132). Hole (164) at an upper portion of cartridge housing (132) is shaped and dimensioned to slidably receive retaining pin (30) through cartridge housing (132). Staple slots (136) of the present example are arranged such that the staples (not shown) laterally extend past the generally circular holes (162, 164).

Anvil (26) of the present example includes a plastic cutting washer (168) and a metallic staple-forming surface (138). Anvil (26) is disposed to maintain staple-forming surface (138) in alignment with the staples (not shown) to receive and form the staples (not shown) thereon. Retaining pin (30) is connected to a couplet (170) by a circumferential slot (172) in retaining pin (30) and a groove (not shown) in couplet (170). Couplet (170) is disposed within an arm (176) of cartridge housing (132) and is secured to arm (176) by an end cap (178).

Guide pin (166) and retaining pin (30) include respective slots (180, 182) (see also FIGS. 8-9) into which lower and upper ends (184, 186) of knife (32) are slidably disposed. A proximal end (188) of guide pin (166) is connected to anvil (26), whereas a distal end (190) of guide pin (166) extends from cartridge housing (132) and extends through a slot (192) in anvil (26). Cutting washer (168) slips onto anvil (26) via groove (194). Thereby, cutting washer (168) is configured to trap guide pin (166) in the opening formed by slot (192) in anvil (26) and a cutting surface (157) of anvil (26) for connecting anvil (26) to cartridge housing (132).

Figure 7A:
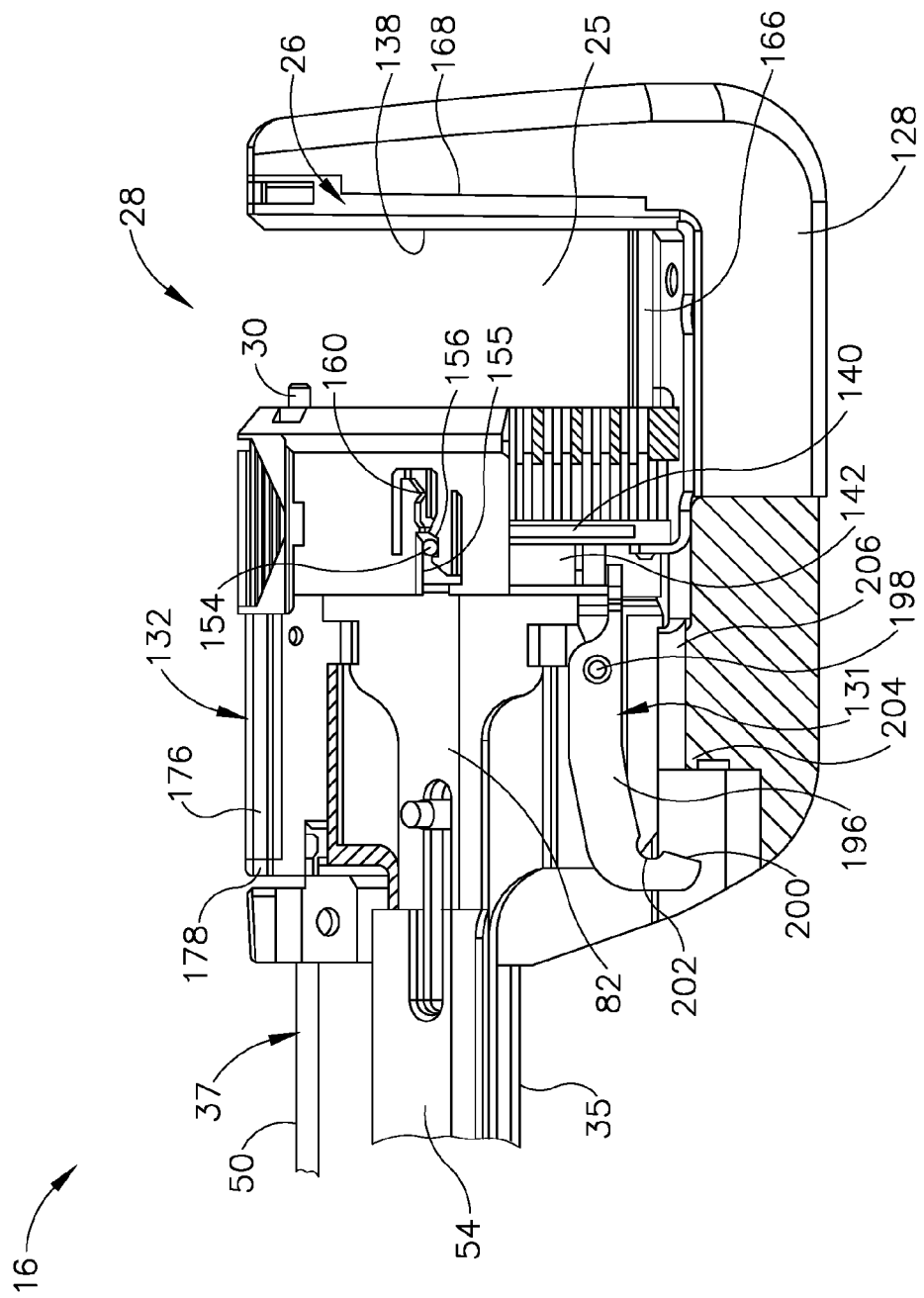
FIG. 7A depicts a left side view of the end effector of FIG. 1A with various components removed for clarity.

Lockout mechanism (131) is shown in FIG. 7A in greater detail. Lockout mechanism (131) is configured to inhibit full proximal movement of cartridge housing (132) to its unactuated position after firing. To this end, lockout mechanism (131) of the present example includes a lockout lever (196) that is pivotally mounted to the distal end of closure member (54) by a pin (198). Lockout lever (196) is spring biased toward the proximal end portion of supporting structure (128) by a spring (not shown). A proximal end portion of lockout lever (196) has a cam surface (200) and a locking groove (202). Supporting structure (128) of end effector (16) also has a ledge (204) that is configured to cooperate with locking groove (202) when lockout mechanism (131) is engaged. In contrast, supporting structure (128) has a base surface (206) configured to cooperate with cam surface (200) when lockout lever (13 is not engaged.

C. Exemplary Actuation of Cartridge

In the present example, cartridge (28) is driven toward anvil (26) via closure member (54) until reaching the closed configuration with tissue positioned between cartridge (28) and anvil (26) as discussed above with respect to handle assembly (12). From the closed configuration, knife (32) and staple driver assembly (140) are further moved toward anvil (26) via firing bar (82) to form staples (not shown) in the tissue, fluidly seal the tissue, and sever the tissue for treating the patient. While actuation of cartridge (28) includes stapling and severing tissue in this example, it will be appreciated that one or more of these steps may be omitted from treatment as desired by the operator. Moreover, it will be appreciated that surgical stapling instrument (10) may be reconfigured to perform these steps simultaneously or sequentially as desired. For example, actuation of firing bar (82) causes driver assembly (140) and knife (32) to move distally toward anvil (26) in the present example. Alternatively, surgical stapling instrument (10) may be reconfigured to selectively fire one of staples (not shown) or knife (32), or selectively fire staples (not shown) and then knife (32), or vice versa. It should therefore be understood that the invention is not intended to be limited to the particular operation of surgical stapling instrument (10) or the associated treatment.

Figure 7B:
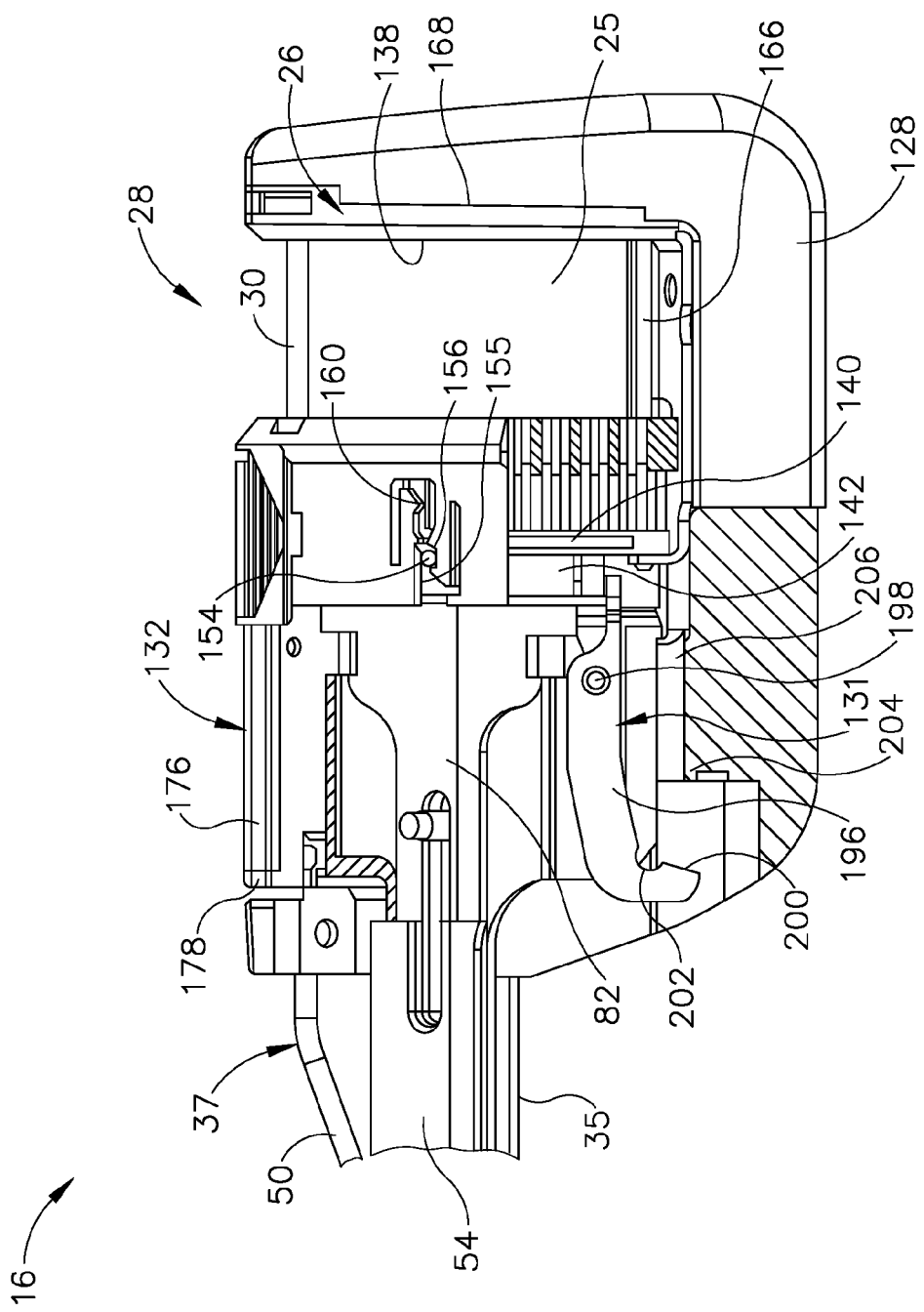
FIG. 7B depicts a left side view of the end effector of FIG. 1A with various components removed for clarity, and with the pin actuation mechanism in a closed position and the staple cartridge in the open position.

As shown in FIG. 7A, cartridge (28) is spaced proximally from anvil (26) to receive tissue within gap (25) in the open configuration. With tissue received between cartridge (28) and anvil (26), the operator manually directs push rod (50) distally via slide (18) as discussed above and shown in FIG. 7B. Push rod (50) is operatively connected to couplet (70) (see FIG. 6), which is connected to retaining pin (30). Thus, distally translating push rod (50) similarly translates retaining pin (30) to extend from cartridge (28) to anvil (26) and capture tissue between retaining pin (30) and guide pin (166).

Figure 7D:
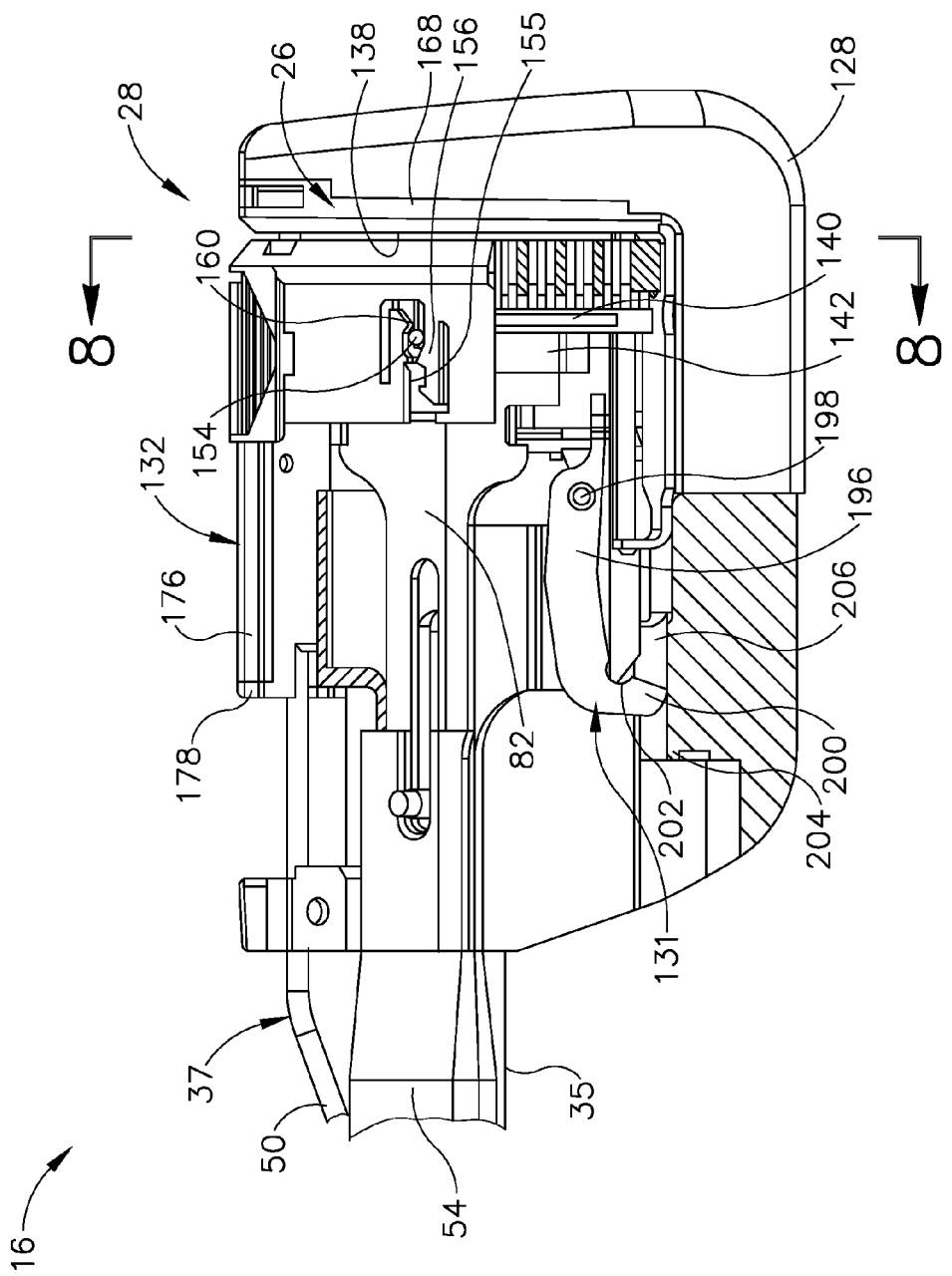
FIG. 7D depicts a left side view of the end effector of FIG. 1A with various components removed for clarity, and with the pin actuation mechanism and the staple cartridge in the closed positions and the firing trigger in the fired position for stapling and cutting tissue of a patient.
Figure 8:
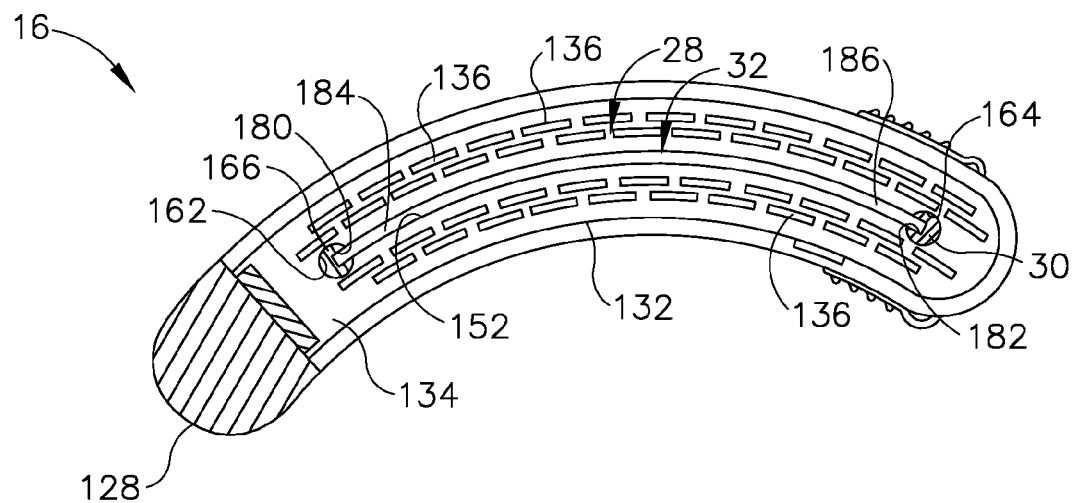
FIG. 8 depicts a cross-sectional view of the end effector of FIG. 7D, taken along section line 8-8 of FIG. 7D.
Figure 9:
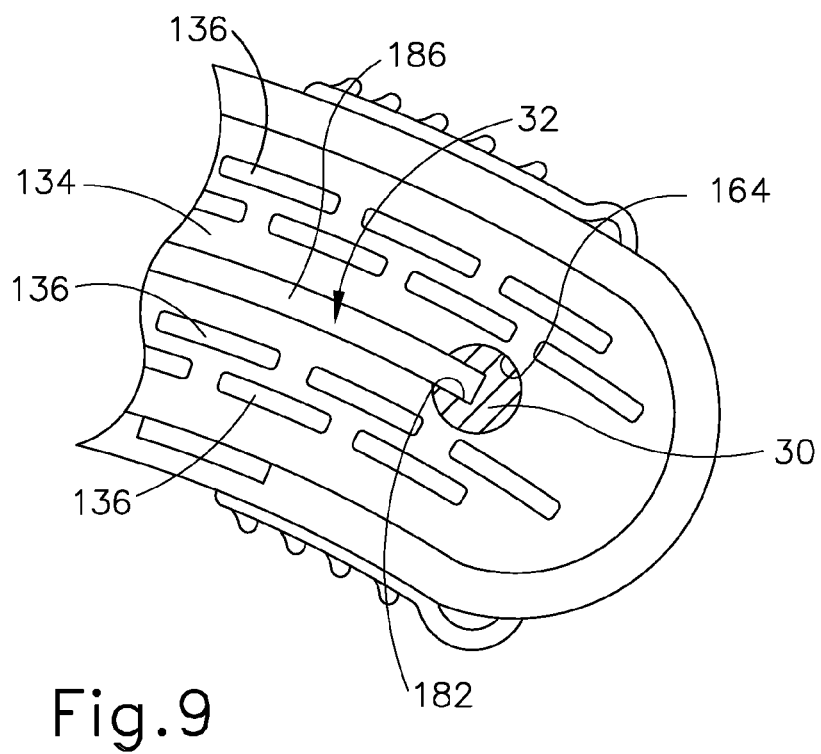
FIG. 9 depicts an enlarged cross-sectional view of a portion of the end effector of FIG. 8.

As shown in FIG. 7C, manipulation of closure trigger (20) (see FIG. 1C) forces closure member (54) to translate distally relative to supporting structure (128) of end effector (16). Closure member (54) supports cartridge (28) thereon such that distal translation of closure member (54) similarly moves firing bar (82) and cartridge (28) toward anvil (26). With cartridge (28) in the closed configuration and the tissue effectively captured in the end effector (16), the operator manipulates firing trigger (22) (see FIG. 1D) toward anvil (26) to the fired position. Distal translation of firing bar (82) causes firing bar (82) to engage knife holder (142), which supports both driver assembly (140) and knife (32) extending through driver assembly (140) as shown in FIG. 7D. In turn, driver assembly (140) directs staples (not shown) from staple slots (136) and against staple-forming surface (138) to form the staples (not shown) within the tissue for fluidly sealing the tissue. As the staples (not shown) are formed, knife (32) continues to translate distally through tissue and into anvil (26) to sever the fluidly sealed tissue. FIGS. 8-9 illustrate the fired cartridge (28) in greater detail, with knife (32) guided along cartridge housing slot (152), guide pin slot (180); and with retaining pin slot (182) between rows of staple slots (136) toward anvil (26).

Figure 10A:
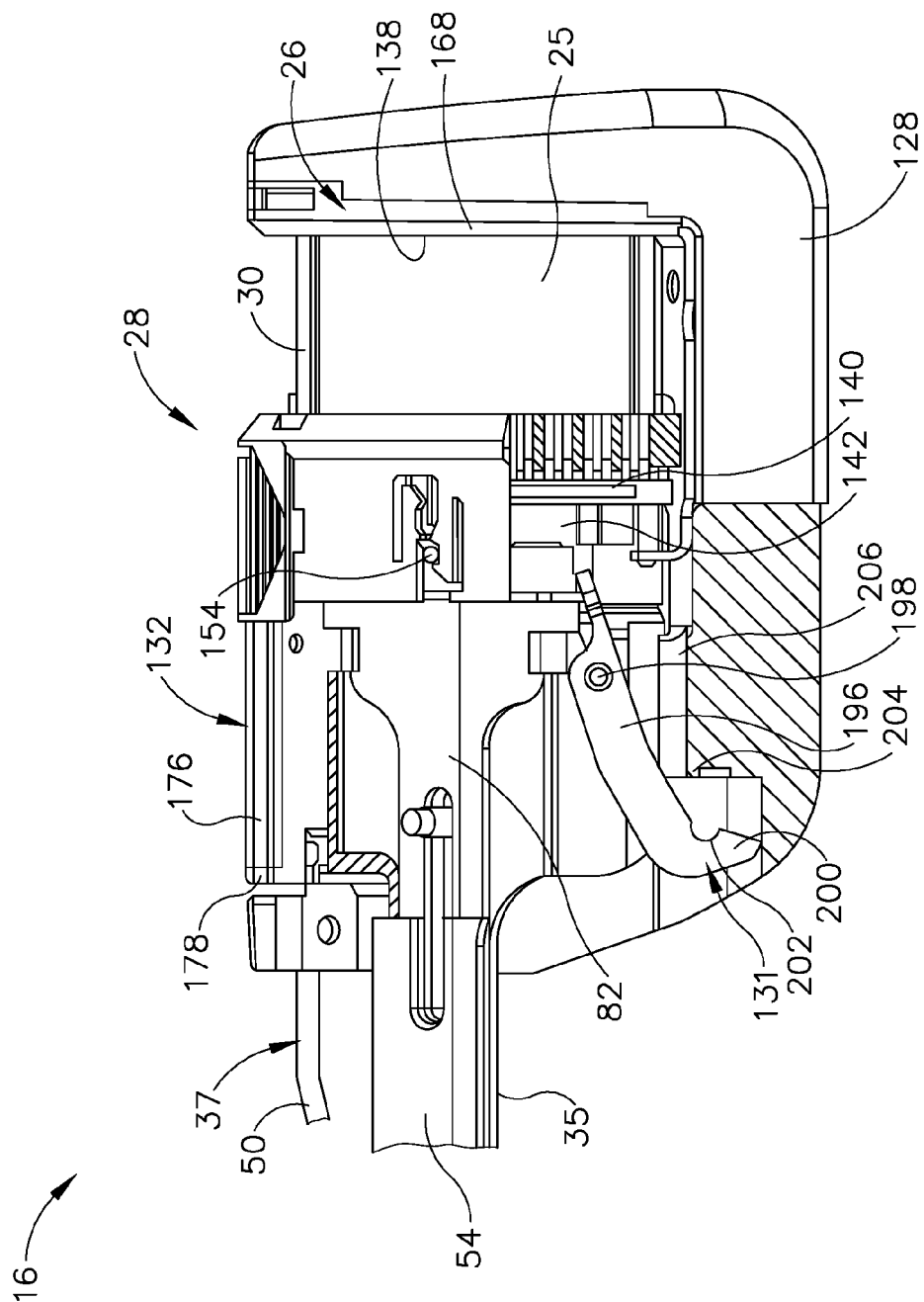
FIG. 10A depicts a left side view of the end effector of FIG. 1A, with various components removed for clarity, with the staple cartridge returned to the open position after actuating the firing trigger.
Figure 10B:
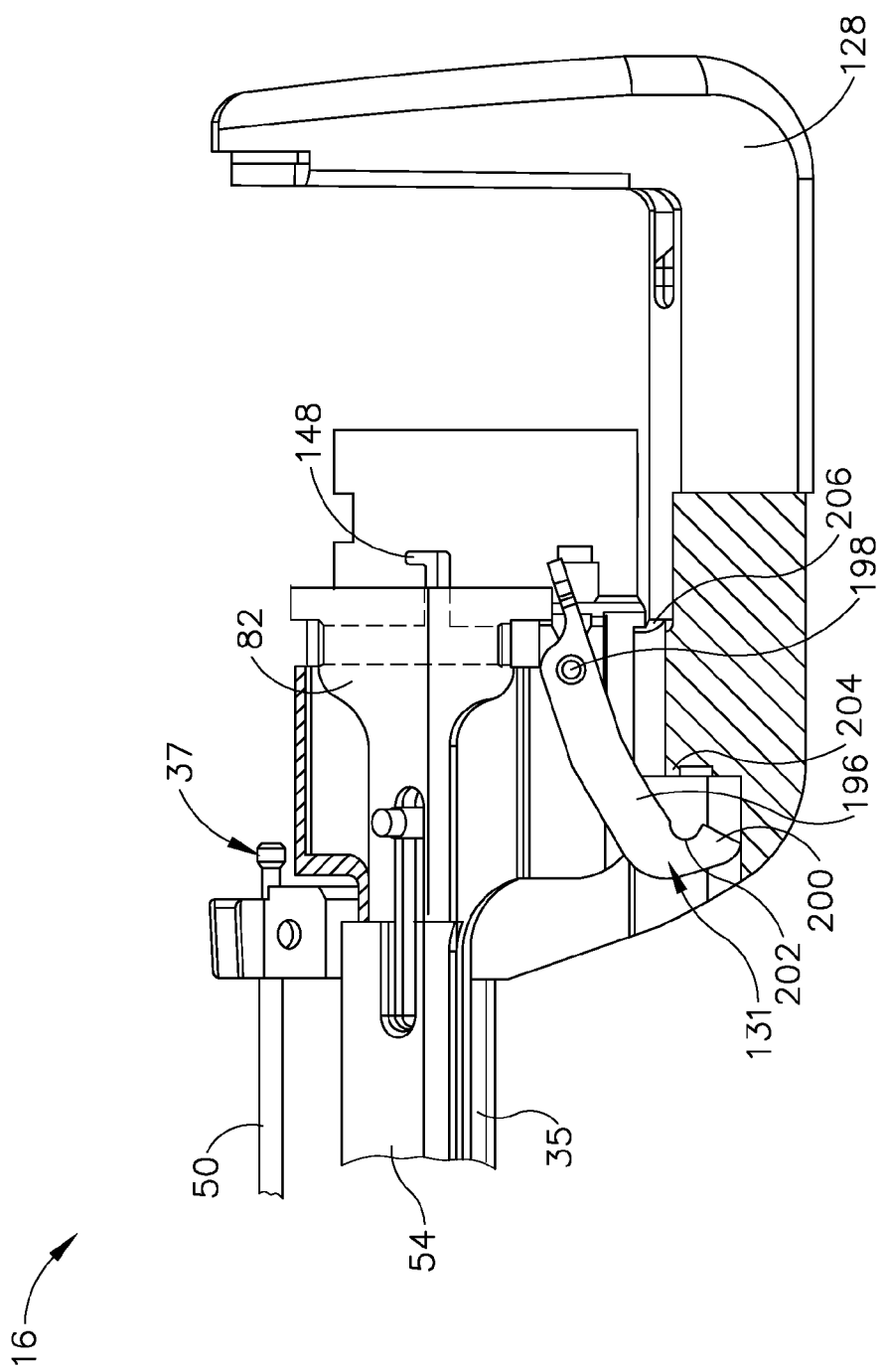
FIG. 10B depicts a left side view of the end effector of FIG. 1A, with various components removed for clarity, with the staple cartridge removed from the remainder of the end effector.

Once fired, the operator may depress release button (24) (see FIG. 2C) and withdraw closure member (54) and firing bar (82) proximally from the actuated, fired position to the unactuated position shown in FIGS. 10A-10B. More particularly, retractor hook (148) engages knife holder (142) to pull knife (32) proximally. At approximately the same time, as cartridge (28) translates proximally with closure member (54), lockout lever (196) of lockout mechanism (131) engages cartridge housing (132) to hold cartridge housing (132) in position. Thereby, the continued pull of knife (32) retracts knife (32) within cartridge housing (132) to inhibit unintended contact by operator with knife (32). Cartridge (28) may then be removed from supporting structure (128) of end effector (16), discarded, and replaced for further treatment if so desired. Of course, various suitable settings and procedures in which surgical stapling instrument (10) may be used will be apparent to those of ordinary skill in the art in view of the teachings herein.

It should also be understood that any other components or features of surgical stapling instrument (10) may be configured and operable in accordance with any of the various references cited herein. Additional exemplary modifications that may be provided for surgical stapling instrument (10) will be described in greater detail below. Various suitable ways in which the below teachings may be incorporated into surgical stapling instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to surgical stapling instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

Figure 14:
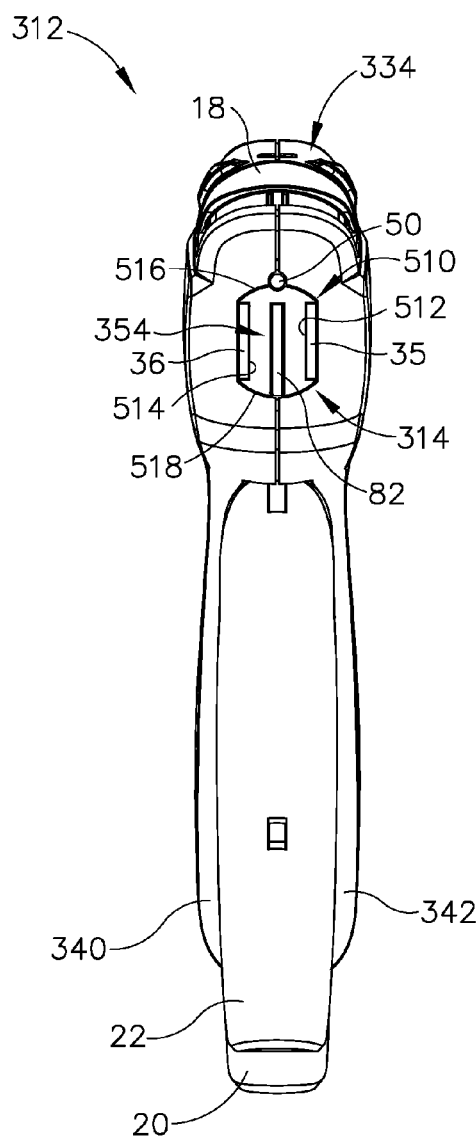
FIG. 14 depicts a cross-sectional end view of another exemplary surgical stapling instrument.
Figure 15:
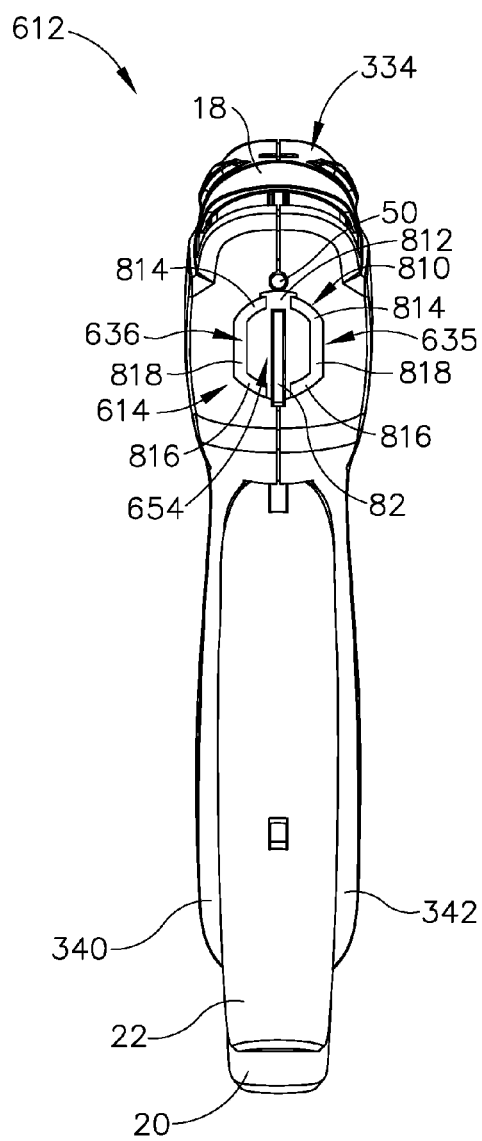
FIG. 15 depicts a cross-sectional end view of another exemplary surgical stapling instrument.

II. Exemplary Surgical Stapling Instruments with Alternative Handle and Shaft Assemblies While the above surgical stapling instrument (10) provides one example of handle assembly (12) having shaft assembly (14) projecting distally therefrom, it will be appreciated that the operator may desire an alternative handle assembly and/or shaft that may be used with end effector (16) or another, alternative end effector depending on one of a variety particular treatments. For example, as the operator manipulates handle assembly (12) such that end effector (16) accesses the tissue within the patient, shaft assembly (14) may also contact the surrounding tissue within the patient. While some tissues may be capable of sustaining contact with shaft assembly (14) without injury, other, more sensitive tissues, may be damaged by contact with shaft assembly (14), particularly in the event that shaft assembly (14) is relatively sharp and rigid in one or more regions. It may therefore be desirable to provide a surgical stapling instrument (310) with a shaft assembly (314, 614) having a relatively rounded outer profile to reduce the likelihood that tissue contact with shaft assembly (314, 614) may inadvertently damage surrounding tissue. The outer profiles of shaft assemblies (314, 614) are best seen in FIGS. 14-15.

Likelihood of injury may be further decreased with additional communication from surgical stapling instrument (10) to the operator regarding the status of instrument operation. In some versions, the operator manipulates one or both of closure and firing triggers (20, 22) to actuate surgical stapling instrument (10) from the open configuration, to the closured configuration, and further to the fired configuration during use. However, due to the hectic nature of the surgical procedure and/or lack of familiarity with surgical stapling instrument (10), the operator may be become unaware of the particular configuration of end effector (16) positioned within the patient. It may therefore be desirable to provide a surgical stapling instrument (310) with a handle assembly (312, 612, 912) that is configured to communicate or indicate the particular configuration of end effector (16) to the operator during use.

Shaft assemblies (314, 614) and handle assemblies (312, 612, 912) are described below in the context of a proctocolectomy surgical procedure. While the following description of shaft and handle assemblies (314, 614, 312, 612, 912) and method of treatment is provided in the context of stapling and/or cutting colon tissue, it will be appreciated that surgical stapling instrument (310) and any of shaft and handle assemblies (314, 614, 312, 612, 912) may be alternatively configured to treat any tissue in the human body with similar features. It should also be understood that the features discussed below may be readily incorporated into surgical stapling instrument (10) discussed above. To this end, like numbers indicate like features described above in greater detail.

Figure 11:
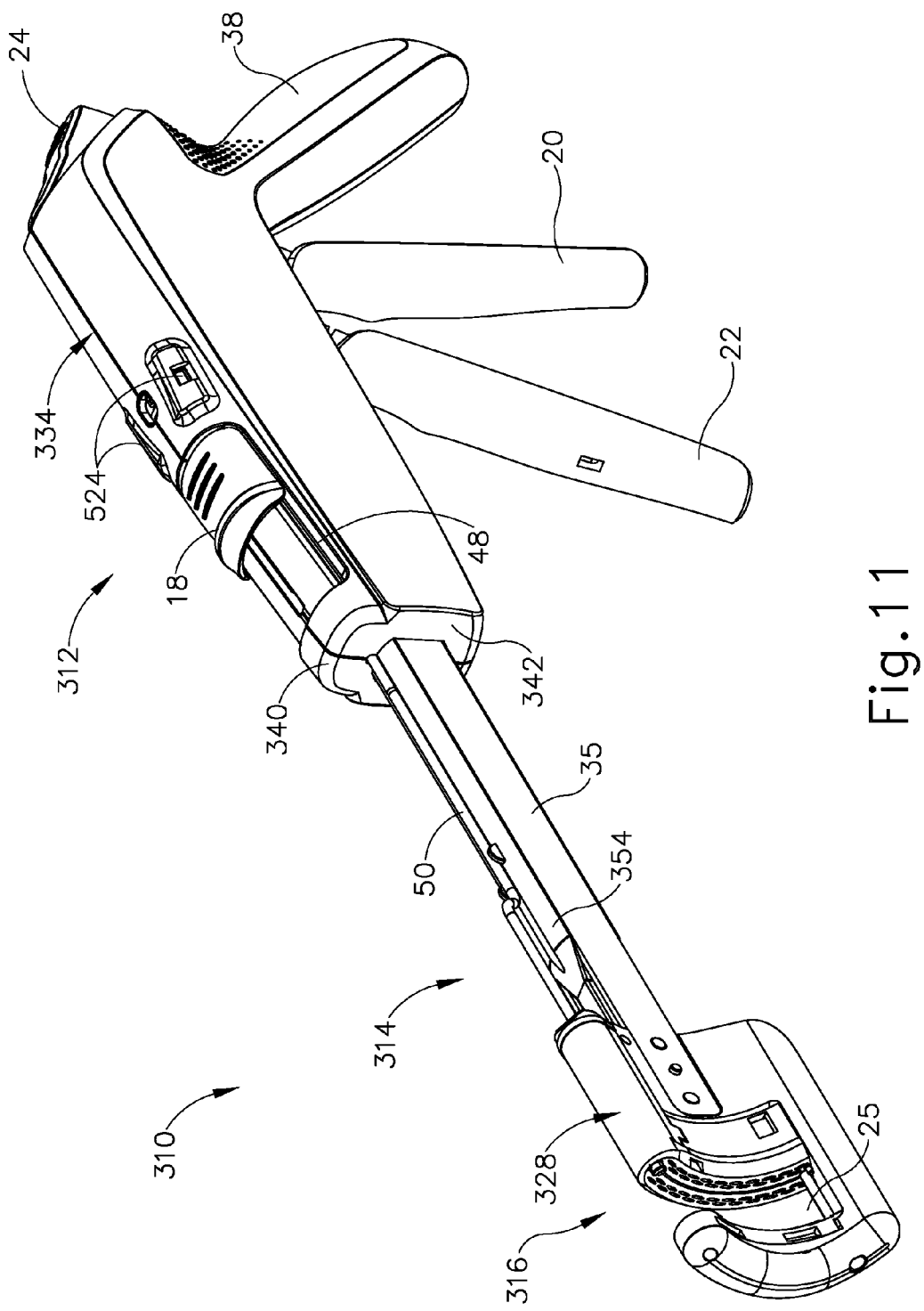
FIG. 11 depicts a right perspective view of another exemplary surgical stapling instrument.
Figure 12:
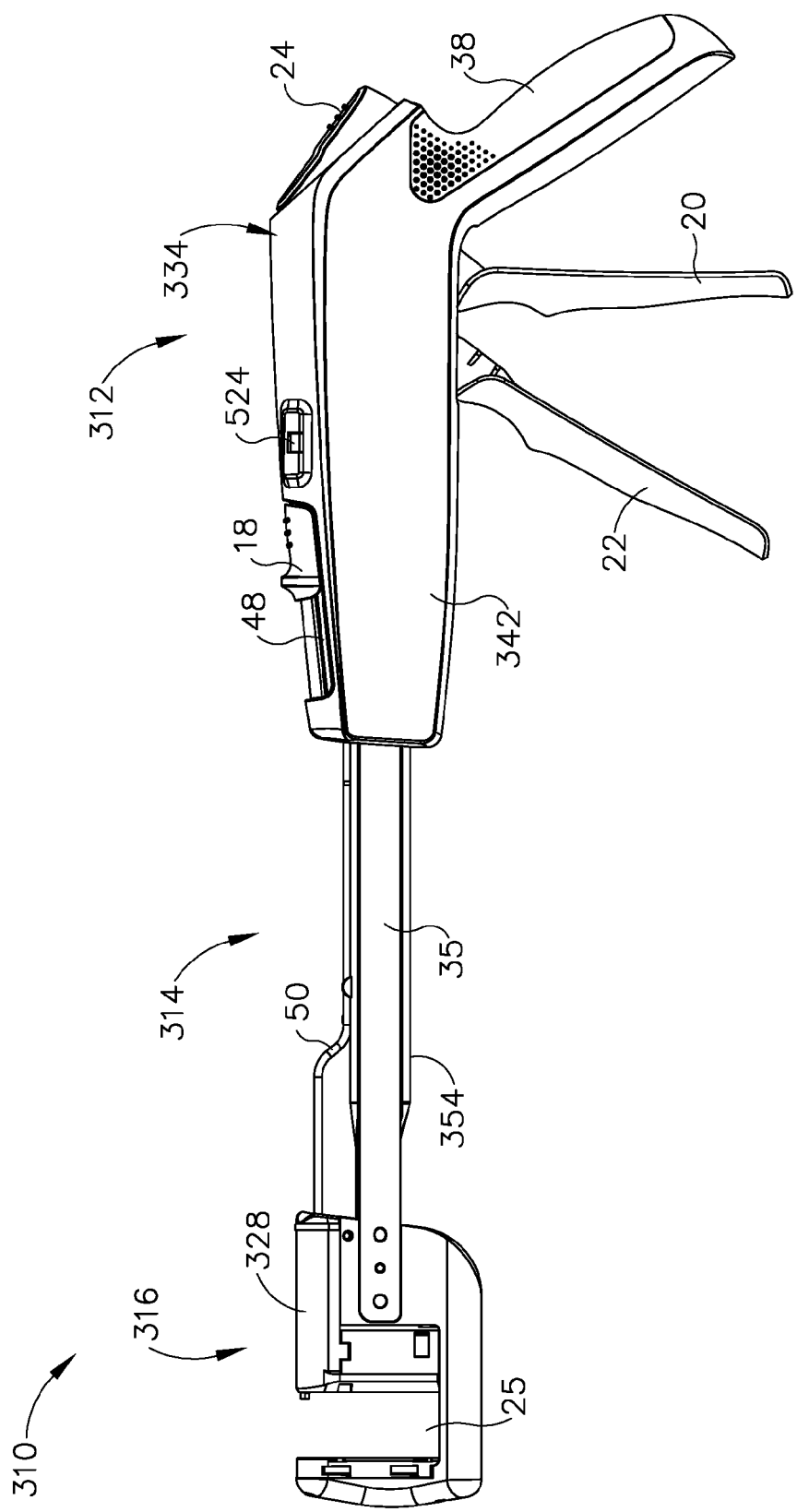
FIG. 12 depicts a right side view of the surgical stapling instrument of FIG. 11.
Figure 13:
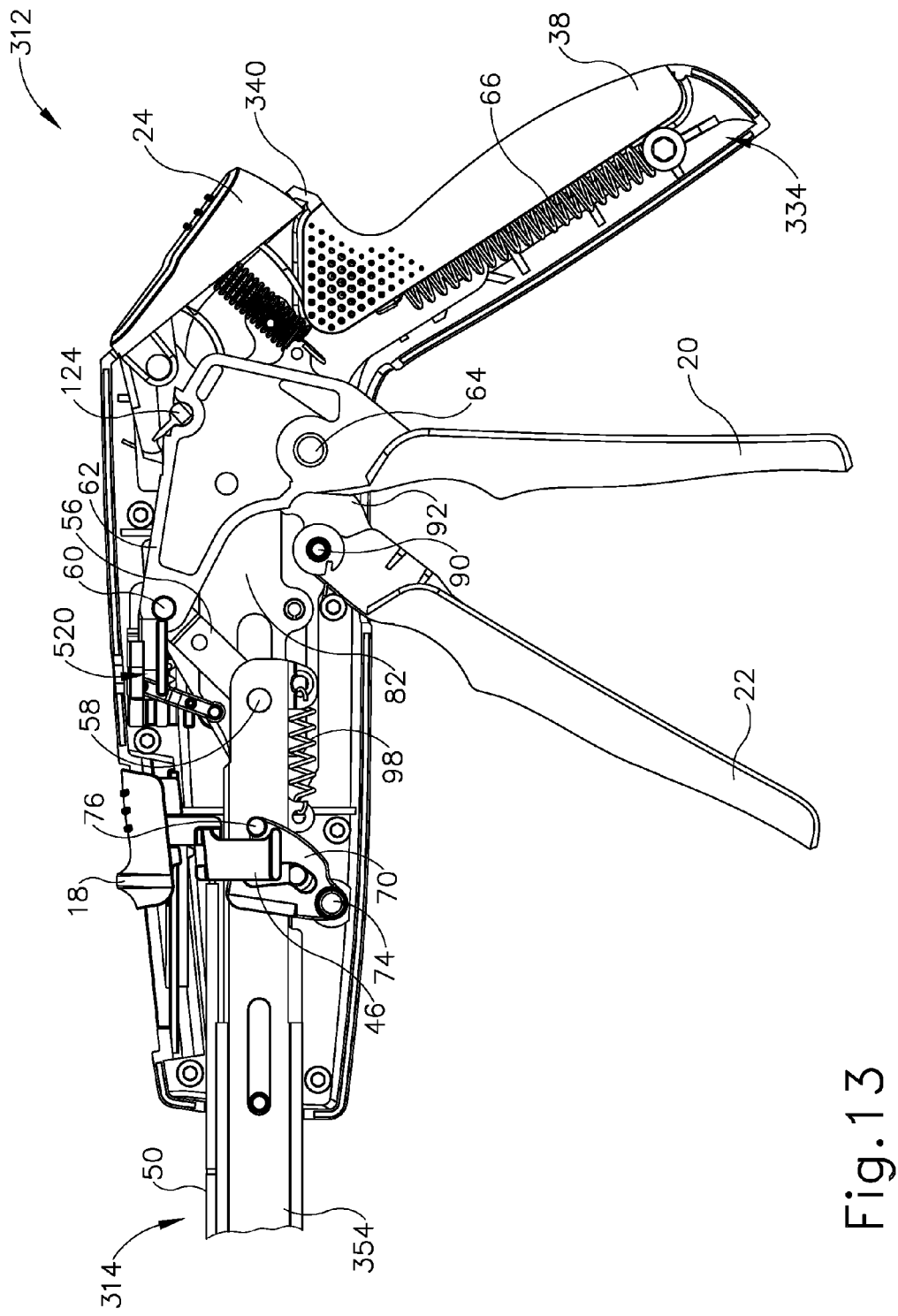
FIG. 13 depicts a right side view of a handle assembly of the surgical stapling instrument of FIG. 12, with various components removed for clarity.

A. Exemplary Surgical Stapling Instrument Having Shaft Assembly with a Rounded Outer Profile FIGS. 11-13 show surgical stapling instrument (310) with handle assembly (312) and shaft assembly (314) extending distally from handle assembly (312). An end effector (316) extends distally from shaft assembly (314) and is configured to fluidly seal and sever tissue with staples (not shown) and knife (32) (see FIG. 6) similar to end effector (16) discussed above in greater detail. To this end, the operator squeezes closure trigger (20) to selectively translate a closure member (354) distally to the closed configuration with tissue captured therein. The operator further squeezes firing trigger (22) to selectively translate firing staples (not shown) and knife (32) (see FIG. 6) from a cartridge (328).

1. Exemplary Shaft Assembly with Rounded Closure Member

FIGS. 12-14 show shaft assembly (314) in greater detail. Shaft assembly (314) defines a rounded outer profile (510) that is generally continuous about shaft assembly (314) and is thereby configured to avoid damaging tissue upon contact with tissue during use of instrument (310) in a surgical procedure. Rounded outer profile (510) is more particularly defined collectively by left and right handle frame plates (35, 36), closure member (354), firing bar (82), and push rod (50) extending along an upper portion of closure member (354). Closure member (354) has a pair of lateral slots (512, 514) extending longitudinally therealong that are configured to receive handle frame plates (35, 36), respectively. In addition, closure member (354) has an upper rounded surface (516) and an opposing lower rounded surface (518), whereas handle frame plates (35, 36) are generally planar so as to be received within respectively lateral slots (512, 514). Frame plates (35, 36) are thereby flush with the surrounding upper and lower rounded surfaces (516, 518) so as to be free of sharp or abrasive edges that may damage tissue. Rounded outer profile (510) thus has rounded upper and lower portions that may pass along tissue atraumatically. However, it will be appreciated that alternative shaft assemblies with alternative rounded outer profiles may be constructed for inhibiting such tissue damage.

2. Exemplary Shaft Assembly with Rounded Handle Frame Plates

Figure 16:
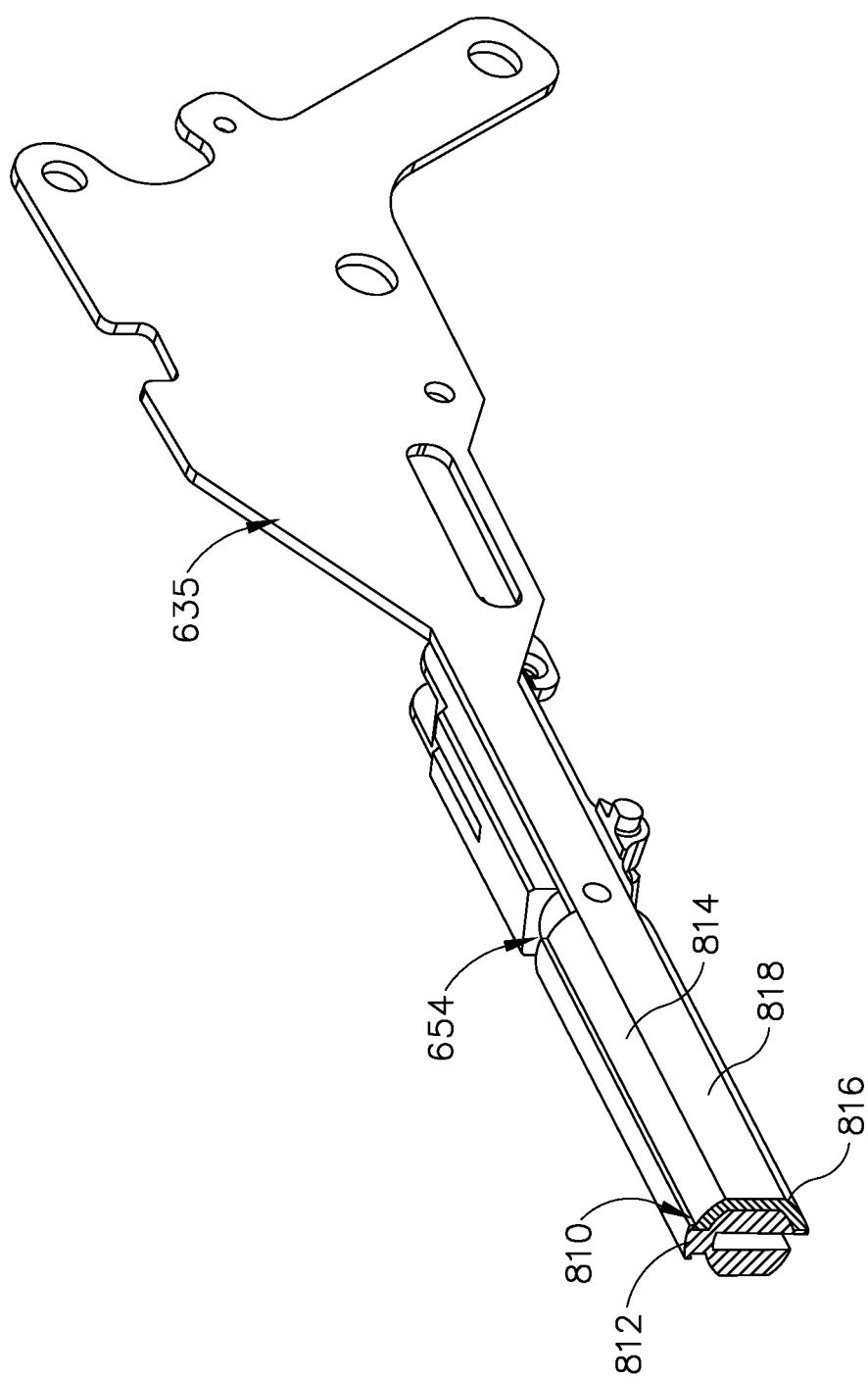
FIG. 16 depicts a right front sectional perspective view of a portion of the shaft assembly of the surgical stapling instrument of FIG. 15.

Another exemplary shaft assembly (614) is also configured to avoid damaging tissue via an alternative rounded outer profile (810) shown in FIGS. 15-16. Rounded outer profile (810) is collectively defined by left and right rounded frame plates (635, 636), a closure member (654), firing bar (82), and push rod (50) extending along an upper portion of closure member (654). Closure member (654) includes an upper cap (812) extending upwardly therefrom. In addition, rounded frame plates (635, 636) each have rounded upper and lower portions (814, 816) with a planar intermediate portion (818) extending therebetween to define a generally C-shape. Rounded upper portions (814) of each rounded frame plate (635, 636) are positioned partially under upper cap (812) to be generally flush with upper cap (812). The planar intermediate portions (818) and lower rounded portions (816) of each rounded frame plate (635, 636) cradle opposing lateral sides of closure member (654) such that closure member (654) is generally surrounded by rounded frame plates (635, 636) on each lateral side. Rounded outer profile (810) thus has rounded upper and lower portions that may pass along tissue during use with reduced abrasiveness that may otherwise damage the tissue.

B. Exemplary Surgical Stapling Instrument with Feedback Generator

FIGS. 11-13 and 17 show surgical stapling instrument (310) with handle assembly (312) and shaft assembly (314) extending distally from handle assembly (312). End effector (316) extends distally from shaft assembly (314) and is configured to fluidly seal and sever tissue with staples (not shown) and knife (32) (see FIG. 6) similar to end effector (14) discussed above in greater detail. To this end, the operator squeezes closure trigger (20) to selectively translate a closure member (354) distally to the closed configuration with tissue captured therein. The operator further squeezes firing trigger (22) to selectively translate firing staples (not shown) and knife (32) (see FIG. 6) from a cartridge (328).

During manipulation of closure and firing triggers (20, 22), a feedback generator (520, 820, 822, 1110, 1112) contained within handle assembly (312) is configured to provide at least one of an audible feedback, a visual feedback, or a tactile feedback to the operator in real time with respect to the operational state or configuration of the surgical stapling instrument (310). For example, surgical stapling instrument (310) may provide feedback when firing trigger (22) fires firing bar (82) a full distal stroke so that the operator may confirm the end of stroke via the feedback.

1. Exemplary Translational Feedback Generator with Audible and Visual Feedback

FIGS. 17-20 show exemplary handle assembly (312) having a translational feedback generator (520) that is configured to generate audible and visual feedback when firing trigger (22) fires firing bar (82) to form staples (not shown) and sever the tissue as discussed above. Translational feedback generator (520) includes a slide feedback assembly (522) supported within a handle housing (334) and adjacent to indicia windows (524), which extend through handle housing (334) for operator view of slide feedback assembly (522) in use. Handle housing (334) also supports a sound generator (526) adjacent to slide feedback assembly (522) such that distal movement of slide feedback assembly (522) causes slide feedback assembly (522) to pluck sound generator (526) to generate an audible click when firing bar (82) is fired. Sound generator (526) may also be configured to temporarily increase resistance to manipulation of firing trigger (22) as sound generator (526) is plucked to further generate tactile feedback to the operator through firing trigger (22).

Figure 17:
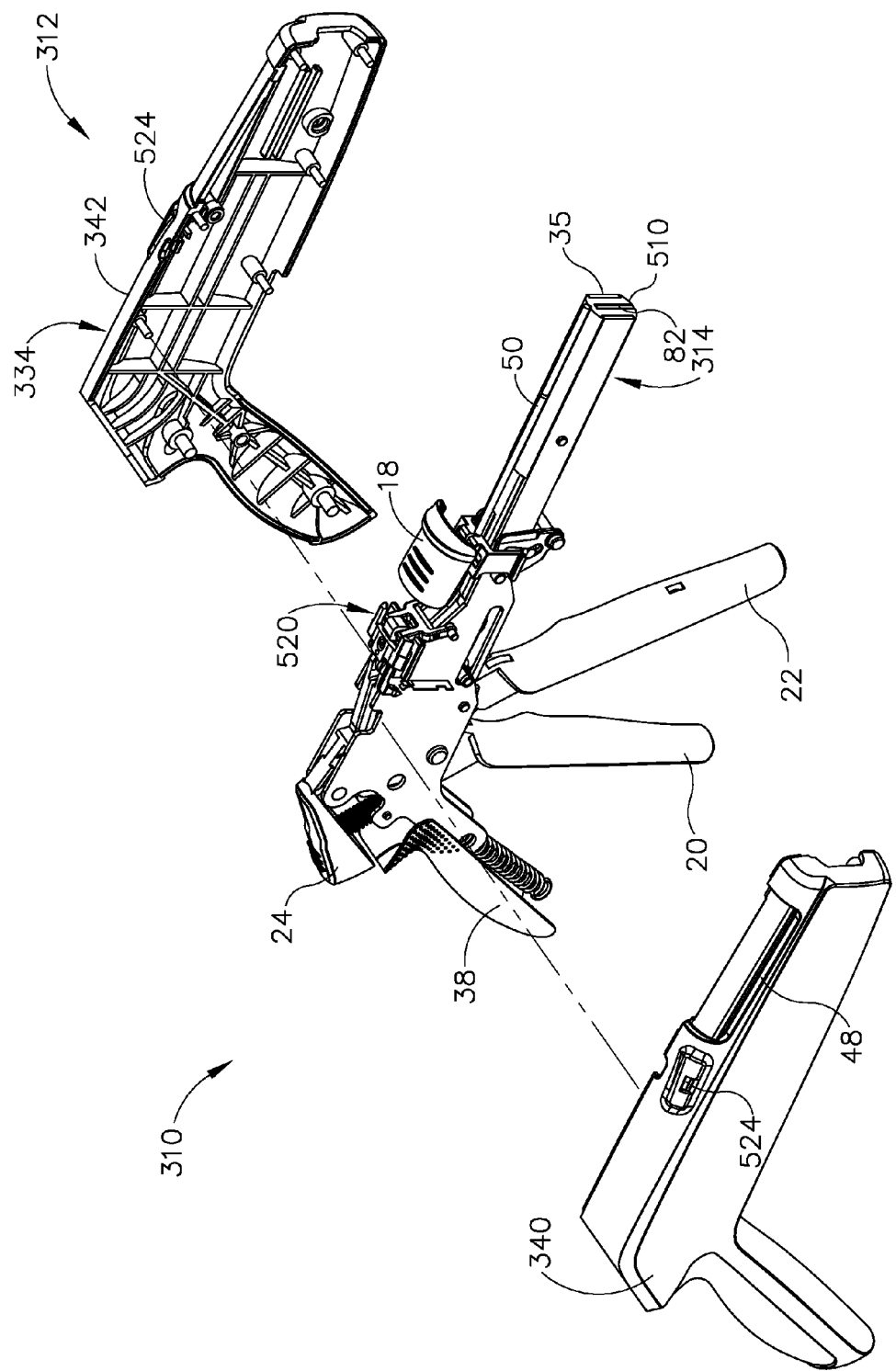
FIG. 17 depicts a partially exploded left front perspective view of a handle assembly of the surgical stapling instrument of FIG. 11, with a left shroud portion and a right shroud portion separated from other components of the handle assembly.
Figure 18:
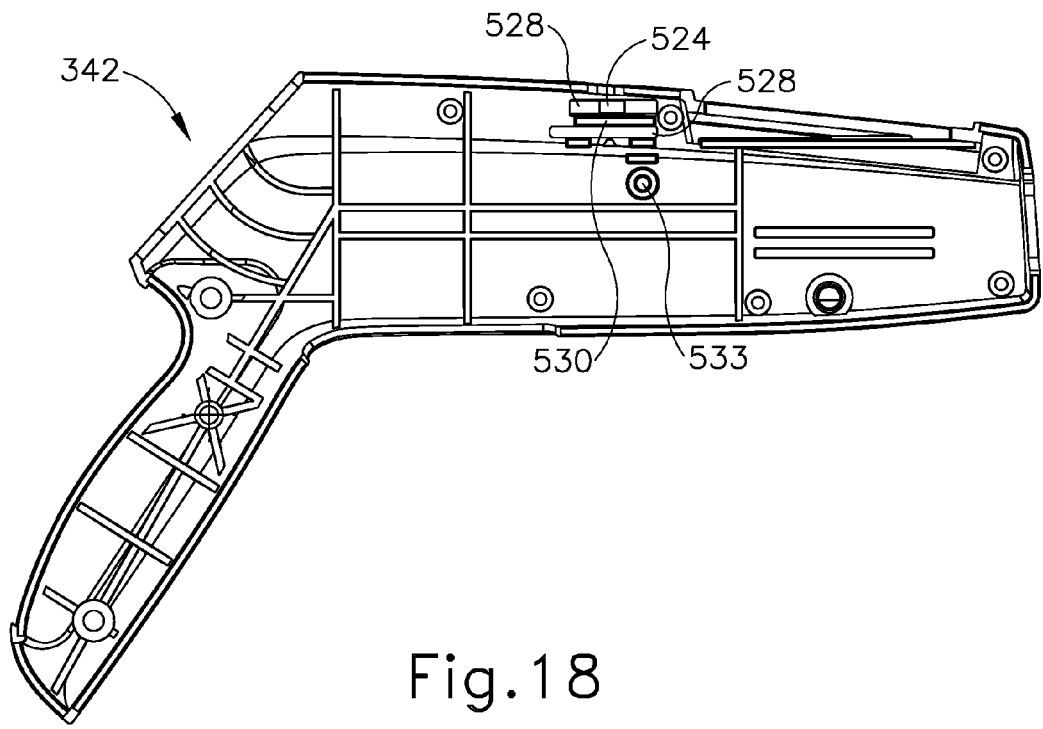
FIG. 18 depicts a left side view of a left shroud portion of the handle assembly of FIG. 17.
Figure 19:
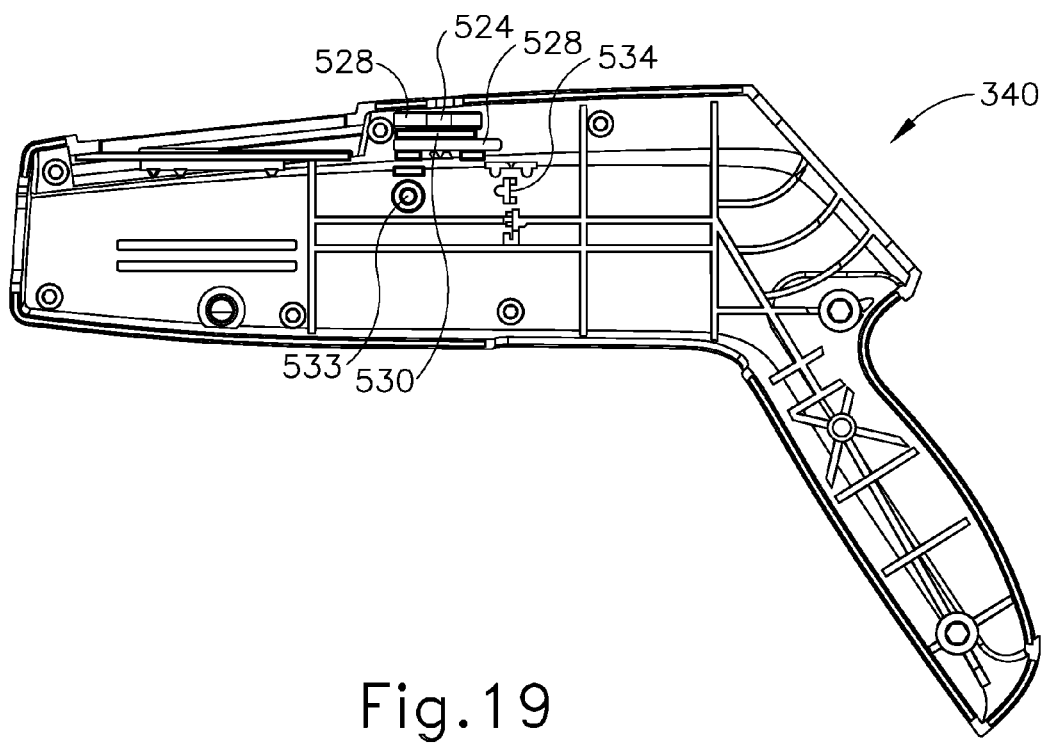
FIG. 19 depicts a right side view of a right shroud portion of the handle assembly of FIG. 17.

FIGS. 17-19 show inner surfaces of left and right shroud handle portions (342, 340) that collectively form handle housing (334) upon assembly. Each shroud handle portion (342, 340) includes a pair of offset support guides (528) extending inwardly to define a pair of slide channels (530) on opposing sides of handle housing (334). Each slide channel (530) slidably receives a lateral end of a sled (532) (see FIG. 20) such that sled (532) (see FIG. 20) is slidably supported between support guides (528). Slide feedback assembly (522) is further connected to mount holes (533) extending inwardly from left and right shroud handle portions (342, 340) and will be discussed below in additional detail. Right shroud handle portion (342) further includes a mounting arrangement (534) in which to secure sound generator (526) (see FIG. 20) adjacent to slide feedback assembly (522). In order to provide viewing of slide feedback assembly (522), each exemplary shroud handle portion (342, 340) includes one indicia window (524) adjacent to a respective support guide (528) for viewing one of a plurality of indicia operatively connected to sled (532) (see FIG. 20) as sled (532) (see FIG. 20) moves along slide channels (530) to indicate whether or not surgical stapling instrument (310) has been fired.

Figure 20:
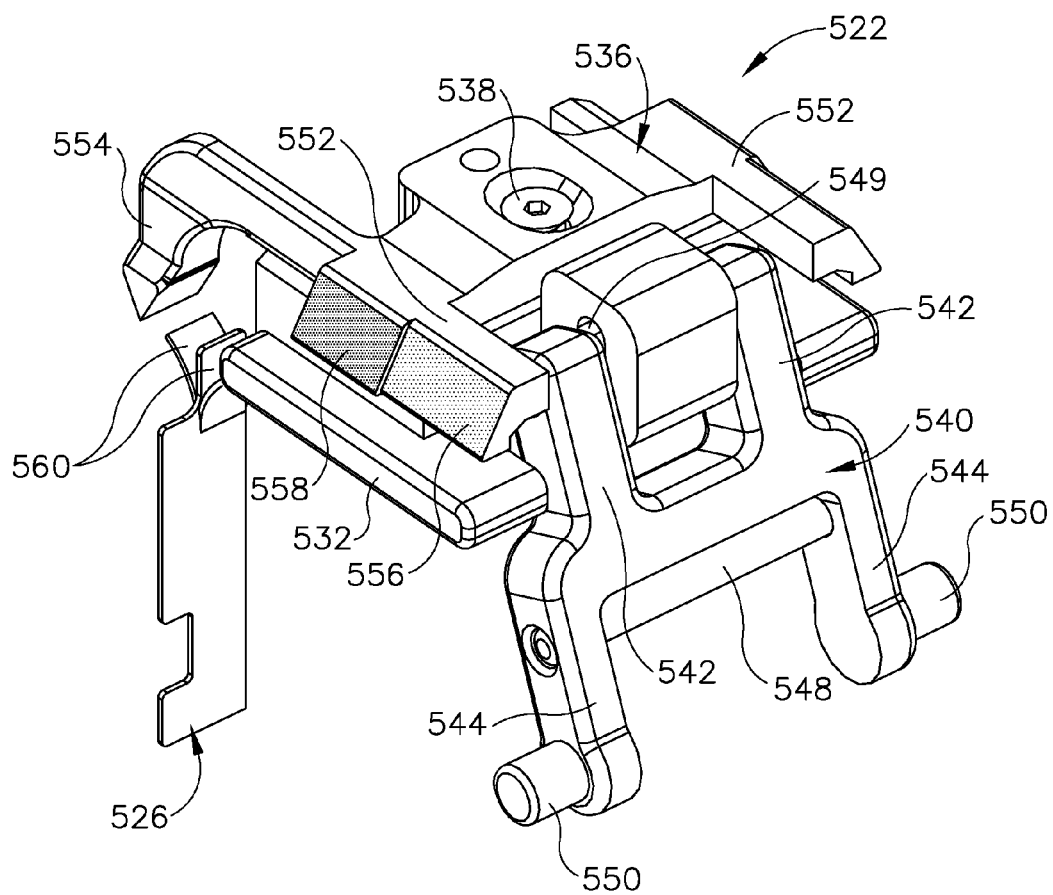
FIG. 20. depicts a left front perspective view of a translational feedback generator of the handle assembly of FIG. 17.
Figure 21:
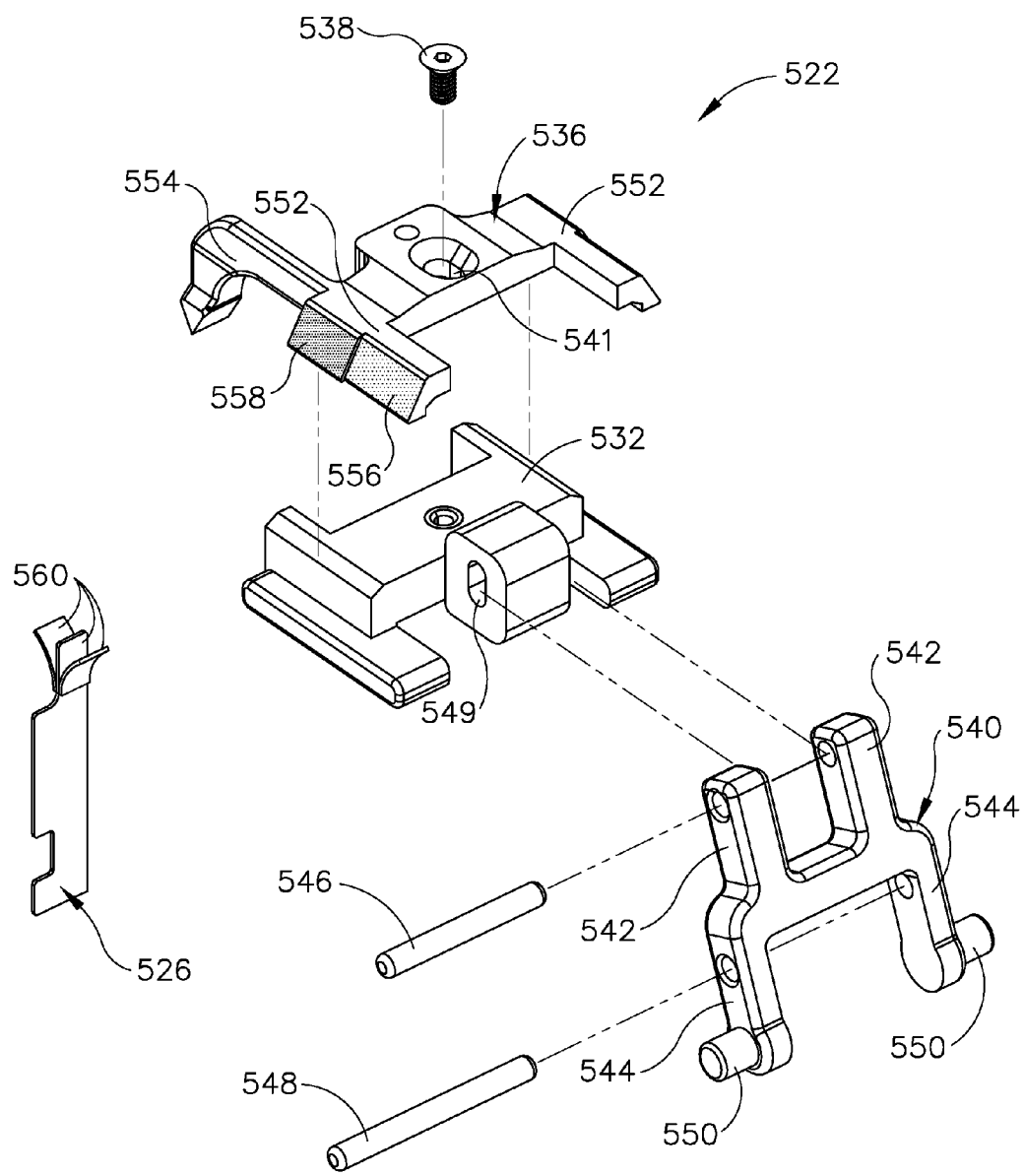
FIG. 21 depicts an exploded left front perspective view of the translational feedback generator of FIG. 20.

Slide feedback assembly (522) and sound generator (526) are shown in greater detail in FIGS. 20 and 21. While sound generator (526) is mounted within handle housing (334) rather than to slide feedback assembly (522), sound generator (526) has been included here for clarity as to the exemplary arrangement of slide feedback assembly (522) relative to sound generator (526). Slide feedback assembly (522) includes sled (532), a feedback member (536) mounted on top of sled (532) via a fastener (538), and a linkage coupling (540). Feedback member (536) and sled (532) are configured to provide for calibration of audible and visual feedback, whereas linkage coupling is configured pull sled (532) with feedback member (536). To this end, feedback member (536) is adjustably mounted to sled (532) via fastener (538) to accommodate manufacturing deviations that may occur in handle and shaft assemblies (312, 314). More particularly, feedback member (536) receives fastener (538) within an elongated hole (541) that extends longitudinally as well as through feedback member (536). Depending on part deviation, the feedback member (536) may be positioned more distally or more proximally relative to sled (532) for calibration such that feedback member (536) communicates the audible and visual feedback at effectively the same approximate time as completion of the firing stroke.

Linkage coupling (540) is generally H-shaped such that an upper portion has an upper pair of legs (542) extending opposite of a pair of lower legs (544). Upper pair of legs (542) has a shortened dowel (546) spanning between each leg (542), whereas lower pair of legs (544) has an elongated dowel (548) spanning between each leg (544). Shortened dowel (546) pivotally connects linkage coupling (540) to sled (532) via a hole (549) in sled (532). In contrast, elongated dowel (546) provides a catch by which to engage firing bar (82) as described with respect to FIGS. 23A-23C below. Each of the lower pair of legs (544) further includes an outwardly extending pivot pin (550) that is configured to be respectively received within mount holes (533) (see FIGS. 17-18) for pivotally mounting linkage coupling (540) to handle housing (334).

Feedback member (536) includes a pair of proximally extending legs (552) and a distally extending, L-shaped pick (554), which projects toward sound generator (526) to pluck sound generator (526) in use. Each of legs (552) aligns with a respective indicia window (524) and includes an unfired indicia (556) adjacent to a fired indicia (558). Unfired indicia (556) and fired indicia (558) may be viewed by the operator through each indicia window (524) as the operator selectively actuates firing bar (83) from the unfired position to the fired position. In addition, sound generator (526) has a plurality of feedback tabs (560) that are cantilevered upwardly and configured to resonate with audible feedback after being plucked by pick (554).

Linkage coupling (540) is further configured to magnify movement of the unfired and fired indicia (556, 558) relative to firing bar (82) for greater resolution when viewed by the operator through indicia window (524) for improved visibility during use. Exemplary linkage coupling (540) is pivotally mounted about pivot pins (550) such that elongated dowel (548) is a shortened radial distance from pivot pins (550) than shortened dowel (546). In other words, pivotal movement about pivot pins (550) results in shortened dowel (546) moving a greater distance than elongated dowel (546). The movement of sled (532), which is directly connected to shortened dowel (546) will thereby be magnified relative to firing bar (82) and handle housing (334). Thus, relatively small manipulations of firing trigger (22) will result in relatively large movement of unfired and fired indicia (556, 558) within indicia window (524) for greater resolution and improved viewing by the operator.

Figure 22:
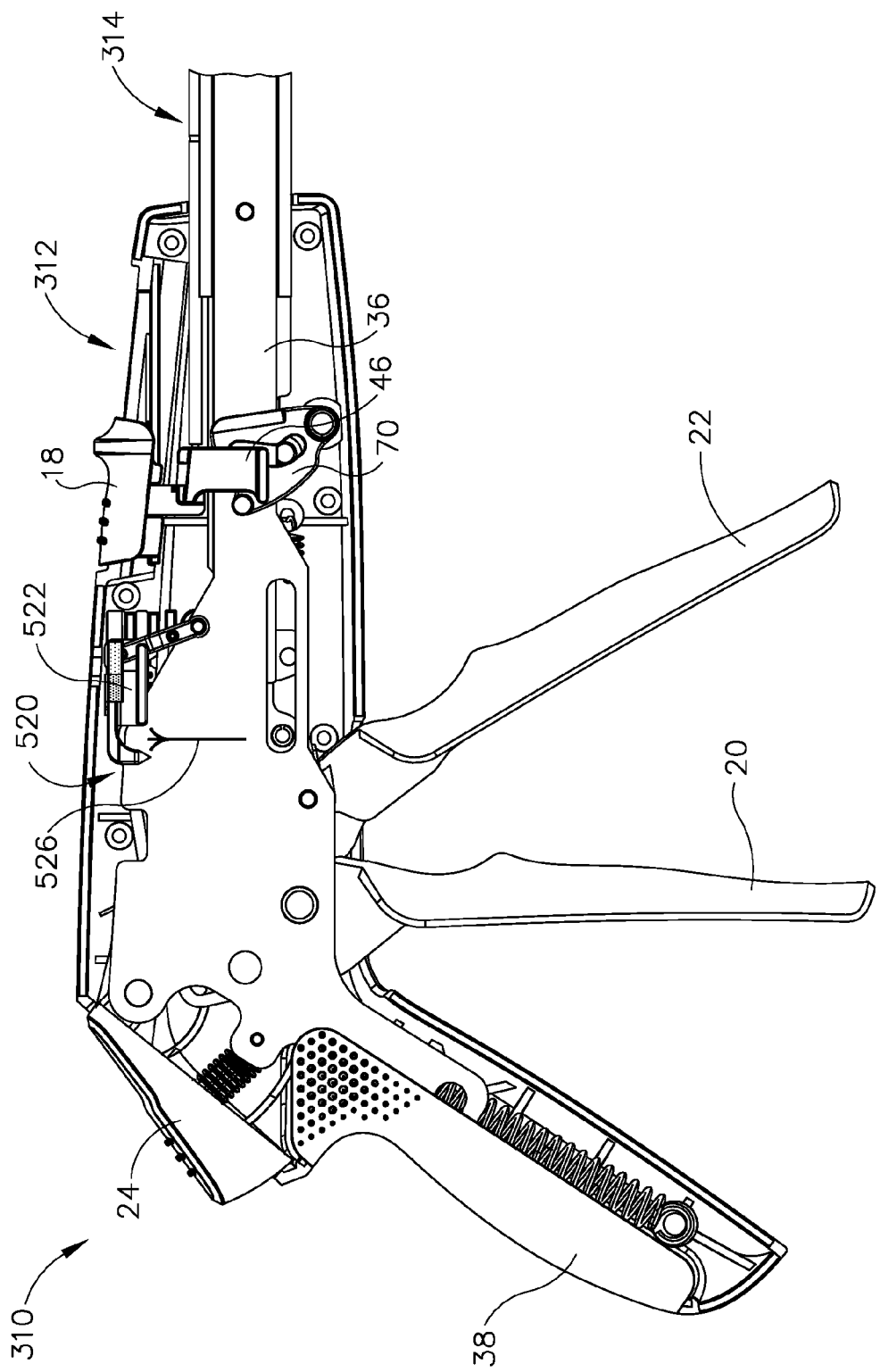
FIG. 22 depicts a left side view of the handle assembly of FIG. 17 with various components removed for clarity.

With respect to FIGS. 22 and 23A, slide feedback assembly (522) is in a relatively distal position within slide channel (530) such that pick (554) is distally positioned from feedback tabs (560) and firing bar (82) is in a relatively distal, unfired position prior to firing bar (82). The operator squeezes firing trigger (22) to simultaneously direct firing bar (82) distally toward the fired position. As firing bar (82) translates distally between lower legs (544), a catch element (562) that extends upwardly from firing bar (82) engages elongated dowel (548) as shown in FIG. 23B. Thereby, firing bar (82) distally pivots linkage coupling (540) about pivot pins (550) such that linkage coupling (540) pulls sled (532) distally along slide channels (530). Sled (532) thus carries feedback member (536) distally as pick (554) plucks feedback tabs (560) to audibly indicate to the operator that firing bar (82) has been fired.

Figure 24A:
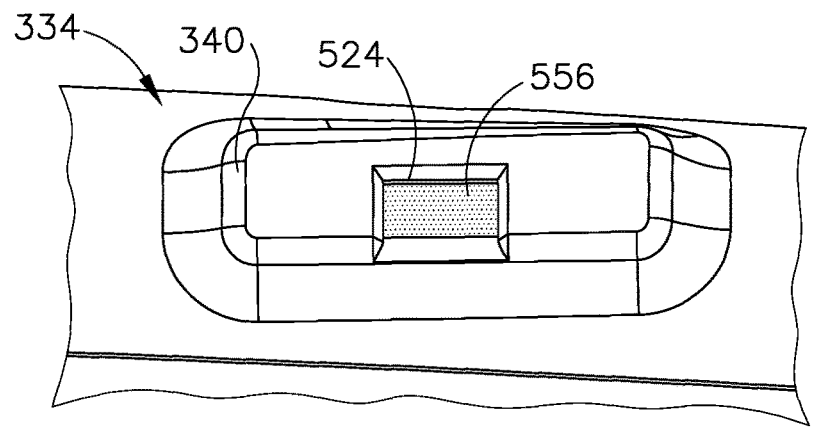
FIG. 24A depicts an enlarged side view of an indicia window of the handle assembly of FIG. 17, with the translational feedback generator in the unfired position.
Figure 24B:
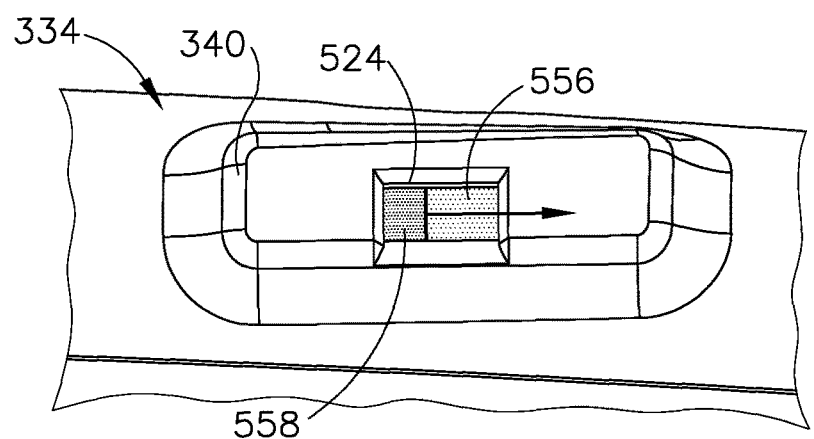
FIG. 24B depicts an enlarged side view of an indicia window of the handle assembly of FIG. 17, with the translational feedback generator moving toward the fired position.
Figure 24C:
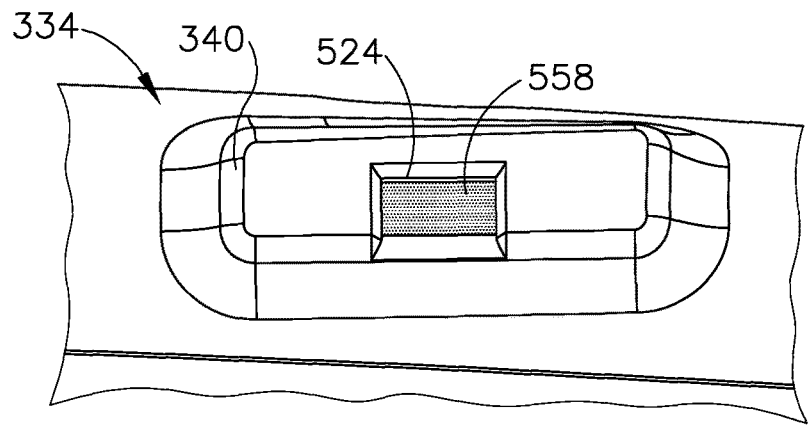
FIG. 24C depicts an enlarged side view of an indicia window of the handle assembly of FIG. 17, with the translational feedback generator in the fired position.

Distal translation of feedback member (536) to indicate firing further translates unfired indicia (556) and fired indicia (558) relative to indicia window (524) as shown in FIGS. 24A-24C. Specifically, FIG. 24A illustrates unfired indicia (556) in alignment with indicia window (524) prior to firing. The operator squeezes firing trigger (22) and, as firing bar (82) fires distally, unfired indicia (556) and fired indicia (558) translate distally as shown in FIG. 24B. Finally, fired indicia (558) aligns with indicia window (524) once firing is complete to indicate to the operator that surgical stapling instrument (310) (see FIG. 11) has been fired.

Figure 25:
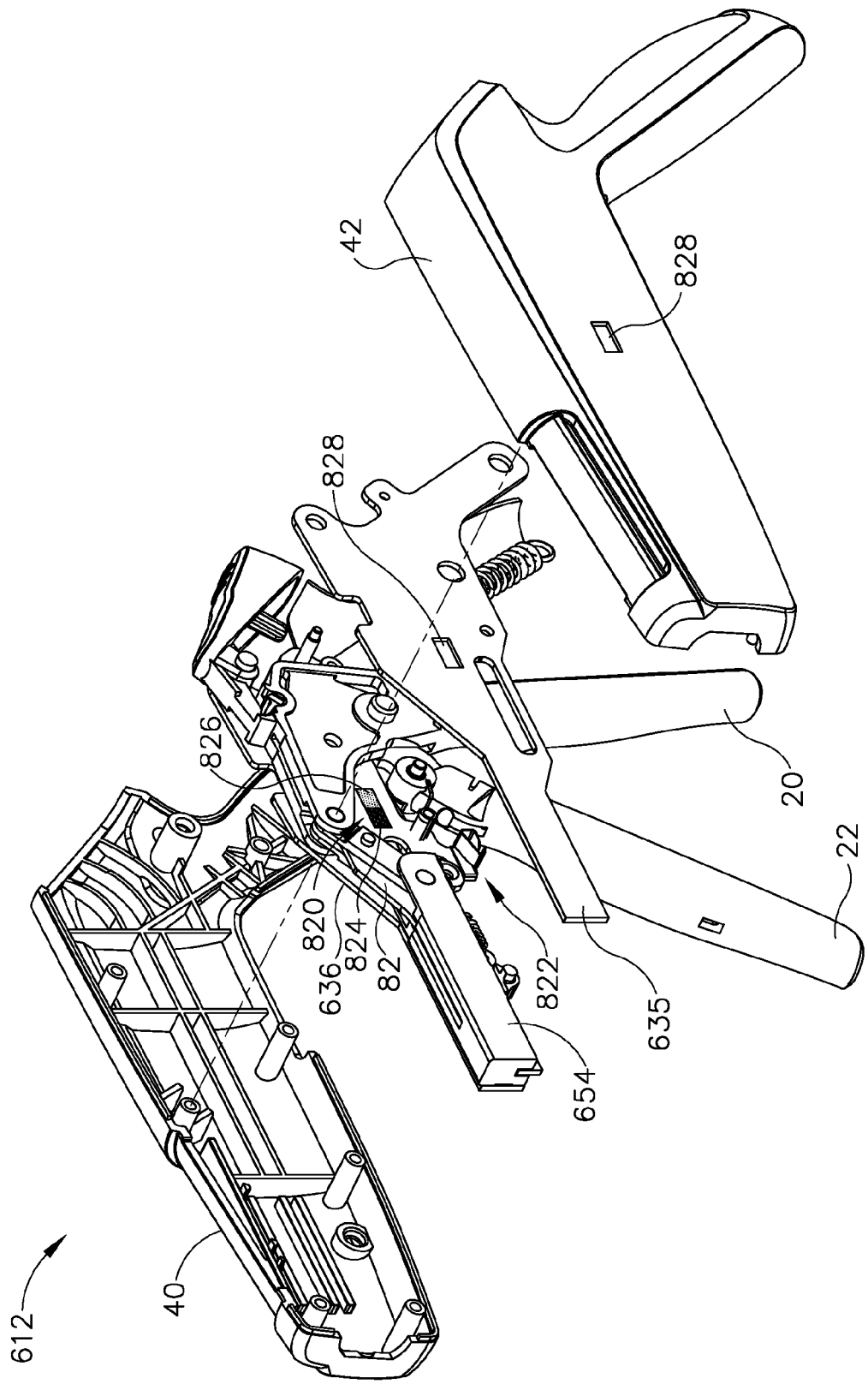
FIG. 25 depicts a partially exploded right front perspective view of a third exemplary handle assembly having a visual feedback generator and an audible feedback generator.

2. Exemplary Translational Visual Feedback Generator and Audible Feedback Generator FIG. 25 shows an exemplary alternative handle assembly (612) that has a visual feedback generator (820) and an audible feedback generator (822). Visual feedback generator (820) includes an unfired indicia (824) positioned distally from and adjacent to a fired indicia (826). Each of unfired indicia (824) and fired indicia (826) are positioned directly on firing bar (82) and move with firing bar (82) to indicate firing to the operator. To enable viewing of indicia (824, 826) on firing bar (82), a pair of indicia windows (828) extend in alignment with indicia (824, 826) through handle frame plate (635) and shroud handle portion (42). Indicia windows (828) align with unfired indicia (824) and fired indicia (826), respectively, in the unfired state such that the operator may view the unfired indicia (824) and fired indicia (826) therethrough. While the particular alignment of indicia (824, 826) and windows (828) may be beneficial for viewing by a right-handed grip of handle assembly (612), it will be appreciated that similar features may be positioned on an opposite side of handle assembly (612) for more easily being viewed by an operator using a left-handed grip.

Figure 27C:
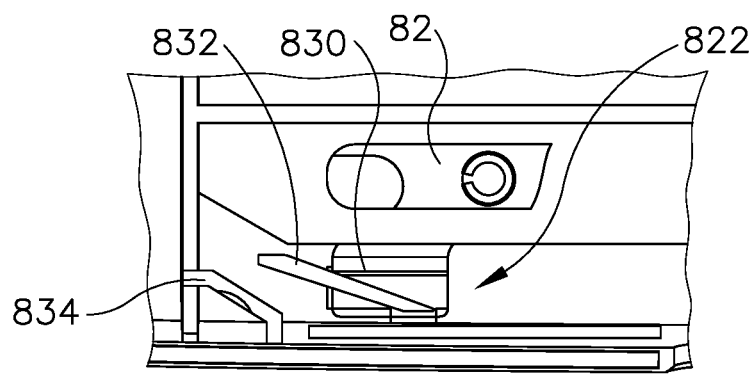
FIG. 27C depicts an enlarged right side view of the audible feedback generator of the handle assembly of FIG. 25, with various components removed for clarity, and with the audible feedback generator moving further toward the fired position.
Figure 27D:
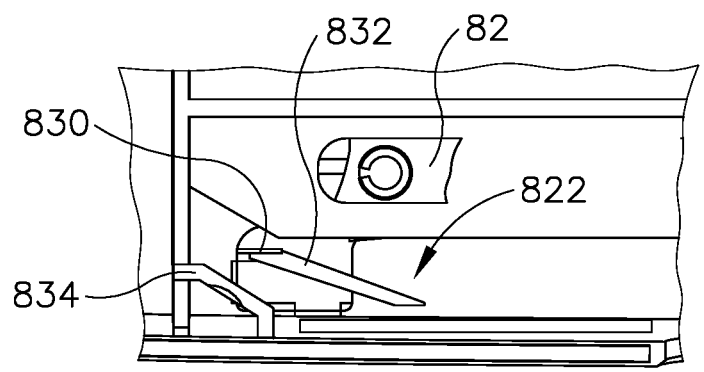
FIG. 27D depicts an enlarged right side view of the audible feedback generator of the handle assembly of FIG. 25, with various components removed for clarity, and with the audible feedback generator moving even further toward the fired position.
Figure 27E:
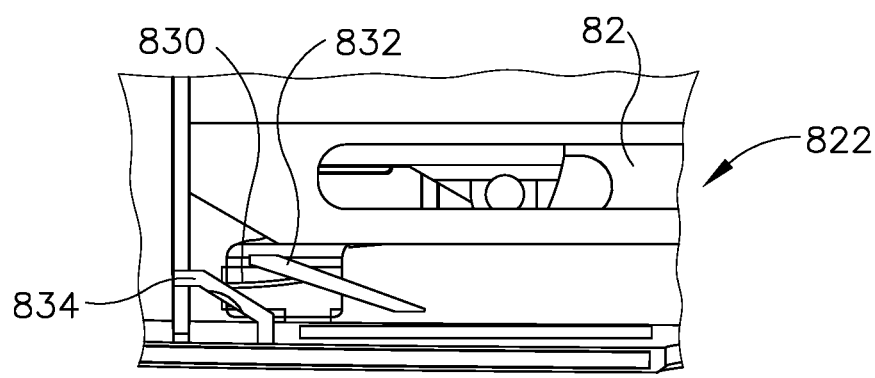
FIG. 27E depicts an enlarged right side view of the audible feedback generator of the handle assembly of FIG. 25, with various components removed for clarity, and with the audible feedback generator in the fired position.
Figure 28A:
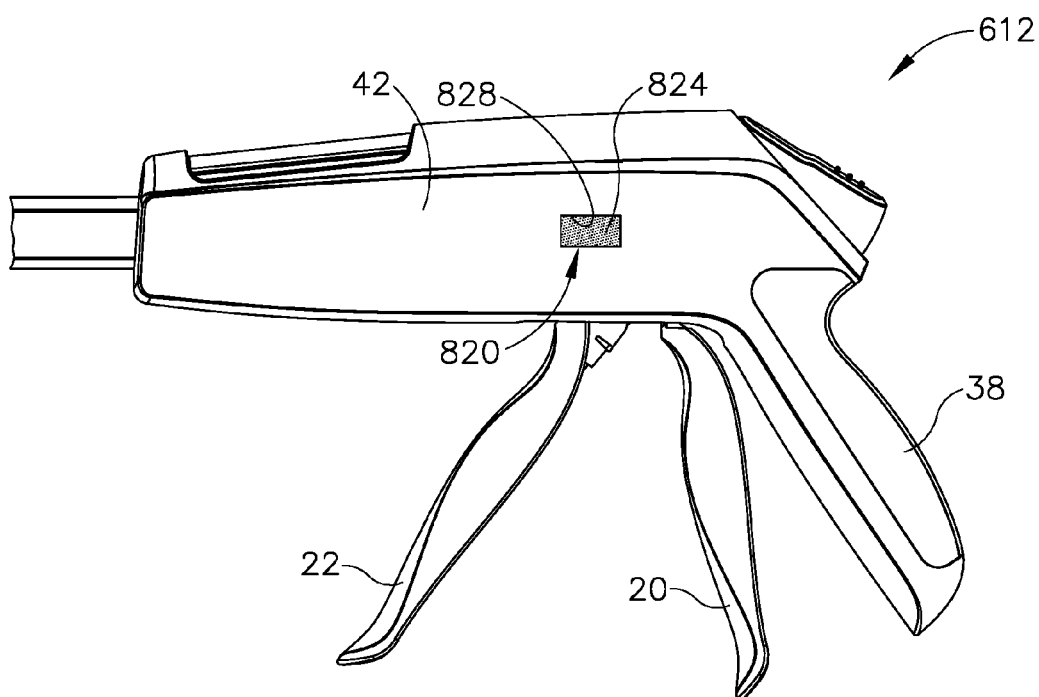
FIG. 28A depicts a side view of the handle assembly of FIG. 25, with the visual feedback generator in the unfired position as viewable through the indicia window of the handle assembly.
Figure 28B:
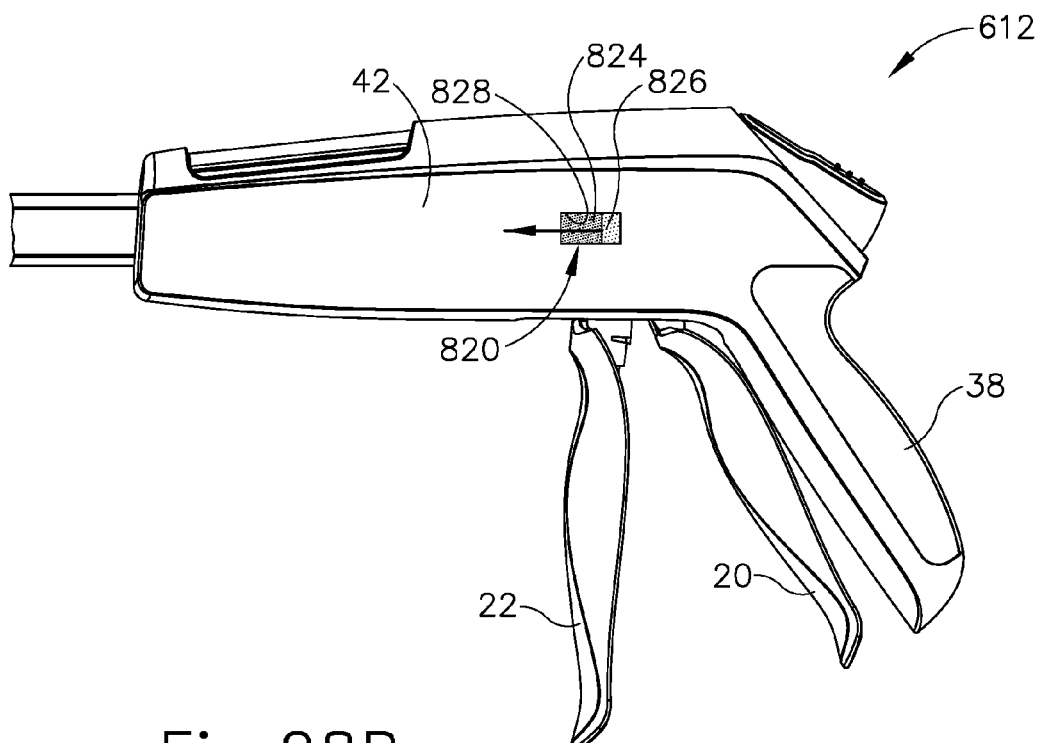
FIG. 28B depicts a side view of the handle assembly of FIG. 25, with the visual feedback generator moving toward the fired position as viewable through the indicia window of the handle assembly.
Figure 28C:
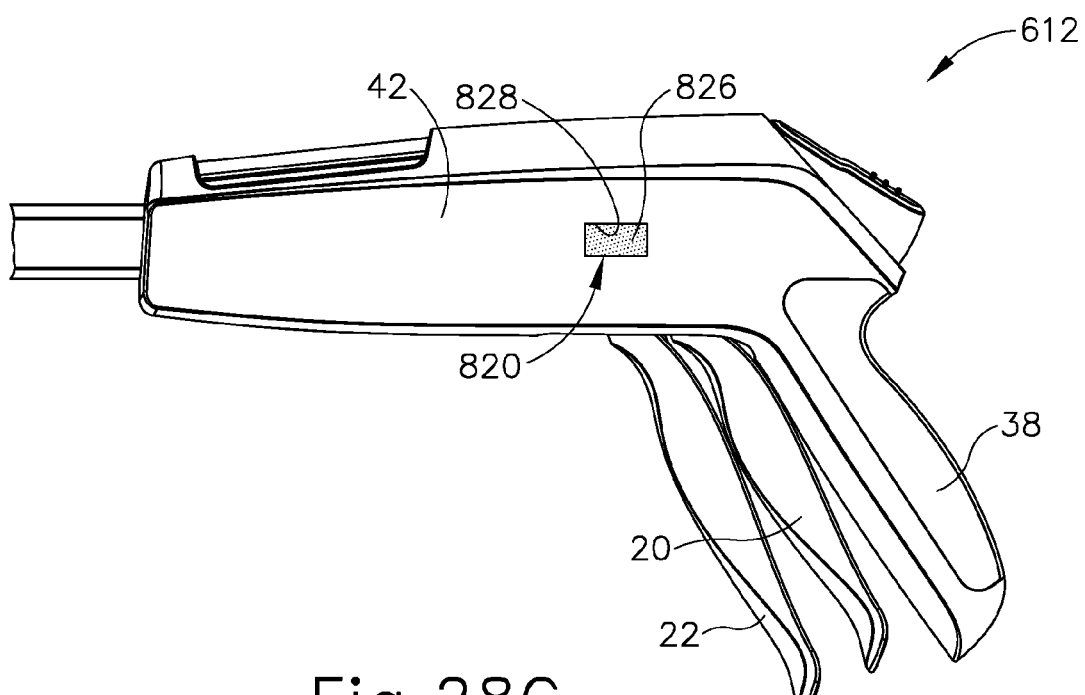
FIG. 28C depicts a side view of the handle assembly of FIG. 25, with the visual feedback generator in the fired position as viewable through the indicia window of the handle assembly.

Audible feedback generator (822) is shown in greater detail in FIGS. 26 and 27A to include a resiliently mounted clip (830) extending from firing bar (82) so as to align with a ramp (832) integrally formed with inner surface of shroud handle portion (42). As shown in succession in FIGS. 27A-27C, firing (actuating) firing bar (82) forces audible feedback generator (822) to translate distally such that clip (830) engages and rises along a top surface of ramp (832). As clip (830) continues to rise along ramp (832), clip (830) is resiliently cocked at top of ramp (832) and continues to be resiliently biased downwardly toward a drum surface (834) in FIG. 27D. Clip (830) continues to translate distally until falling off of ramp (832) and snapping to engage drum surface (834) to generate an audible click. Clip (830) is configured to generate the click as firing bar (82) completes the firing stroke as shown in FIG. 27E. As firing bar (82) moves distally to cock clip (830), unfired indicia (824) and fired indicia (826) move distally as shown in FIGS. 28A-28B. Finally, with firing bar (82) in the fired position, fired indicia (826) is visible to the operator through indicia windows (824) to indicate that the firing bar (82) has effectively been fired during use.

Figure 29:
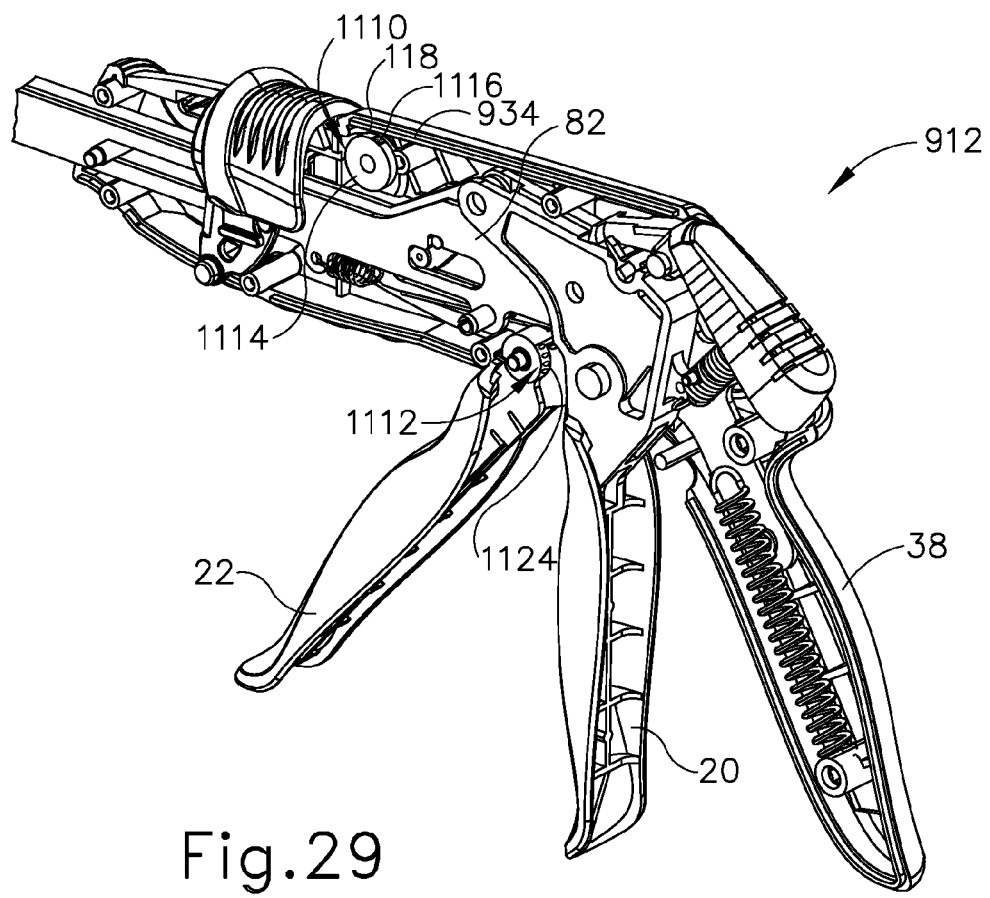
FIG. 29 depicts a rear perspective view of another exemplary handle assembly having a rotational visual feedback generator and a tactile feedback generator with various components removed for clarity.
Figure 30:
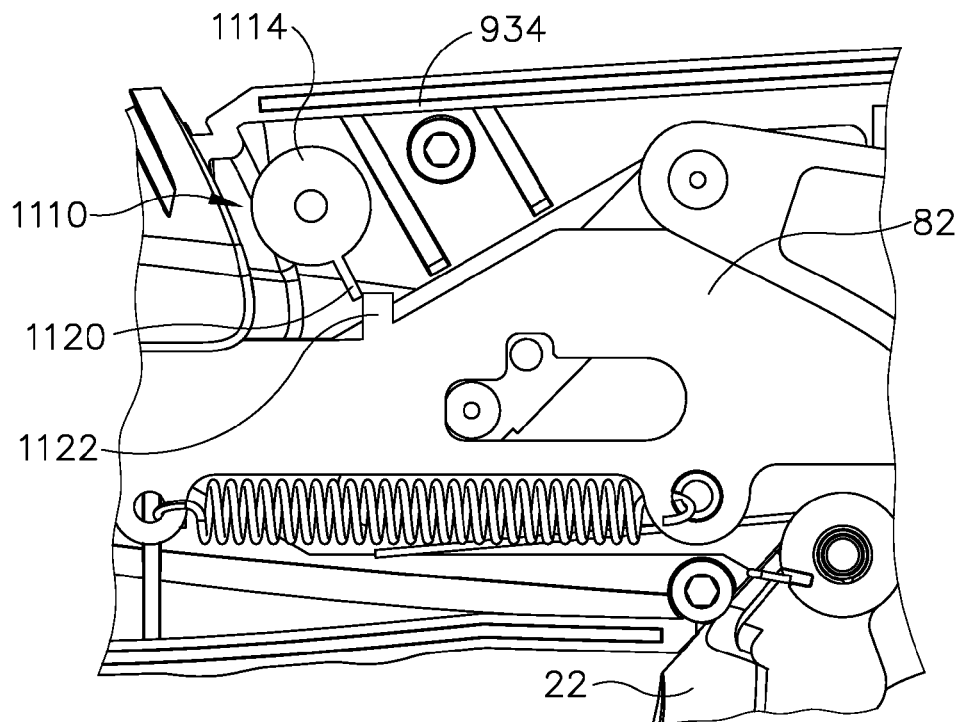
FIG. 30 depicts an enlarged right side view of the rotational visual feedback generator of the handle assembly of FIG. 29.
Figure 31:
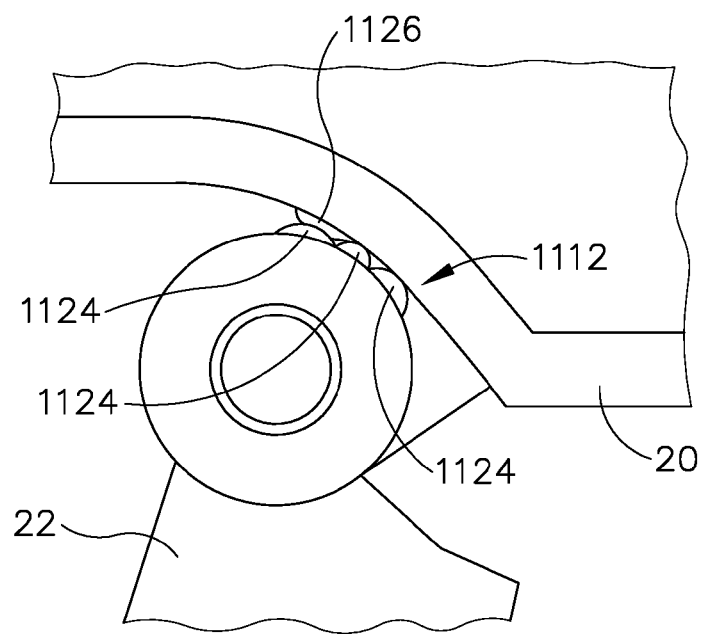
FIG. 31 depicts an enlarged right side view of the tactile feedback generator of the handle assembly of FIG. 29.

3. Exemplary Rotational Visual Feedback Generator and Tactile Feedback Generator FIGS. 29-31 show another exemplary alternative handle assembly (912) that includes a rotational visual feedback generator (1110) and a tactile feedback generator (1112). Rotational visual feedback generator (1110) includes a generally cylindrical wheel (1114) having a peripheral outer surface with an unfired indicia (1116) and a fired indicia (1118). Handle housing (934) includes an indicia window (not shown) adjunct to the peripheral outer surface such that the operator may view the unfired indicia (1116) and fired indicia (1118) during use as discussed above with respect to alternative unfired and fired indicia.

A driven tab (1120) extends radially outwardly from the peripheral outer surface of wheel (1114), whereas a drive tab (1122) extends upwardly from firing bar (82). As shown in FIG. 30, drive tab (1122) is configured to engage driven tab (1120) and rotate wheel (1114) to the fired position and display the fired indicia (1118) through indicia window (not shown) to indicate that firing bar (82) has been fired.

With respect to FIG. 31, tactile feedback generator (1112) includes a plurality of raised bumps (1124, 1126) that rub against each other as firing bar (82) completes the firing stroke. More particularly, closure trigger (20) has at least one raised bump (1126) that is configured to move proximate to firing trigger (22) in the closed configuration. The operator then squeezes firing trigger (22) and the plurality of raised bumps (1124) on firing trigger (22) frictionally rub against the at least one raised bump (1126) to generate a vibration along closure trigger (22). In one example, the plurality of bumps (1124, 1126) is positioned to generate vibration indicative of complete firing of firing bar (82). However, it will be appreciated that the plurality of raised bumps (1124, 1126) may be alternatively positioned on alternative structures to generate tactile feedback indicative of other configurations that may be desirable to the operator.

III. Exemplary Surgical Stapling Instruments with Alternative End Effectors

While the above surgical stapling instrument (10) provides one example of end effector (16) projecting distally from handle assembly (12), it will be appreciated that the operator may desire an alternative end effector depending on one of a variety particular treatments. For example, end effector (16) may be used for stapling and severing colon tissue within the pelvic bowl of the patient, such as in a LAR procedure. While accessing such tissue may be possible with end effector (16), positioning end effector (16) at a specific location to form staples and sever the tissue at a particularly desirable location may be difficult due to limited visibility in this region of the patient; and due to inconsistencies between the geometry of end effector (16) and the geometry of the anatomical structures in the pelvic bowl. The operator may thus position end effector (16) relative to the pelvis, which may be simpler to locate, in order to position end effector (16) in the desirable position relative to the colon. It may therefore be desirable to provide surgical stapling instrument (310) with an end effector (316) that is configured to rest predictably in the bowl of the pelvis for positioning end effector (316) relative to adjacent colon tissue for stapling and severing the tissue with greater accuracy and precision.

Various tissues may be more or less difficult to treat depending on size and/or density within the patient. Despite the operator properly positioning end effector (16) relative to tissue for accurately and precisely stapling and severing the tissue, thicker and/or denser tissues often require added force to be transmitted along surgical stapling instrument (10) and, in turn, may cause one or more components of instrument (10) to deform during use. For example, compressing a portion of the colon between anvil (26) and cartridge (28) in the closed configuration may deform supporting structure (128) of end effector (16), particularly as the tissue is stapled and severed. Thus, the particular location in which the staples form and the knife (32) cuts may vary or deviate a small, but relatively meaningful, amount that may negatively impact the effectiveness of the treatment. It may therefore be desirable to provide surgical stapling instrument (310) with end effector (316) having a supporting structure (328) that is configured to reduce deformation within end effector (316) during treatment. By way of example, end effector (316) may have supporting structure (448) configured to cooperate with one or both of exemplary guide and retaining pins (466, 330) for providing greater structural rigidity during use for reducing deformation within end effector (316); and further increasing the accuracy and precision of the treatment. It may be further desirable to provide an end effector (316, 616, 916, 1216, 1416, 1616) with one of a variety of retaining pins (330, 630, 930, 1230, 1430, 1630) shown and described herein.

While reducing deflection or deformation of end effector (16) by one or more structural modifications may increase accuracy and precision to improve treatment, it will be appreciated that some deflection or deformation may remain or even be desirable in some instances. In turn, rather than reduce deflection or deformation, end effector (16) may be augmented to accommodate such deflection or deformation. For example, staples may be driven to differing depths to correspondingly offset such deflection or deformation such that the staples are arranged more uniformly in the tissue of the patient. Alternatively, staples may be driven non-uniformly to differing depths to accommodate alternative staples of varying size or even to position the staples at varying depths within the patient as determined by the operator. It may therefore be desirable to provide surgical stapling instrument (310) with a staple driver assembly (440, 740, 1040) that is configured to offset deflection or deformation for uniformity; or provide varying desirable staple depths for one of any variety of patterns for non-uniformity, as discussed below.

End effectors (316, 616, 916, 1216, 1416, 1616) are described below in the context of a proctocolectomy surgical procedure. While the following description of end effectors (316, 616, 916, 1216, 1416, 1616) and methods of treatment is provided in the context of stapling and/or cutting colon tissue, it will be appreciated that surgical stapling instrument (310) and any of end effectors (316, 616, 916, 1216, 1416, 1616) may be alternatively configured to treat any tissue in the human body with similar features. It should also be understood that the features discussed below may be readily incorporated into surgical stapling instrument (10) discussed above. To this end, like numbers indicate like features described above in greater detail.

A. Exemplary End Effector with Arcuate Distal Surface

FIG. 32 shows exemplary end effector (316) extending distally from shaft assembly (314) of surgical stapling instrument (310) as shown in FIGS. 11-12. With respect to FIG. 32, end effector (316) includes a distal end portion (564) that is configured to cooperatively engage the pelvic bowl such that cartridge (328) and anvil (26) align in a predetermined orientation with respect to the colon in to receive the colon and perform a lower anterior resection (LAR) of the colon. Distal end portion (564) more particularly includes a C-shaped profile as viewed in FIG. 33 having an arcuate distal surface (566) extending continuously from transverse ends, such as a lower half-dome (567) to an upper half dome (568). The C-shaped profile of exemplary end effector (316) has an inner radius of curvature between approximately 1.0 inch and approximately 1.2 inches and an outer radius of curvature of between approximately 1.3 inches and approximately 1.6 inches. More particularly, the inner radius of curvature is approximately 1.1 inches, and the outer radius of curvature is approximately 1.5 inches. Arcuate distal surface (566) defines a distal crest (569) that is laterally offset from lower and upper half-domes (567, 568), as shown in FIG. 33. With respect to FIGS. 34-35, distal crest (569) is approximately midway between lower and upper half-domes (567, 568) in a transverse direction and is distally offset from lower and upper half-domes (567, 568) with a radius of curvature shown in FIG. 35 between half-domes (567, 568) that is between approximately 1.5 inches and approximately 3.0 inches. More particularly, the radius of curvature of distal crest (569) is approximately 2.0 inches. The exemplary curvature between half-domes (567, 568), which includes distal crest (569), is a compound curvature. To this end, the radius of curvature of distal crest (569) transitions to the curvatures of half-domes (567, 568) allowing distal end portion (564) to be flatter, such as the radius of curvature of distal crest (569) being approximately 3.0 inches, or more pointed, such as the radius of curvature of distal crest (569) being approximately 1.5 inches.

As noted above, arcuate distal surface (566) is generally continuous and smooth for fitting stably in the pelvic bowl as the operator applies force against the pelvic bowl with the arcuate distal surface (566). FIGS. 36-38 illustrate transverse cross-sections taken from the inner radius to the outer radius adjacent to the lower half-dome (567), through distal crest (569), and adjacent to upper half-dome (568), respectively. In each instance shown, arcuate distal surface (566) has a generally equivalent transverse profile. While arcuate distal surface (566) of end effector (316) is particularly keyed to be received against the pelvic bowl for performing the lower anterior resection (LAR), it will be appreciated that various alternative crests, curves, and shapes may be desirable for alternatively locating end effector (316) relative to the colon or other anatomical structures. Thus, the surgical stapling instrument (310) is not intended to be unnecessarily limited to arcuate distal surface (566) and may be configured for alternative treatments and/or alternative tissues.

B. Exemplary End Effector with Structural Guide Pin

Figure 39:
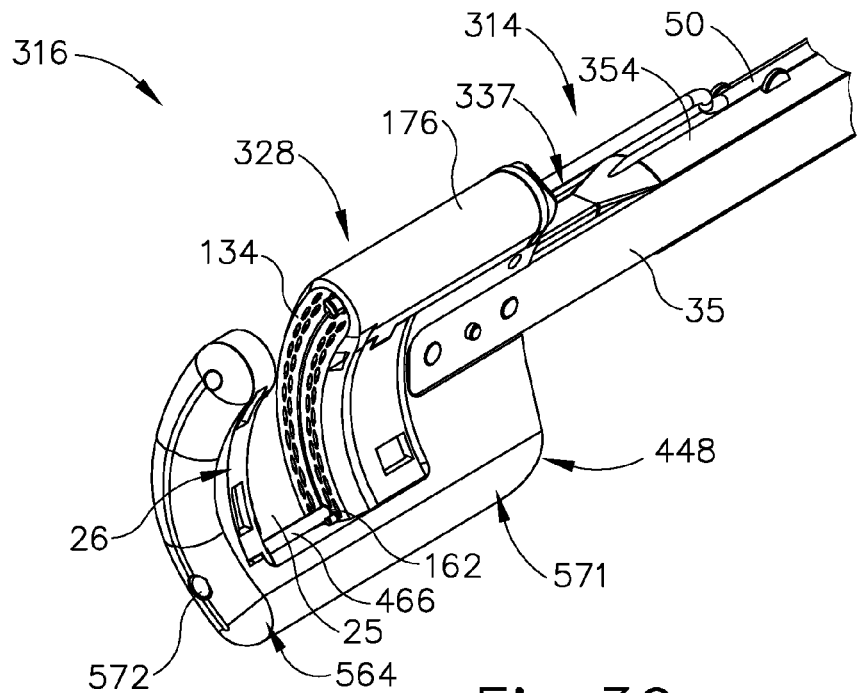
FIG. 39 depicts a front right perspective view of an exemplary end effector with a structural pin assembly.
Figure 40:
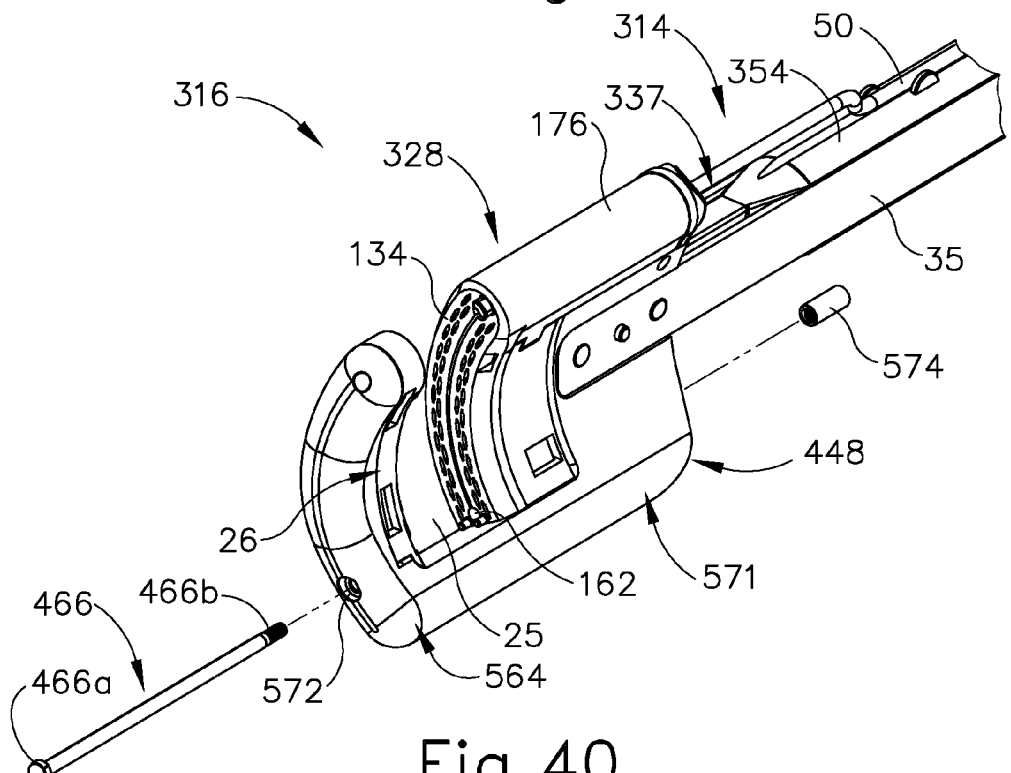
FIG. 40 depicts a partially exploded front right perspective view of the end effector of FIG. 39.
Figure 41:
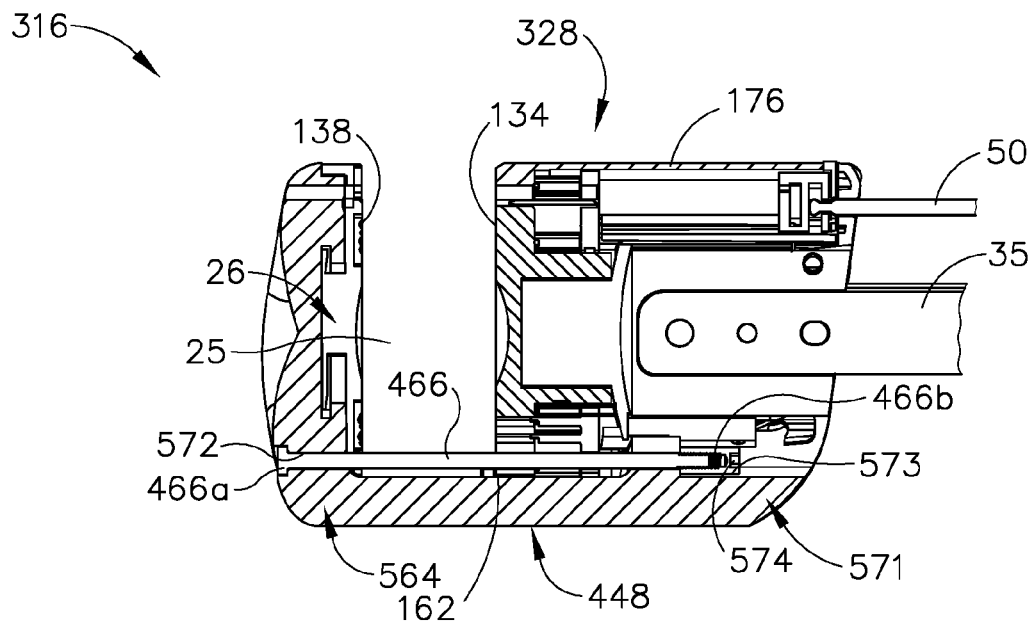
FIG. 41 depicts a cross-sectional view of the end effector of FIG. 39, taken along a centerline of the structural pin assembly.

As shown in FIGS. 39-41, end effector (316) has a structural guide pin (466) configured to receive tissue thereagainst for inhibiting lateral positioning of tissue beyond cartridge (28) and anvil (26) and guide movement of cartridge (332) from the closed configuration toward the open configuration as discussed above. In addition, structural guide pin (466) also rigidifies distal end portion (564), which receives anvil (26). Structural guide pin (446) extends through hole (162) in cartridge (328) and is configured to guide longitudinal movement of cartridge (328) between distal and proximal positions as discussed above in greater detail with respect to surgical stapling instrument (10) (see FIGS. 1A-1D). In addition, structural guide pin (466) extends from distal end portion (564) of supporting structure (448) and into a proximal end portion (571) to traverse the opening between anvil (26) and cartridge (328), providing structural rigidity therealong to inhibit distal end portion (564) from deflecting relative to proximal end portion (571) during treatment.

As shown in FIGS. 40 and 41, structural guide pin (466) of the present example is in the form of a threaded fastener having a distal head end (466a) and a proximal threaded end (466b). Supporting structure (448) has a distal pin bore (572)

positioned offset from a proximal pin bore (573) such that distal and proximal pin bores (572, 573) receive structural guide pin (466) from the distal direction. Distal pin bore (572) is thus configured such that distal head end (466a) seats therein; whereas proximal pin bore (572) receives a threaded nut (574) seated opposite the distal head end (466a). Proximal threaded end (466b) rotatably threads into threaded nut (574) such that structural guide pin (466) is held in tension between pin bores (572, 573) as shown in FIG. 41.

In use, structural guide pin (466) receives tissue thereagainst and guides cartridge (328) between open and closed configurations as discussed above and shown in FIGS. 1A and 1C, respectively. In addition, structural guide pin (466) braces supporting structure (448) in tension between distal and proximal end portions (564, 571) as tissue is compressed between anvil (26) and cartridge (328). In other words, structural guide pin (466) rigidifies supporting structure (448) to inhibit distal end portion (564) from deflecting relative to proximal end portion (571) of end effector (316). For example, structural guide pin (466) also inhibits distal end portion (564) from deflecting relative to proximal end portion (571) as staples are pressed into staple-forming surface (138) of anvil (26) from cartridge (328) for improved accuracy and precision of staple formation and tissue severing.

C. Exemplary Surgical Stapling Instrument with Lockable Retaining Pin Mechanism

Figure 42:
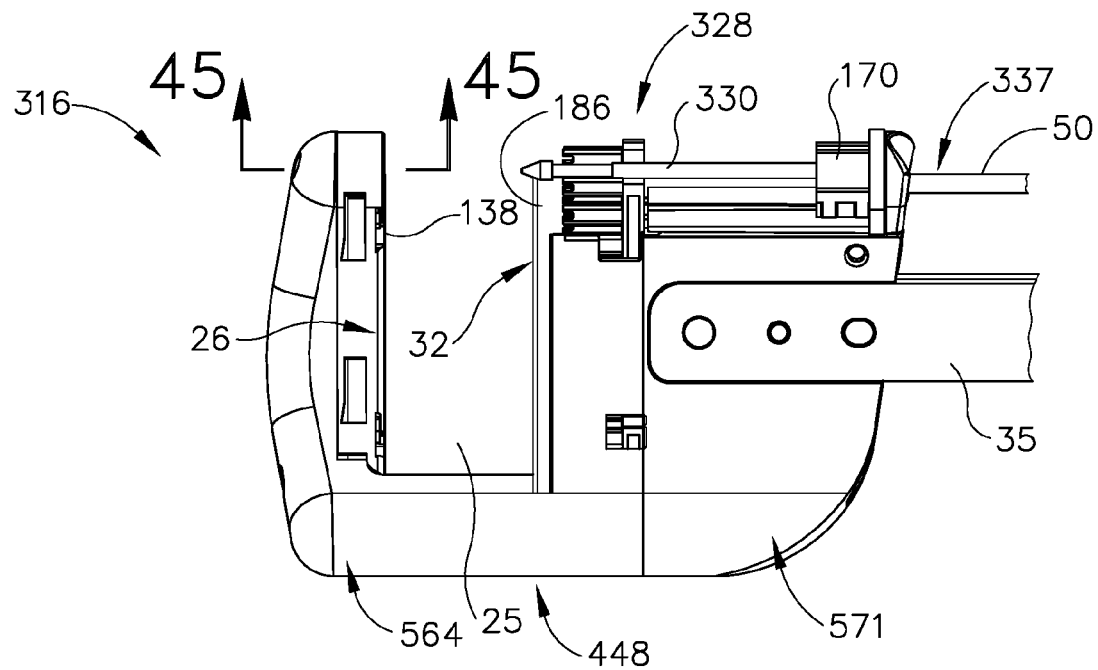
FIG. 42 depicts a right side view of the end effector of FIG. 32 having various components removed for clarity.
Figure 43:
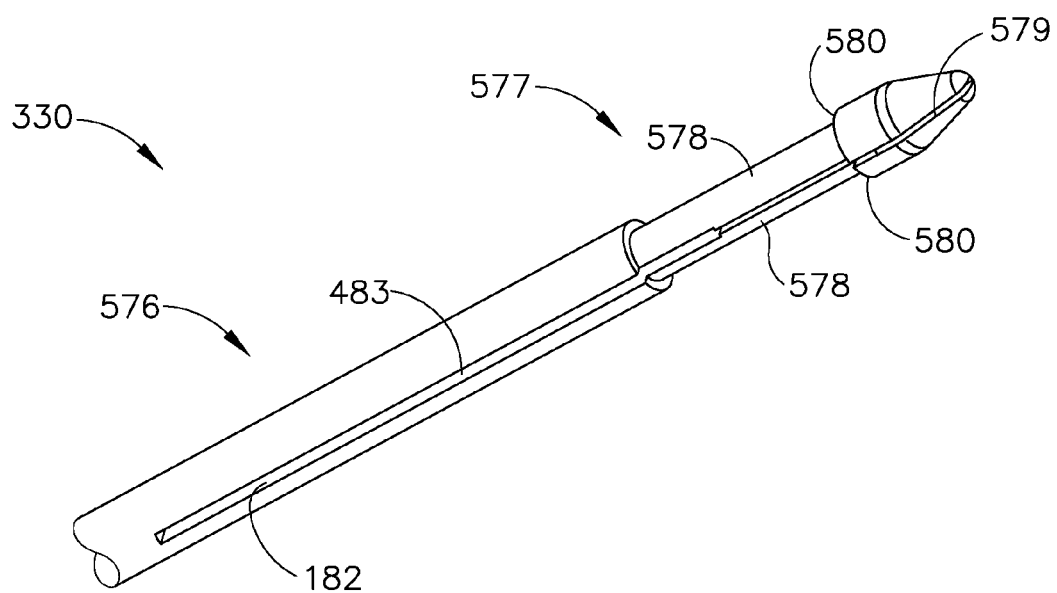
FIG. 43 depicts a lower perspective view of a retaining pin of the end effector of FIG. 32.
Figure 44:
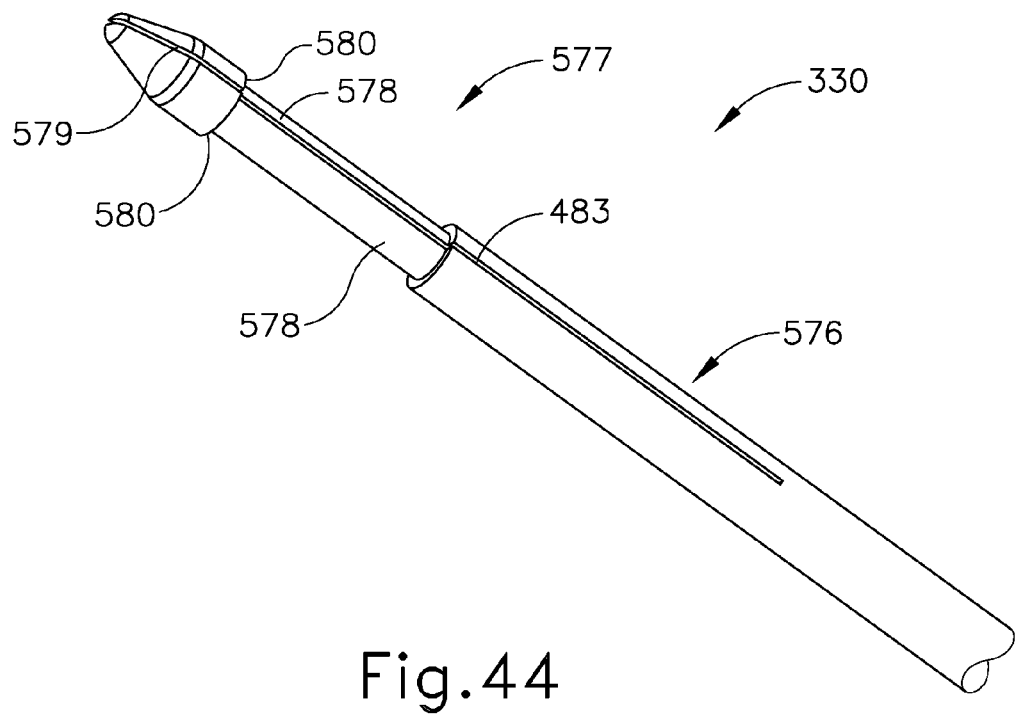
FIG. 44 depicts an upper perspective view of the retaining pin of FIG. 43.
Figure 45:
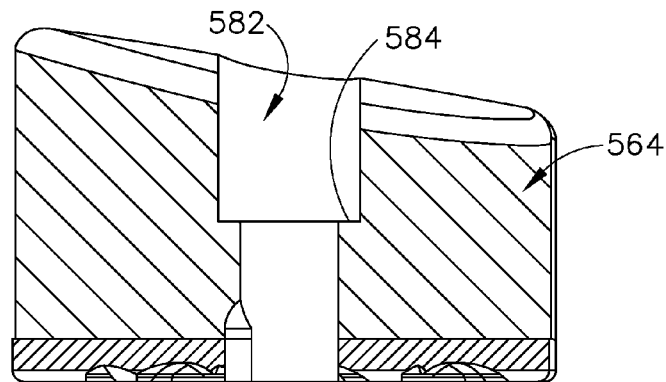
FIG. 45 depicts a cross-sectional view of the end effector of FIG. 32, taken along section line 45-45 of FIG. 42.
Figure 46:
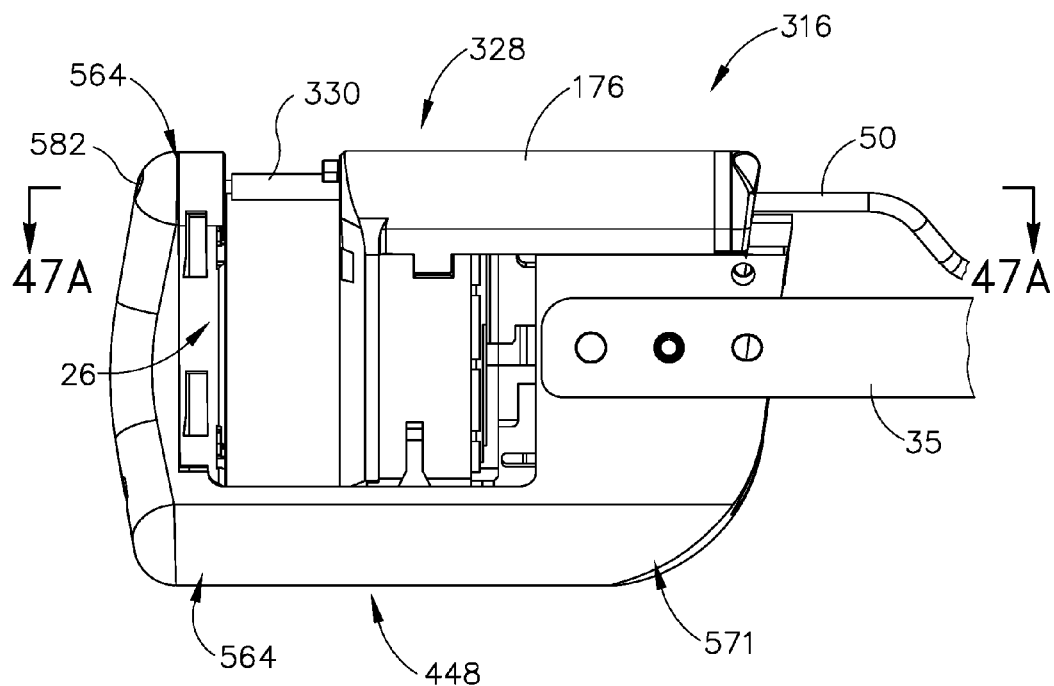
FIG. 46 depicts a right side view of the end effector of FIG. 32, with the retaining pin in an unlocked closed position.

A lock retaining pin (330) is configured to translate from an open position to a locked closed position as shown in FIGS. 42-47C. FIG. 42 shows end effector (316) with cartridge (328) loaded therein in the open configuration for receiving tissue within gap (25) as discussed above in greater detail. Cartridge (328) has a retaining pin mechanism (337), which includes lock retaining pin (330) connected to push rod (50) via couplet (170). Slide (18) (see FIG. 1A and FIG. 2A) selectively directs movement of push rod (50) distally from the open configuration to the closed configuration for capturing tissue, such as colon tissue for performing a lower anterior resection (LAR). To this end, lock retaining pin (330) is generally driven distally from within arm (176) of cartridge (328) to distal end portion (564) similar to retaining pin (30) discussed above in greater detail with respect to FIGS. 1A-1B and FIGS. 7A-7B. However, it will be appreciated that alternative mechanisms for moving lock retaining pin (330), such as by rotation and/or translation, may be used in accordance with principles discussed herein.

1. Exemplary Knife Lock Retaining Pin and Ledge Lock

Figure 47A:
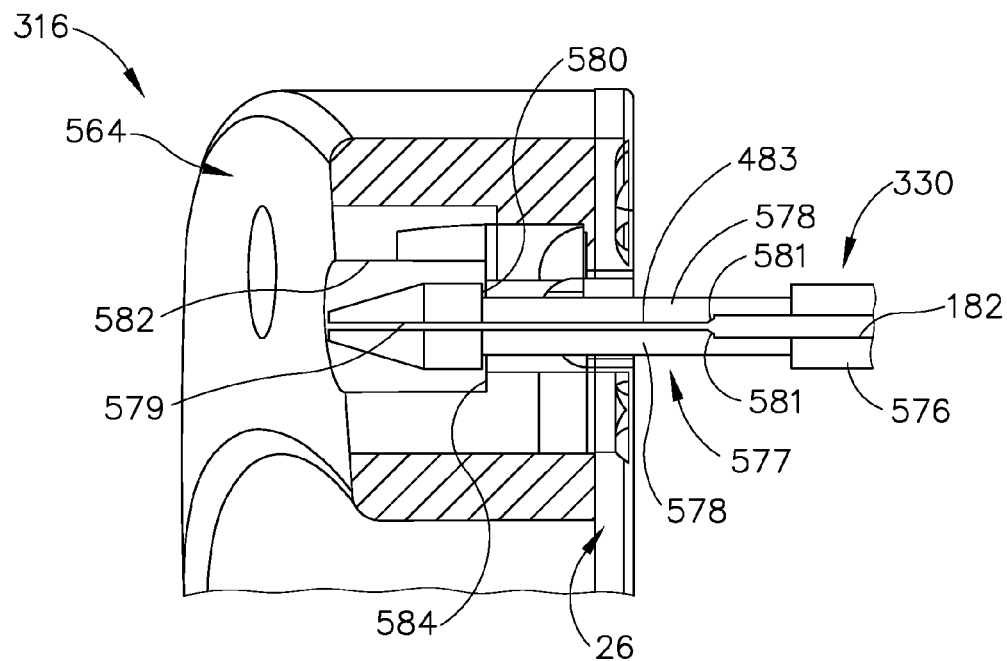
FIG. 47A depicts a cross-sectional view of a portion of the end effector of FIG. 32, with the retaining pin in the unlocked closed position of FIG. 46, taken along section line 47A-47A of FIG. 46.

Knife lock retaining pin (330) extends through arm (176) (see FIG. 6) of cartridge (328) in the open configuration shown in FIG. 42. Cartridge housing (132) (see FIG. 6) has been removed for clarity and improved visibility of knife lock retaining pin (330). With respect to FIGS. 42-44, knife lock retaining pin (330) includes longitudinally extending slot (182) through which knife lock retaining pin (330) receives and guides upper lateral end (186) of knife (32) between closed and open configurations. Slot (182) extends transversely through a portion of knife lock retaining pin (330) such that slot (182) does not extend entirely transversely therethrough. Knife lock retaining pin (330) further includes an expansion slot (483), generally thinner than slot (182), that extends longitudinally from an intermediate pin portion (576) of knife lock retaining pin (330) through a distal end portion (577) of knife lock retaining pin (330). Expansion slot (483) extends entirely transversely through knife retaining pin (330) in one example from intermediate pin portion (576) through distal end portion (577) in order to bisect distal end portion (577) into two resilient extensions (578). Each resilient extension (578) of distal end portion (577) is annularly recessed to define a distal head (579) having a proximal annular ledge (580). As shown in FIG. 47A, extension slot (483) longitudinally intersects slot (182) to define offset shoulders (581) within distal end portion (577) on each respective resilient extension (578). Knife (32) has a transverse depth (see FIG. 47B) greater than expansion slot (483) such that knife (32) moving distally through slot (182) is configured to engage shoulders (581) and wedge between resilient extensions (578) away from knife (32). Thereby distal head (483) resiliently expands from a contracted state to an expanded state.

With further respect to FIG. 47A, distal end portion (564) of end effector (316) includes a longitudinally extending retaining pin bore (582) that is configured to receive distal head (579) of knife lock retaining pin (330) in the contracted state. Retaining pin bore (582) has a distal portion with a larger diameter to define a distal annular ledge (584). Distal annular ledge (584) is sized such that the lower portion of retaining pin bore (582) is smaller in diameter than distal head (579) in the expanded state. Thus, in the expanded state, proximal annular ledge (580) of distal head (579) overlaps with distal annular ledge (584) within retaining pin bore (582) to inhibit deflection of distal end portion (564) of end effector (316) relative to knife lock retaining pin (330). In other words, expansion of distal head (579) within retaining pin bore (582) positions knife lock retaining pin (330) in the locked closed position.

Figure 47B:
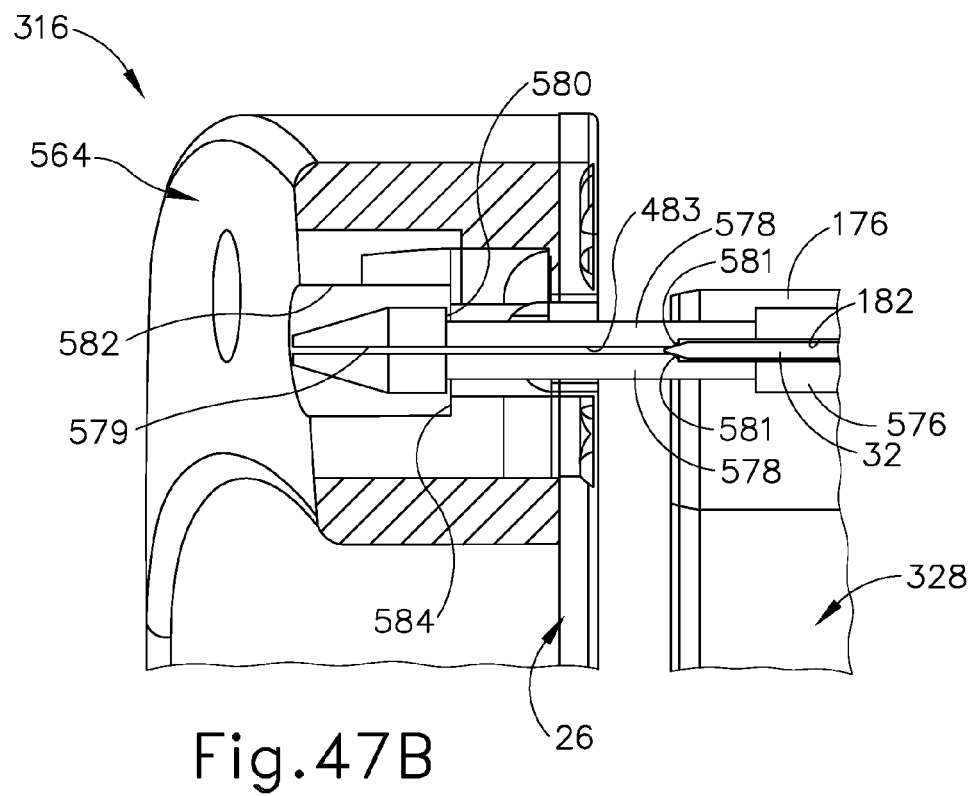
FIG. 47B depicts a cross-sectional view of a portion of the end effector of FIG. 32, with the staple cartridge moving toward the closed position.
Figure 47C:
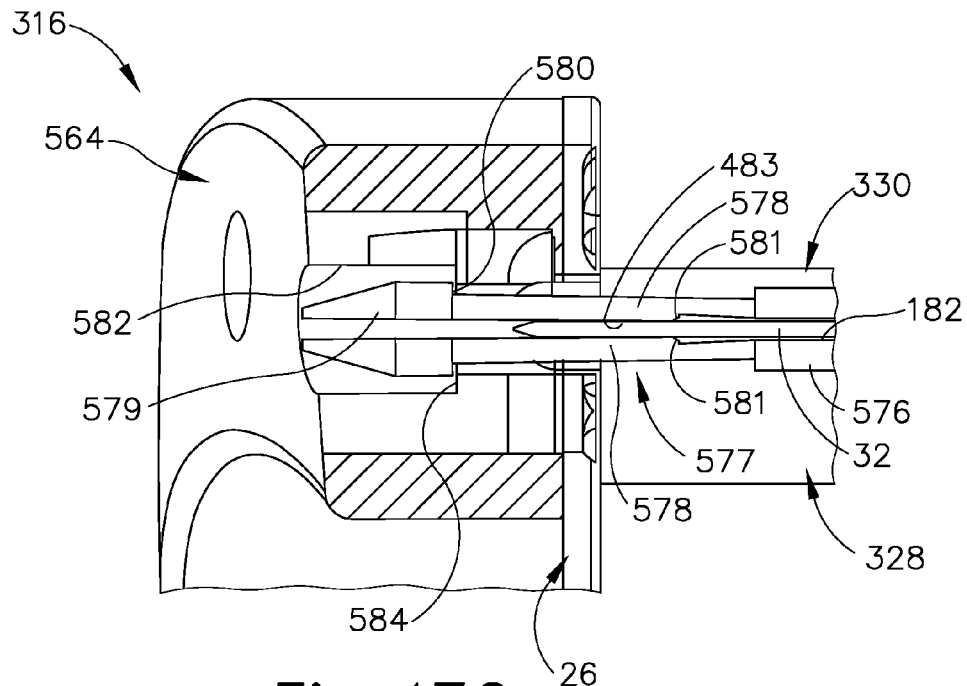
FIG. 47C depicts a cross-sectional view of a portion of the end effector of FIG. 32, with the retaining pin in a locked closed position.

FIGS. 47A-47C illustrate knife lock guide pin (330) locking from an unlocked closed position to the locked closed position. FIG. 47A shows knife lock guide pin (330) in the unlocked closed position following distal movement directed by slide (18) (see FIG. 1A and FIG. 2A) of retaining pin actuation mechanism (337). With tissue (not shown) captured between cartridge (328) and anvil (26), cartridge (328) and knife (32) contained therein are directed toward distal end portion (564) of end effector (316). Knife (32) continues distally such that knife (32) engages shoulders (581) to wedge between resilient extensions (578) and expand distal head (579) outwardly from the contracted state to the expanded state. Thereby, distal head (579) is effectively captured in distal portion of retaining pin bore (582) as shown in FIG. 47C. Distal annular ledge (584) of retaining pin bore (582) may then engage proximal annular ledge (580) of knife lock retaining pin (330) to inhibit deflection of distal end portion (564) of end effector (316) as cartridge (328) and tissue are compressed against anvil (26). While knife lock guide pin (330) is expanded via knife (32) in the present example and effectively braces distal end portion (564) in tension, it will be appreciated that alternative structures may expand alternative guide pins; or may otherwise lock with distal end portion (564) such that alternative guide pins may brace distal end portion (564) in compression, as well. To this end, the invention described herein is not intended to be unnecessarily limited to exemplary knife lock guide pin (330).

2. Exemplary Rod lock Retaining Pin and Ledge Lock

Figure 48:
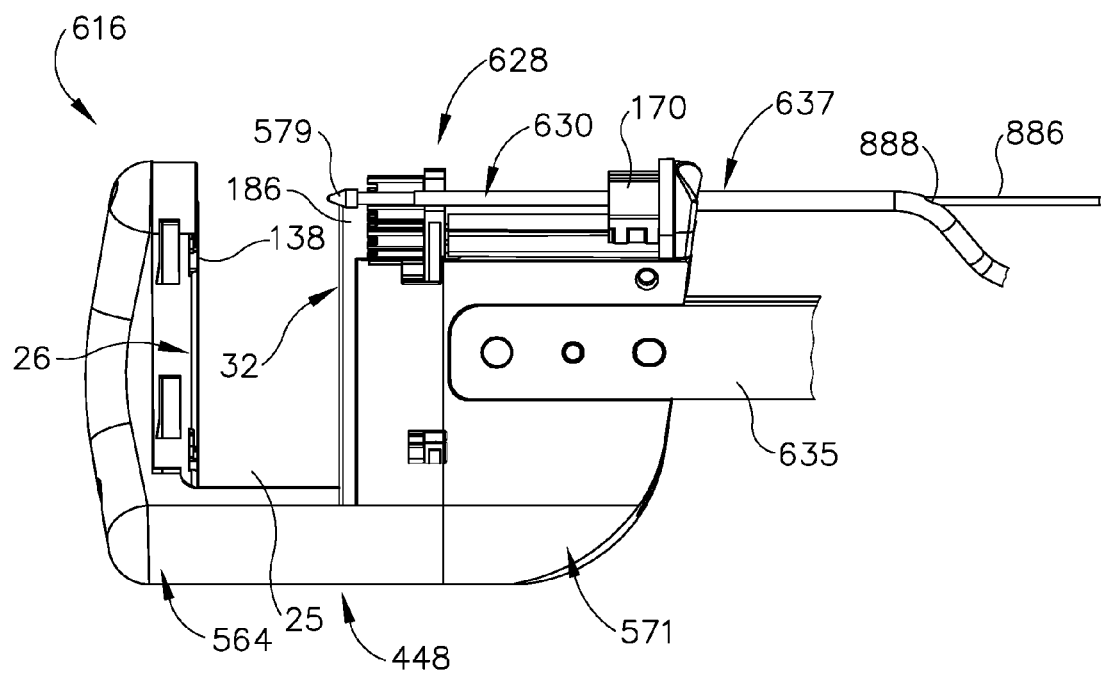
FIG. 48 depicts a right side view of another exemplary end effector having various component removed for clarity.
Figure 49:
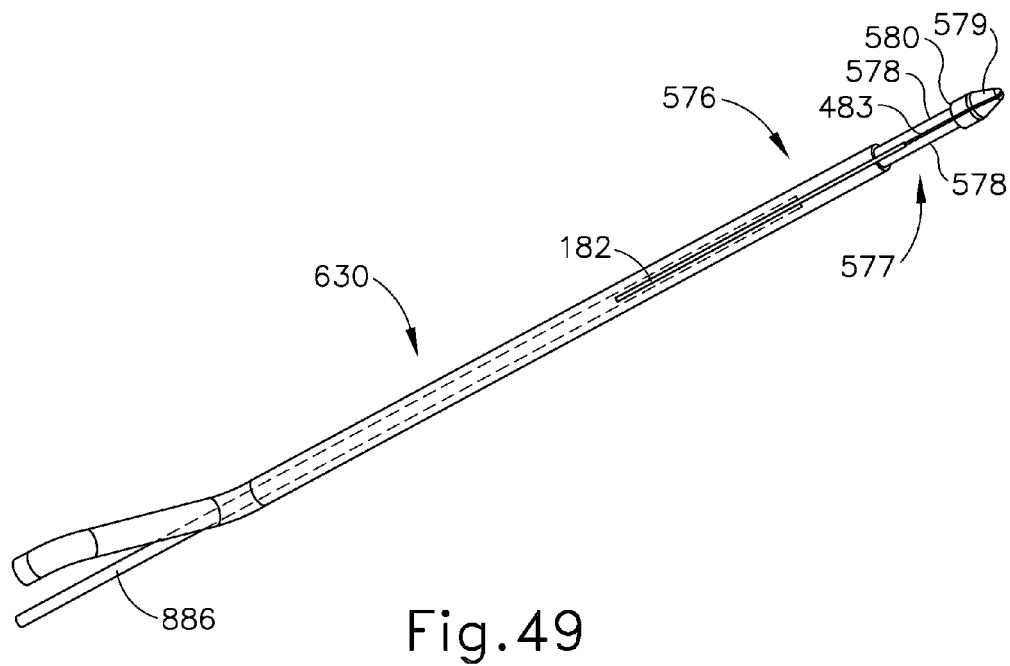
FIG. 49 depicts a lower perspective view of a retaining pin of the end effector of FIG. 48.
Figure 50:
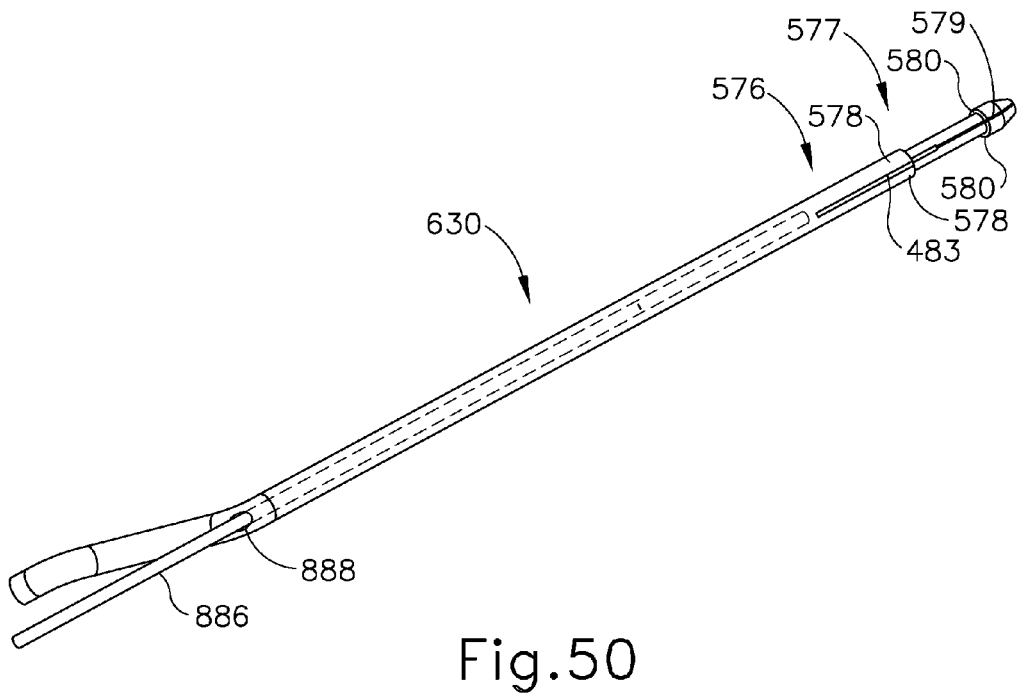
FIG. 50 depicts an upper perspective view of the retaining pin of FIG. 49.

FIG. 48 shows an exemplary alternative end effector (616), where a rod lock retaining pin (630) extends through arm (176) (see FIG. 6) of a cartridge (628) in the open configuration. Cartridge housing (132) (see FIG. 6) has been removed for clarity and improved visibility of rod lock retaining pin (630). As shown in FIGS. 48-50, rod lock retaining pin (630) includes longitudinally extending slot (182) through which rod lock retaining pin (630) receives and guides upper lateral end (186) of knife (32) between closed and open configurations. Slot (182) extends transversely through a portion of rod lock retaining pin (630) such that slot (182) does not extend entirely transversely therethrough. Rod lock retaining pin (630) further includes expansion slot (483), which is generally thinner than slot (182), that extends longitudinally from an intermediate pin portion (576) of rod lock retaining pin (630) through distal end portion (577) of rod lock retaining pin (630) as discussed above with two resilient extensions (578) and distal head (579).

A retaining pin actuation mechanism (637) further includes a closure rod (886) that is configured to translatably extend through rod lock retaining pin (630) to selectively direct distal head (579) between contracted and expanded states independent of the position of knife (32). Rod lock retaining pin (630) includes an elongate aperture (888) that extends coaxially through rod lock retaining pin (630), which is configured to receive closure rod (886) such that closure rod (886) may slide longitudinally back and forth within rod lock retaining pin (630). For example, sliding closure rod (886) distally through rod lock retaining pin (630) causes closure rod (886) to engage shoulders (581) (see FIG. 53A) for expanding distal head (579) to the expanded position for locking with distal end portion (564) of end effector (616).

Figure 51:
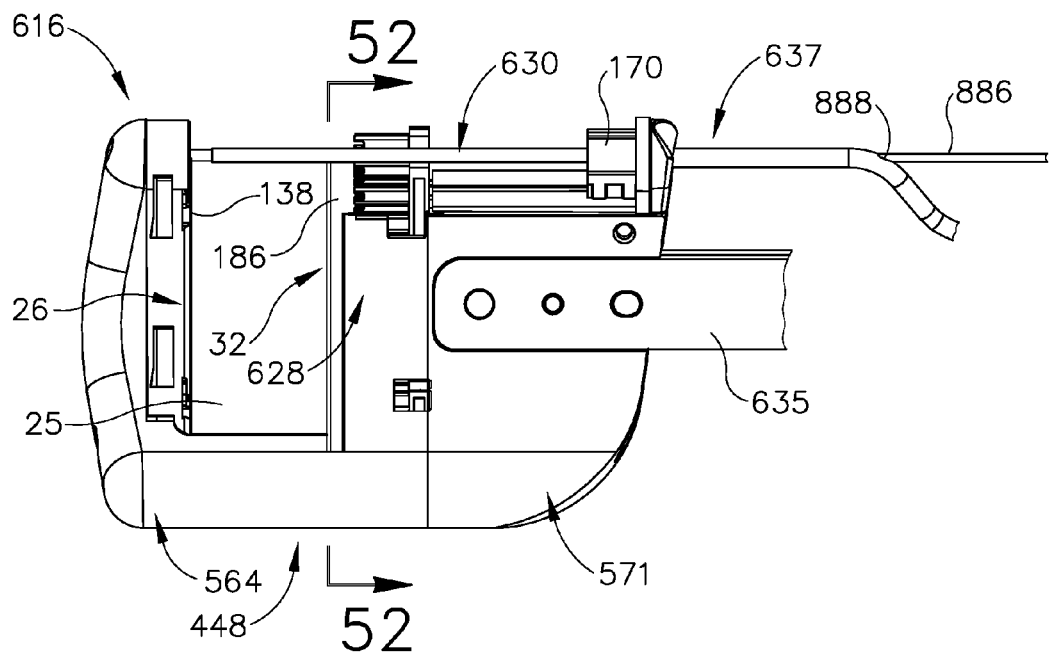
FIG. 51 depicts a right side view of the end effector of FIG. 48, with the retaining pin in an unlocked closed position.
Figure 52:
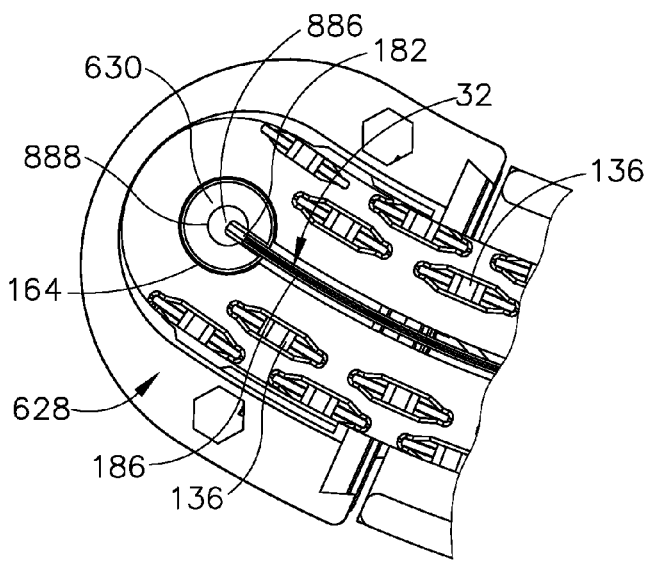
FIG. 52 depicts a cross-sectional view of a portion of the end effector of FIG. 51, taken along section line 52-52 of FIG. 51.

FIGS. 51 and 52 show retaining pin actuation mechanism (637) in the closed configuration. With respect to FIG. 52, slot (182) in rod lock retaining pin (630) slidably receives upper lateral end (186) of knife (32) proximate to closure rod (886) slidably received within elongate aperture (888). Closure rod (886) may thus be selectively translated independently of knife (32) such that closure rod (886) may be locked or unlocked from distal end portion (564) of end effector (616) (see FIG. 51) regardless of the position of knife (32). It will be appreciated that closure rod (886) may be operatively connected to handle and shaft assemblies (612, 614) so that the operator may selectively direct movement of closure rod (886), such as by mechanisms similar to slide (18) (see FIG. 1A). Alternatively, closure rod (886) may have a free end that is configured to be gripped by the operator and manipulated for moving closure rod (886). It will be further appreciated that closure rod (886) may be rigid or flexible so long as closure rod (886) is configured to expand distal head (579) (see FIG. 50) for use. Various suitable alternative mechanisms that may be used to drive movement of closure rod (886) will be apparent to those of ordinary skill in the art in view of the teachings herein.

Figure 53A:
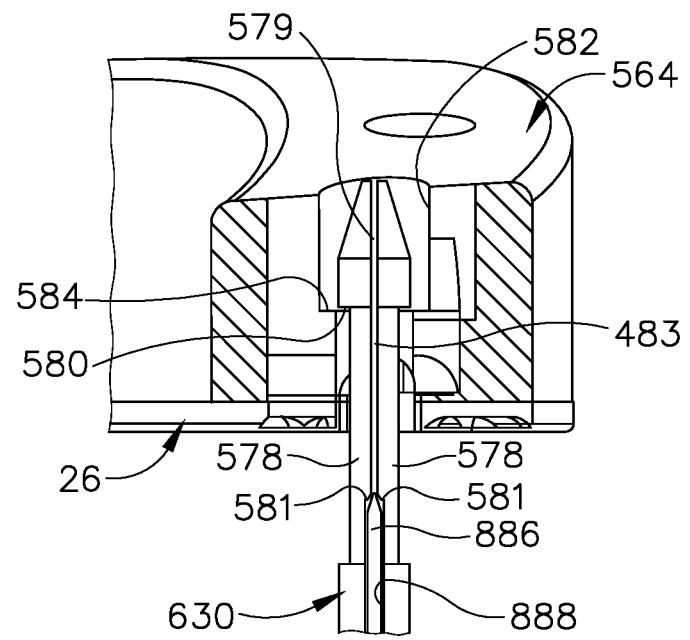
FIG. 53A depicts a cross-sectional view of a portion of the end effector of FIG. 51, with the retaining pin in the unlocked closed position, taken along a centerline of the retaining pin.
Figure 53B:
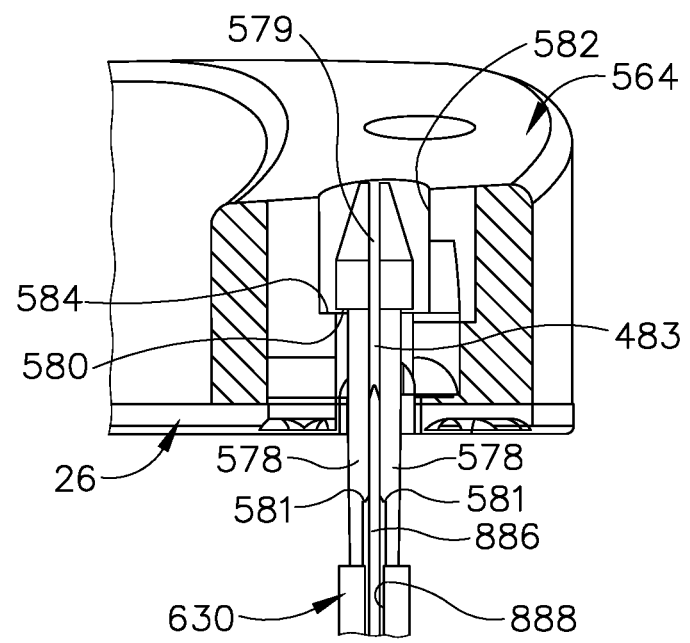
FIG. 53B depicts a cross-sectional view of a portion of the end effector of FIG. 51, with the retaining pin in a locked closed position.

FIGS. 53A-53B illustrate rod lock guide pin (630) locking from an unlocked closed position to the locked closed position. FIG. 53A shows knife lock guide pin (630) in the unlocked closed position following distal movement directed by slide (18) (see FIG. 1A and FIG. 2A) of retaining pin actuation mechanism (637). Regardless of whether or not cartridge (628) and knife (32) have already been moved distally toward anvil (26), the operator selectively translates closure rod (886) distally through elongate aperture (888). Closure rod (886) continues distally such that closure rod (886) engages shoulders (581) to wedge between resilient extensions (578) and expand distal head (579) outwardly from the contracted state to the expanded state. Thereby, distal head (579) is effectively captured in distal portion of retaining pin bore (582) as shown in FIG. 53B. Distal annular ledge (584) of retaining pin bore (582) may then engage proximal annular ledge (580) of rod lock retaining pin (630) to inhibit deflection of distal end portion (564) of end effector (616) as cartridge (628) (see FIG. 51) and tissue are compressed against anvil (26). While exemplary rod lock guide pin (630) is expanded via closure rod (886) in the present example and effectively braces distal end portion (564) in tension, it will be appreciated that alternative structures may expand alternative guide pins; or may otherwise lock with distal end portion (564) such that alternative guide pins may brace distal end portion (564) in compression, as well. To this end, the invention described herein is not intended to be unnecessarily limited to exemplary rod lock guide pin (630).

3. Exemplary Cam Lock Retaining Pin with Cartridge Cam Mechanism and Ledge Lock

Figure 54A:
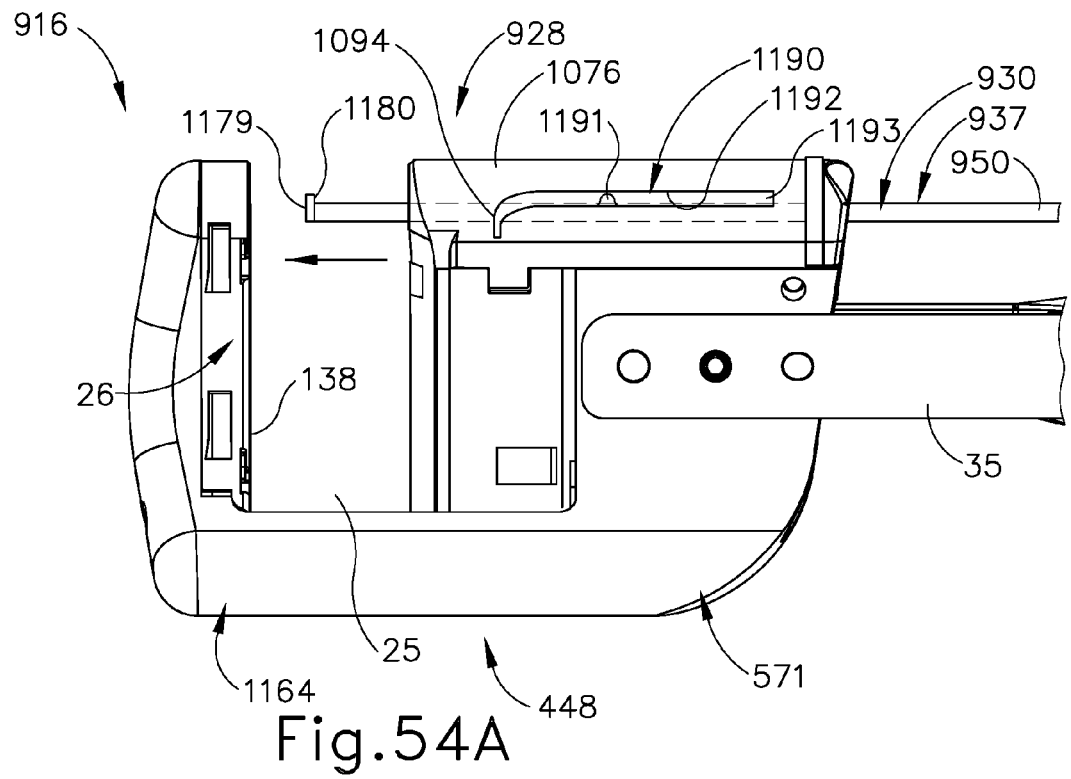
FIG. 54A depicts a right side view of another exemplary end effector having a retaining pin.
Figure 54B:
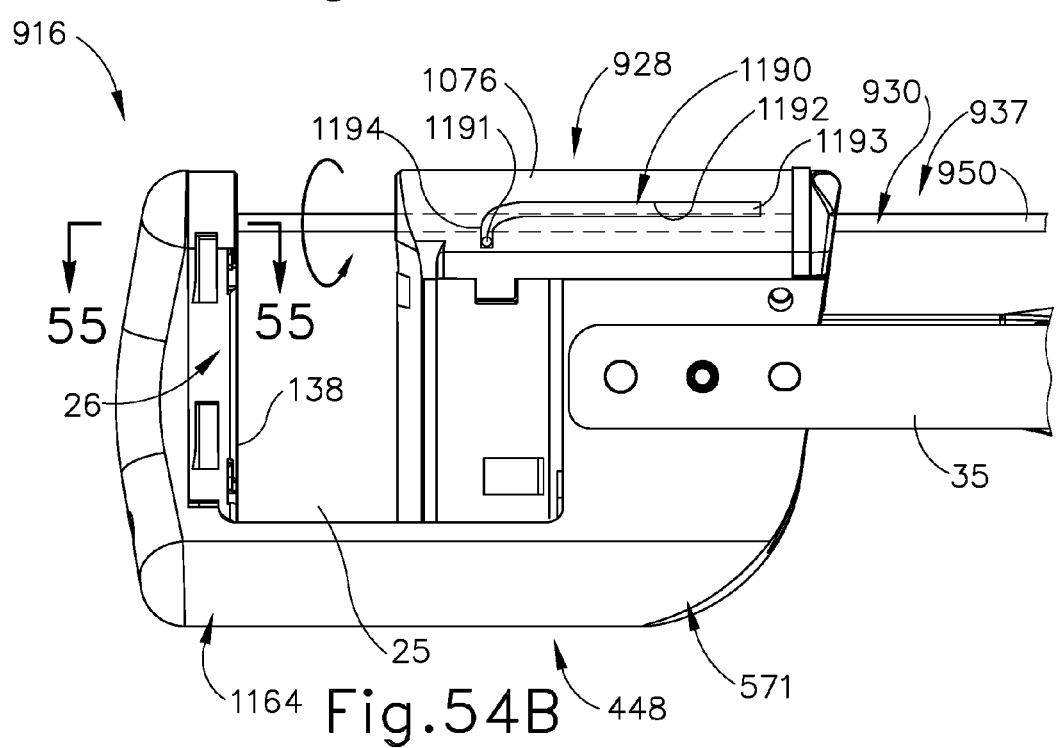
FIG. 54B depicts a right side view of the end effector of FIG. 54A, with the retaining pin moving to a closed position.

FIG. 54A shows another exemplary alternative end effector (916), where a cam lock retaining pin (930) extends through arm (1076) of a cartridge (928) translating from the open configuration toward the closed configuration. As shown in FIGS. 54A-54B, a retaining pin actuation mechanism (937) includes cam lock retaining pin (930) extending directly from a push rod (950) without coupling via couplet (170) (see FIG. 42). Alternatively, cam lock retaining pin (930) may be connected to couplet (170) and push rod (50) for actuation via slide (18) (see FIGS. 1A and 2A) as discussed above in greater detail.

Retaining pin actuation mechanism (937) further includes a cam mechanism (1190) that is configured to guide rotation of cam lock retaining pin (930) as cam lock retaining pin (930) translates into the locked closed position to simultaneously lock and close cam lock retaining pin (930) with distal end portion (1164) of end effector (916). More particularly, cam mechanism (1190) includes a cam tab (1191) extending transversely from cam lock retaining pin (930) and a cam slot (1192) in cartridge housing (132) of cartridge (928). Cam tab (1191) is slidably received within cam slot (1192), which has a proximal linear portion (1193) extending to a distal arcuate portion (1194). Cam slot (1192) is configured to guide rotational movement of cam tab (1191) and, in turn, rotational movement of cam lock retaining pin (930) as push rod (950) distally pushes cam lock retaining pin (930) to distal end portion (1164) of end effector (916) for locking cam lock retaining pin (930) to distal end portion (1164) of end effector (916).

Figure 55:
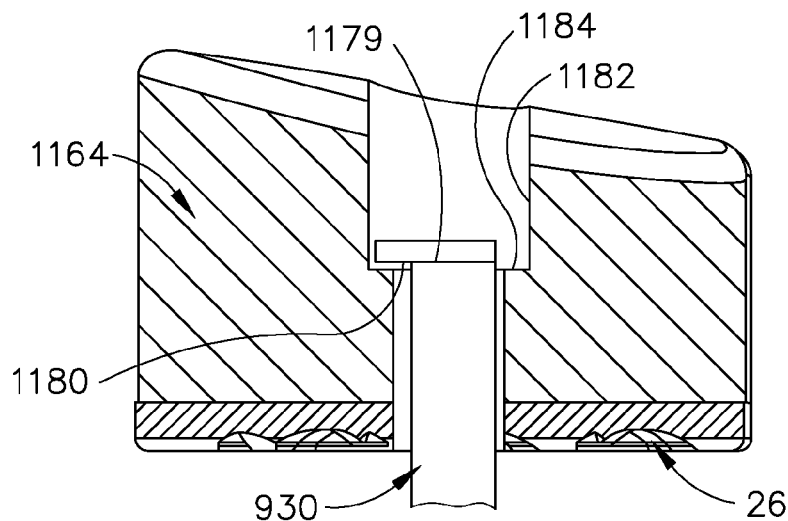
FIG. 55 depicts a cross-sectional view of a portion of the end effector of FIG. 54A, taken along section line 55-55 of FIG. 54B.

A distal head (1179) of cam lock retaining pin (930) is configured to be translatably and rotatably received within a retaining pin bore (1182) of distal end portion (1164) and secured thereto as shown in FIG. 55. Distal head (1179) of cam lock retaining pin (930) defines a proximal oblong ledge (1180), whereas retaining pin bore (1182) is generally oblong in shape to define a distal oblong ledge (1184) (see FIG. 56A). Proximal oblong ledge (1180) is effectively keyed to retaining pin bore (1182) such that as distal head (1179) is configured to translate through retaining pin bore (1182) and then rotate. Proximal oblong ledge (1180) then engages distal oblong ledge (1184). Distal head (1179) is thereby configured to rotatably lock within retaining pin bore (1182) to the closed locked position. While retaining pin bore (1182) and ledge (1180) are oblong in shape so as to overlap when rotated in the present example, it will be appreciated that alternative non-circular shapes may be similarly rotated relative to each other to achieve similarly overlapping and engaging surfaces. For example, such shapes may include, but are not limited to rounded shapes, polygonal shapes, or any combination thereof.

In use, the operator selectively directs push rod (950) distally such that cam slot (1192) guides cam tab (1191) linearly through proximal linear portion (1193) of cam slot (1192) as shown in FIG. 54A and FIG. 55. Cam lock retaining pin (930) thus slides distally toward retaining pin bore (1180) for capturing tissue (not shown) between cartridge (928) and anvil (26) in the unlocked closed configuration. As distal head (1179) is introduced into the proximal portion of retaining pin bore (1182) as shown in FIG. 54B, cam tab (1191) slides into distal arcuate portion (1194), which, in turn, causes cam lock retaining pin to rotate in the distal portion of retaining pin bore (1182). Proximal oblong edge (1180) follows by rotating to overlap with distal oblong edge (1184). Thereby, distal head (1179) is effectively captured in distal portion of retaining pin bore (1182) as shown in FIGS. 54B-55. Distal oblong ledge (1184) of retaining pin bore (1182) may then engage proximal oblong ledge (1180) of cam lock retaining pin (930) to inhibit deflection of distal end portion (1164) of end effector (916) as cartridge (928) and tissue are compressed against anvil (26). While cam lock guide pin (930) effectively braces distal end portion (1164) in tension in the present example, it will be appreciated that alternative structures may expand alternative guide pins; or may otherwise lock with distal end portion (1164) such that alternative guide pins may brace distal end portion (1164) in compression, as well. To this end, the invention described herein is not intended to be unnecessarily limited to exemplary cam lock guide pin (930).

4. Exemplary Cam Lock Retaining Pin with Pin Cam Mechanism and Ledge Lock

Figure 56A:
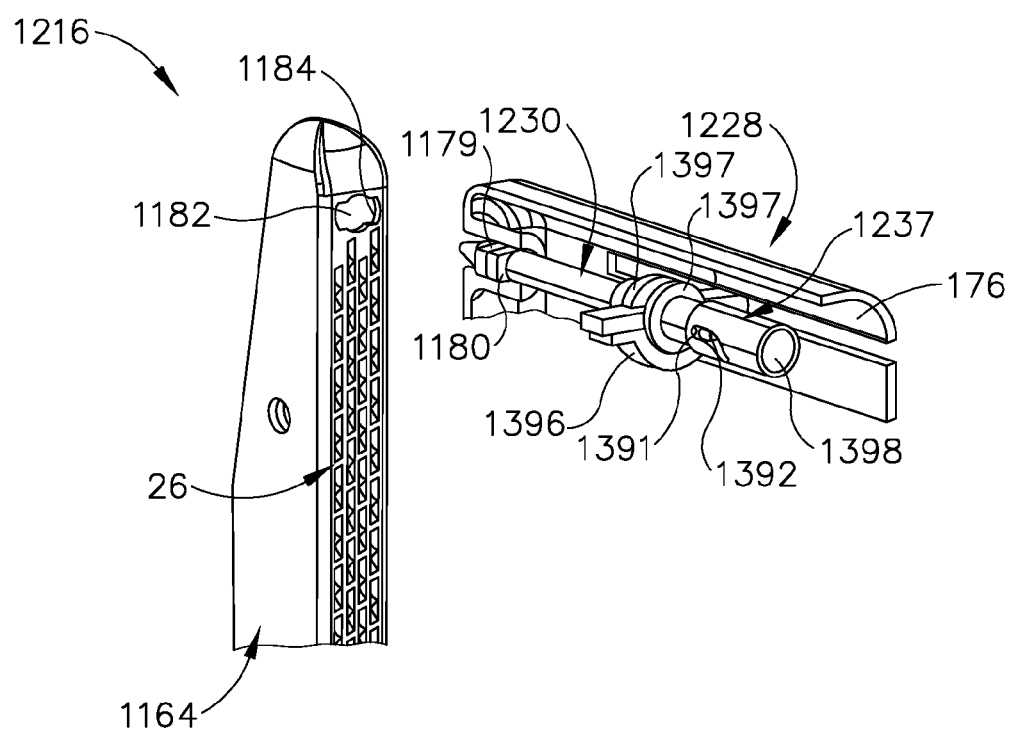
FIG. 56A depicts a rear perspective view of another exemplary end effector having a retaining pin in an open position.
Figure 56B:
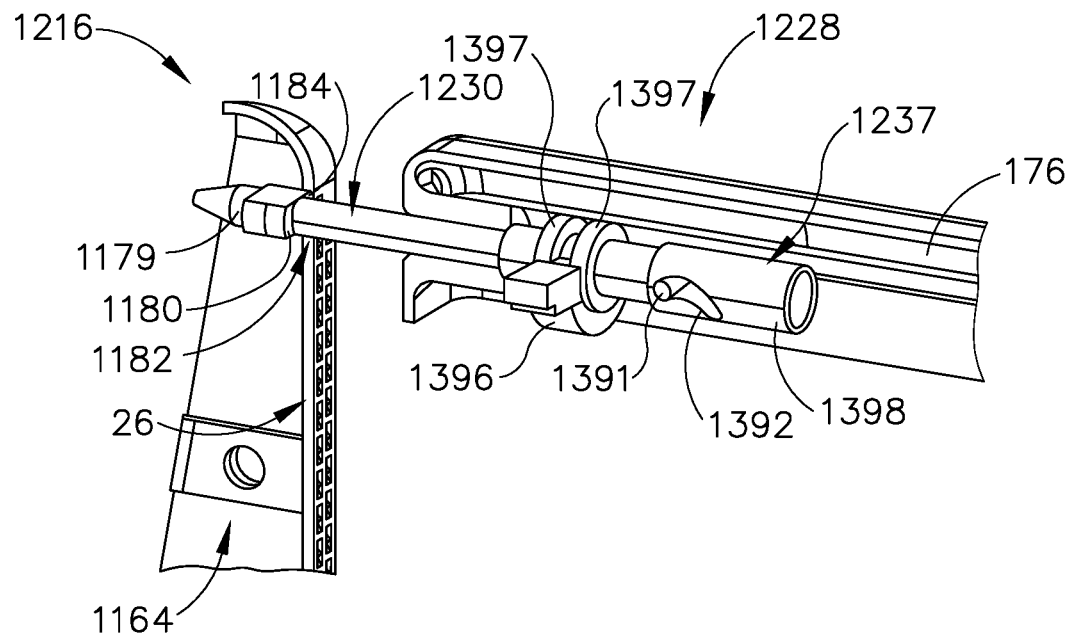
FIG. 56B depicts the rear perspective view of the end effector of FIG. 56A, with the retaining pin in an unlocked closed position.
Figure 56C:
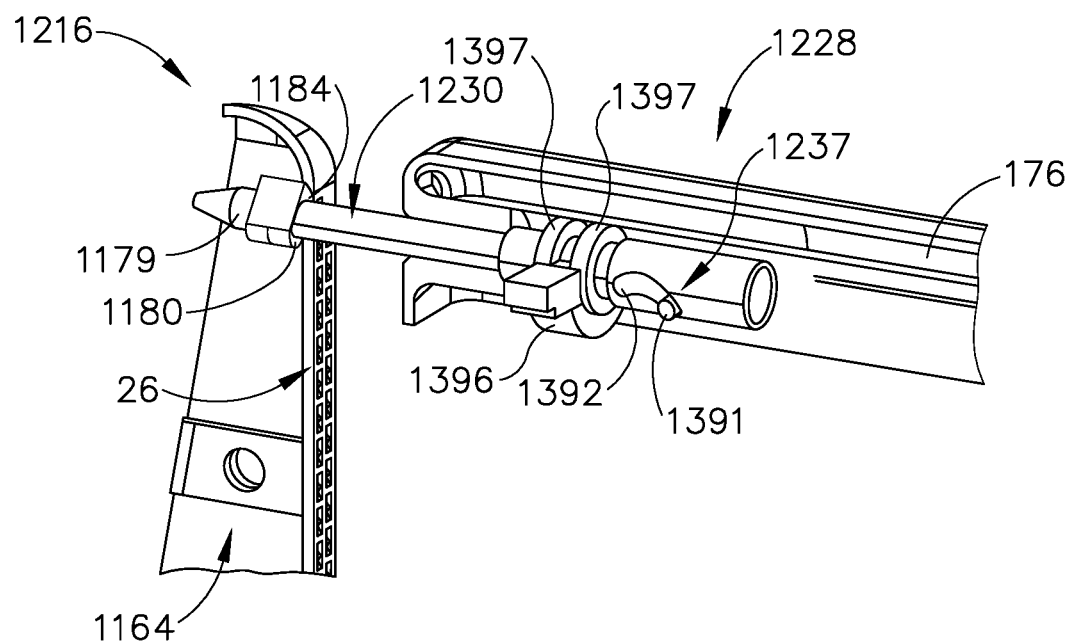
FIG. 56C depicts the rear perspective view of the end effector of FIG. 56A, with the retaining pin in a locked closed position.

FIGS. 56A-56C show another exemplary alternative end effector (1216), where a cam lock retaining pin (1230) extends through arm (176) of a cartridge (1228) translating from the open configuration toward the closed configuration. A retaining pin actuation mechanism (1237) includes cam lock retaining pin (1230) rotatably resting on a support cradle (1396) between opposing flanges (1397). In addition, a distal end portion of cam lock retaining pin (1230) is rotatably driven by retaining pin actuation mechanism (1237), which includes a cam tab (1391) extending from the distal end portion of cam lock retaining pin (1230) received within an arcuate cam slot (1392) of a cam tube (1398).

In use, cam lock retaining pin (1230) may be rotated independently of its translation such that the operator may choose to move cam lock retaining pin (1230) to either open or closed configurations with or without the use of locking the cam lock retaining pin (1230) to the distal end portion (1164) of end effector (1216). More particularly, the operator slides cam lock retaining pin (1230) to the unlocked closed position on support cradle (1396) as shown in FIG. 56B such that distal head (1179) is received within retaining pin bore (1182) as discussed above in greater detail. To lock cam lock retaining pin (1230), push rod (50) (see FIG. 1A), or some alternative pushing mechanism, urges cam tube (1398) distally. Because arcuate cam slot (1392) is configured to direct cam tab (1391) to rotate, the entirety of cam lock retaining pin (1230) also rotates as cam tube (1398) moves distally. In turn, proximal oblong edge (1180) follows by rotating to overlap with distal oblong edge (1184). Thereby, distal head (1179) is effectively captured in distal portion of retaining pin bore (1182) as shown in FIG. 56C. Distal oblong ledge (1184) of retaining pin bore (1182) may then engage proximal oblong ledge (1180) of cam lock retaining pin (1230) to inhibit deflection of distal end portion (1164) of end effector (1216) as cartridge (1228) and tissue are compressed against anvil (26). While cam lock guide pin (1230) effectively braces distal end portion (1164) in tension in the present example, it will be appreciated that alternative structures may expand alternative guide pins; or may otherwise lock with distal end portion (1164) such that alternative guide pins may brace distal end portion (1164) in compression, as well. To this end, the invention described herein is not intended to be unnecessarily limited to exemplary cam lock guide pin (1230).

5. Exemplary Cam Lock Retaining Pin and Threaded Lock

Figure 57A:
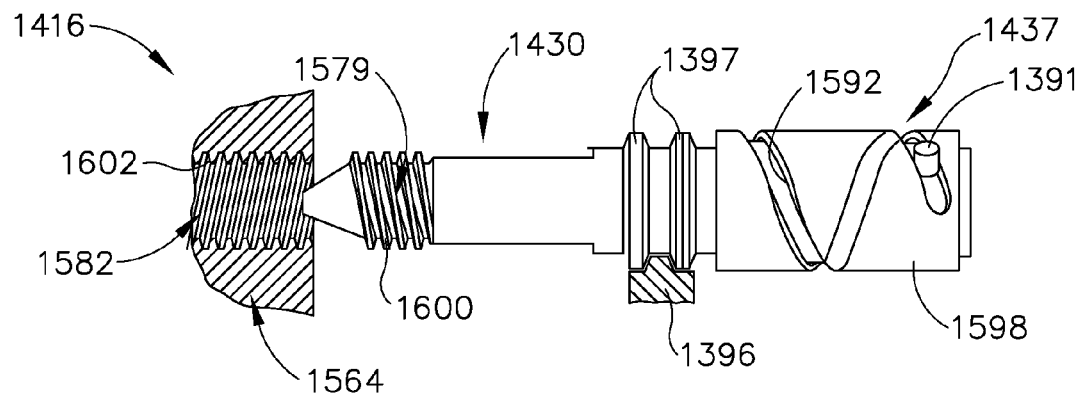
FIG. 57A depicts a right side sectional view of another exemplary end effector having a retaining pin with various components removed for clarity.
Figure 57B:
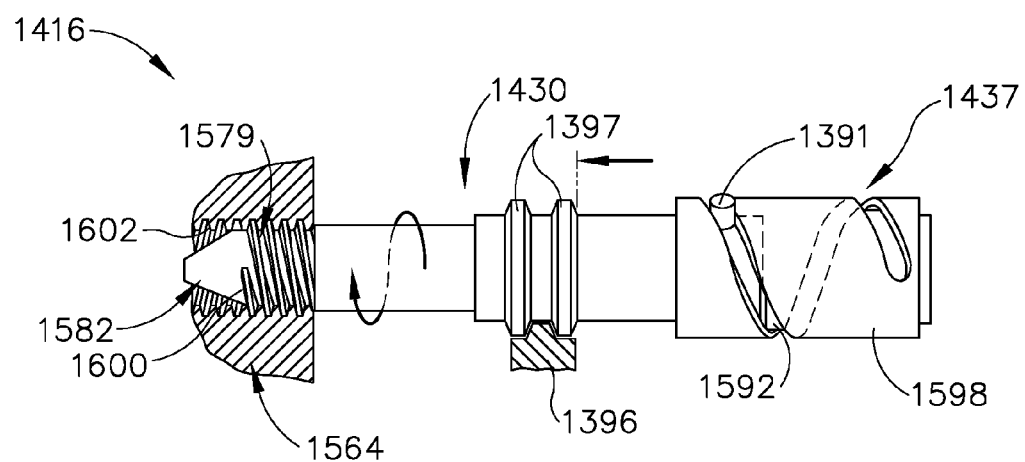
FIG. 57B depicts a right side sectional view of the end effector of FIG. 57A, with the retaining pin moving to the locked closed position.

FIGS. 57A-57B show another alternative end effector (1416) having a cam lock retaining pin (1430) received on a support cradle (1396) between flanges (1397). Cam lock retaining pin (1430) includes a distal head (1579) having a plurality of outer threads (1600) configured to threadably engage with a plurality of inner threads (1602) within a retaining pin bore (1582). Cam lock retaining pin (1430) is rotatably driven distally from the open position to the locked closed position via retaining pin actuation mechanism (1437). Retaining pin actuation mechanism (1437) includes a cam tab (1391) extending from the distal end portion of cam lock retaining pin (1430), which is received within a spiral cam slot (1592) of a cam tube (1598). Cam tube (1598) maintains a fixed position relative to pin (1430). Thus, as support cradle (1396) pushes cam lock retaining pin (1430) distally, spiral cam slot (1592) directs cam tab (1391) to spiral through spiral cam slot (1592), causing cam lock retaining pin (1430) to simultaneously translate and rotate. The simultaneous translation and rotation continues until distal head (1579) fully threads into retaining pin bore (1582) and seats in the closed locked position. Thus, cam lock retaining pin (1430) may brace a distal end portion (1564) of end effector (1416) in both tension and compression due to the threaded engagement. It will be appreciated that support cradle (1396) may be distally and proximally driven by an operative connection with push rod (50) (see FIG. 1A) or some other alternative mechanism. In any case, the invention described herein is not intended to be unnecessarily limited to exemplary cam lock retaining pin (1430).

6. Exemplary Snap Lock Retaining Pin and Ledge Lock

FIGS. 58A-58C show another exemplary alternative end effector (1616) that includes a snap lock retaining pin (1630), which is configured to move from the open position to the locked closed position with distal end portion (1764). A distal end portion (1777) of lock retaining pin (1630) has a distal head in the form of a resilient snap (1779) defining a proximal ledge (1780). In addition, a retaining pin bore (1782) defines a distal ledge (1784). Resilient snap (1779) is configured to resiliently bend about distal ledge (1784) and snap about distal ledge (1784) such that proximal ledge (1784) of resilient snap (1779) engages distal ledge (1784) within retaining pin bore (1782).

In use, a retaining pin actuation mechanism (1637) may include push rod (50) to direct snap lock retaining pin (1630) distally from the open position toward retaining pin bore (1782) as shown in FIG. 58A. As shown in FIG. 58B, resilient snap (1779) is forced distally over distal ledge (1784) within retaining pin bore (1782) until proximal ledge (1784) slides over distal ledge (1784) for engagement thereagainst in the locked closed position shown in FIG. 58C. While snap lock guide pin (1630) effectively braces distal end portion (1764) in tension in the present example, it will be appreciated that alternative structures may expand alternative guide pins; or may otherwise lock with distal end portion (1764) such that alternative guide pins may brace distal end portion (1764) in compression, as well. To this end, the invention described herein is not intended to be unnecessarily limited to exemplary snap lock guide pin (1630).

D. Exemplary End Effector with Variable Height Driver Assembly

Figure 59:
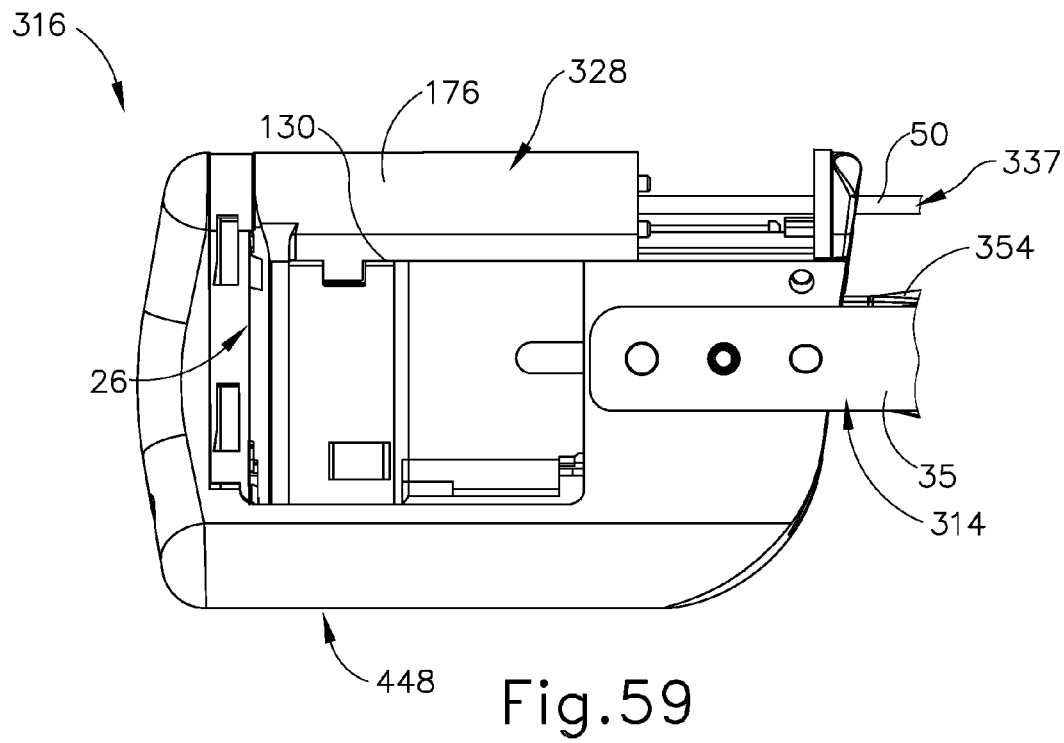
FIG. 59 depicts a right side view of the end effector of FIG. 32 with the pin actuation mechanism in the closed position and the staple cartridge in a closed position.
Figure 60:
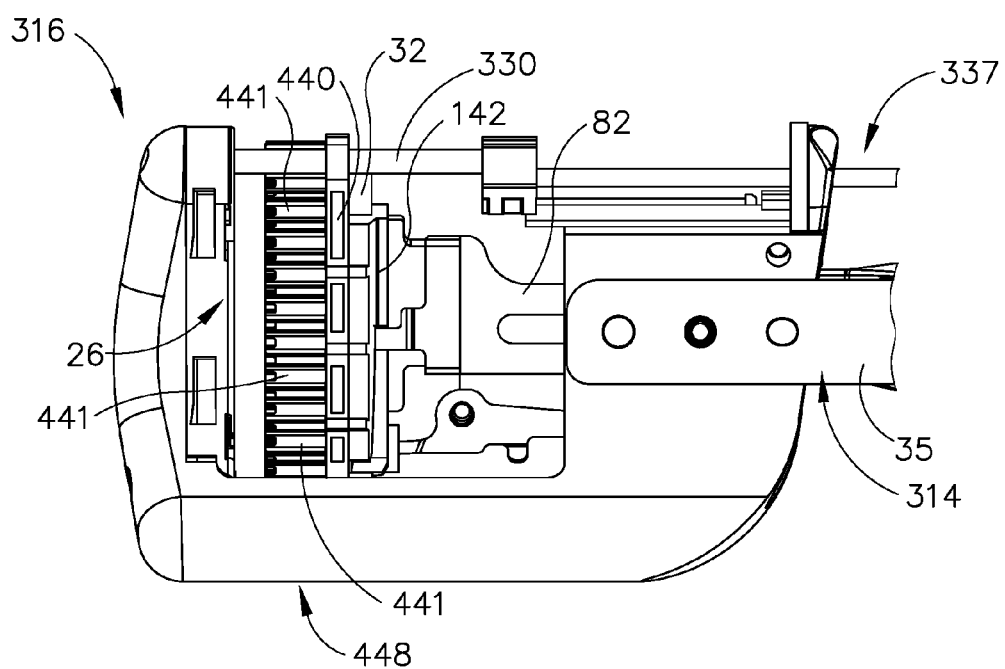
FIG. 60 depicts the end effector of FIG. 32 having a staple driver assembly with various components removed for clarity.

FIGS. 59 and 60 show end effector (316) extending distally from shaft assembly (314) as discussed above in greater detail. Cartridge (328) has been moved to the closed position for firing or actuating firing bar (82) distally to both form staples in the tissue with a driver assembly (440) and sever tissue with knife (32). With respect to staple formation, driver assembly (440) has a plurality of staple drivers (441) extending distally from a driver base (595) below corresponding staple containing slots (136) (see FIGS. 8-9). Each driver (441) has a groove (596) extending along a distal driver surface (597). Each groove (596) is configured to cradle a respective staple thereon for forcing the staple distally toward anvil (26) for formation. While driver assembly (440) has drivers (441) in a predetermined pattern with predetermined heights for various staple formations, it will be appreciated that alternative driver assemblies may be configured with other patterns or heights as contemplated herein to generate other desirable staple formations in tissue as determined to be desirable by the operator. Such predetermined patterns and heights of drivers (441) may also be referred to herein as a predetermined variable height pattern.

Driver assembly (440) of the present example has four offset rows of drivers (441), which will be referred to below as a "front outer row," a "front inner row," a "back outer row," and a "back inner row," that extend from a "left side" to a "right side." The terms "front outer row," "front inner row," "back outer row," "back inner row," are taken with respect to FIG. 59 with like terms being similarly used to describe alternative driver embodiments below. To this end, the terms "front row," "back row," "left side," and "right side" are for relative reference and not intended to unnecessarily limit the invention described herein.

The following examples include driver assemblies with drivers that have different heights (within the same driver assembly). Despite the fact that drivers within the same driver assembly have different heights in this example, these drivers assemblies are configured to ultimately provide formed staples in tissue having the same, uniform height. In other words, for any of the driver assemblies described below, the staples that are driven by the driver assembly will all have the same formed height, despite the fact that the drivers within the assembly have different heights. Drivers that are relatively short within a given driver assembly may have associated staples that are relatively tall. Conversely, drivers that are relatively tall within the same driver assembly may have associated staples that are relatively short. Thus, the unformed staple heights may vary based on variations in driver height, to ultimately yield formed staple heights that are all uniform. This may be desirable to account for uneven load distribution across the length and/or width of the staple driver, to account for variations in tissue thickness, etc. Alternatively, these drivers may be configured with like of varying heights to similarly provide formed staples in tissue having one or more varying, non-uniform height. Such variation may be desirable to accommodate deflection, produce varying forms of staples, or some combination thereof.

Figure 61:
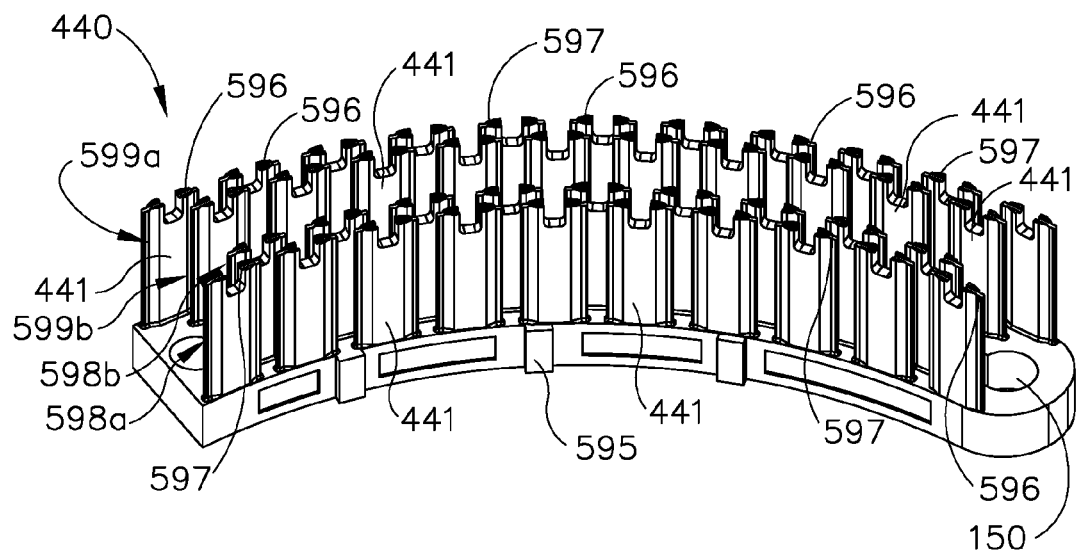
FIG. 61 depicts a right perspective view of the staple driver assembly of FIG. 60.

1. Exemplary Arcuate Driver Assembly with Variable Height Drivers in a First Predetermined Pattern Driver assembly (440) includes two pairs of offset rows of drivers (441) that are configured to direct two pairs of offset rows of staples in tissue for fluidly sealing tissue and inhibit fluid, such as blood, from leaking between the paired rows of staples. To this end, driver assembly (440) of FIG. 61 includes a front outer row (598a) of drivers positioned proximate to a front inner row (598b) on one side of slot (150) and a rear outer row (599a) positioned proximate to a rear inner row (599b) on an opposing side of slot (150). Thereby, drivers (441) are configured to form cooperating staple rows in tissue on each side of knife (32) (see FIG. 6) to fluidly seal the severed tissue on each severed end. In the present example, rows (598a, 598b, 599a, 598b) are arranged along a predetermined arcuate pattern having an inner radius of curvature of between approximately 1.0 inch and approximately 1.2 inches and an outer radius of curvature of between approximately 1.3 inches and approximately 1.5 inches. More particularly the inner radius of curvature is approximately 1.1 inches, and the outer radius of curvature is approximately 1.4 inches. However, it will be appreciated that drivers (441) may be alternatively arranged in other various predetermined patterns, such as other another arcuate pattern, a linear pattern, or some combination thereof.

Figure 62:
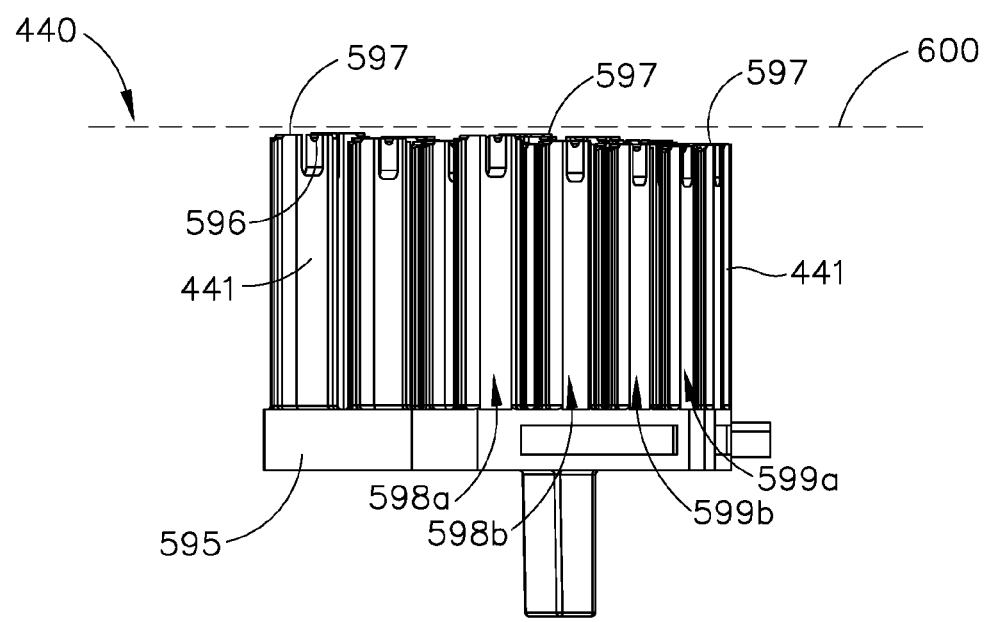
FIG. 62 depicts an upper side view of the staple driver assembly of FIG. 60.

As shown in FIGS. 62-64, drivers (441) extend upwardly from driver base (595) with varying heights such that distal driver surfaces (597) collectively define a predetermined curvature that is configured to drive staples to various depths and/or offset a predetermined deflection relative to anvil (26) (see FIG. 60). Such predetermined curvature may extend in one dimension, two dimensions, or three dimensions along distal driver surfaces (597) of driver assembly (440). In other words, at least one driver (441) has a height larger or smaller than another driver (441).

For example, FIGS. 62-64 illustrate a reference plane (600) to more clearly show height differences among drivers (441). FIG. 62 shows a right side of driver assembly (440) having front outer and inner rows (598a, 598b) with a height that is greater than the heights of rear inner and outer rows (599b, 599a). More particularly, the varying height of drivers (441) tends to taper down from front outer row (598a) toward rear outer row (599a). As shown in FIGS. 63-64, each row (598a, 598b, 599a, 598b) of drivers (441) is configured with relatively larger drivers (441) to the left and right sides and relatively smaller drivers (441) in the middle between the left and right sides. Rows (598a, 598b, 599a, 598b) thus taper down from the left and right sides toward the middle.

Figure 65:
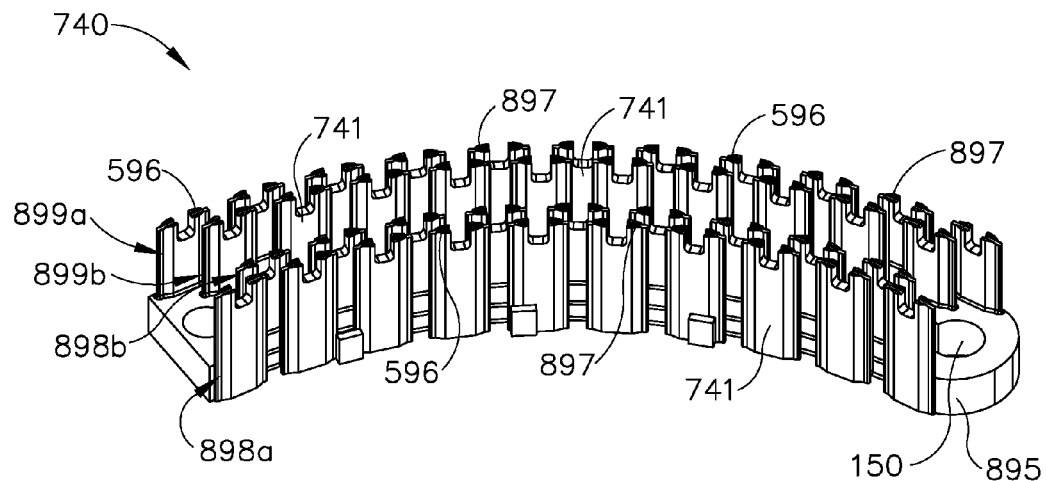
FIG. 65 depicts a right perspective view of another exemplary staple driver assembly.

2. Exemplary Arcuate Driver Assembly with Variable Height Drivers in a Second Predetermined Pattern Another exemplary driver assembly (740) shown in FIG. 65 includes two pairs of offset rows of drivers (741) that are configured to direct two pairs of offset rows of staples in tissue for fluidly sealing tissue and inhibit fluid, such as blood, from leaking between the paired rows of staples. To this end, driver assembly (740) of FIG. 65 includes a front outer row (898a) of drivers (741) that is positioned proximate to a front inner row (898b) on one side of slot (150); and a rear outer row (899a) that is positioned proximate to a rear inner row (899b) on an opposing side of slot (150). Drivers (741) are thereby configured to form cooperating staple rows in tissue on each side of knife (32) (see FIG. 6) to fluidly seal the severed tissue on each severed end. In the present example, rows (898a, 898b, 899a, 898b) are arranged along a predetermined arcuate pattern having an inner radius of curvature of between approximately 1.0 inch and approximately 1.2 inches and an outer radius of curvature of between approximately 1.3 inches and approximately 1.5 inches. More particularly the inner radius of curvature is approximately 1.1 inches, and the outer radius of curvature is approximately 1.4 inches. However, it will be appreciated that drivers (741) may be alternatively arranged in other various predetermined patterns, such as another arcuate pattern, a linear pattern, or some combination thereof.

Figure 66:
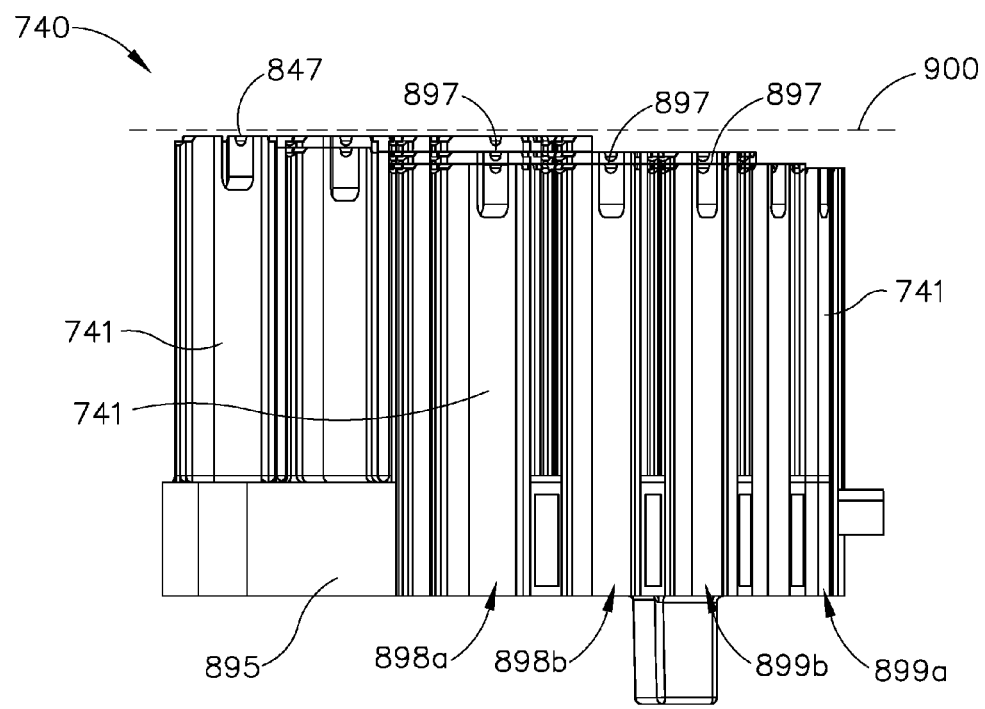
FIG. 66 depicts an upper side view of the staple driver assembly of FIG. 65.

As shown in FIGS. 66-68, drivers (741) extend upwardly from driver base (895) with varying heights such that distal driver surfaces (897) collectively define a predetermined curvature that is configured to drive staples to various depths and/or offset a predetermined deflection relative to anvil (26) (see FIG. 60). Such predetermined curvature may extend in one dimension, two dimensions, or three dimensions along distal driver surfaces (897) of driver assembly (740). In other words, at least one driver (741) has a height larger or smaller than another driver (741).

For example, FIGS. 66-68 illustrate a reference plane (900) to more clearly show height differences among drivers (741). FIG. 66 shows a right side of driver assembly (840) having front outer and inner rows (898a, 898b) with a height that is greater than the heights of rear inner and outer rows (899b, 899a). More particularly, the varying height of drivers (741) tends to taper down from front outer row (898a) toward rear outer row (899a). As shown in FIGS. 67-68, each row (898a, 898b, 899a, 898b) of drivers (741) has a generally uniform height from the left side to the right side despite having varying heights from front to rear.

Figure 69:
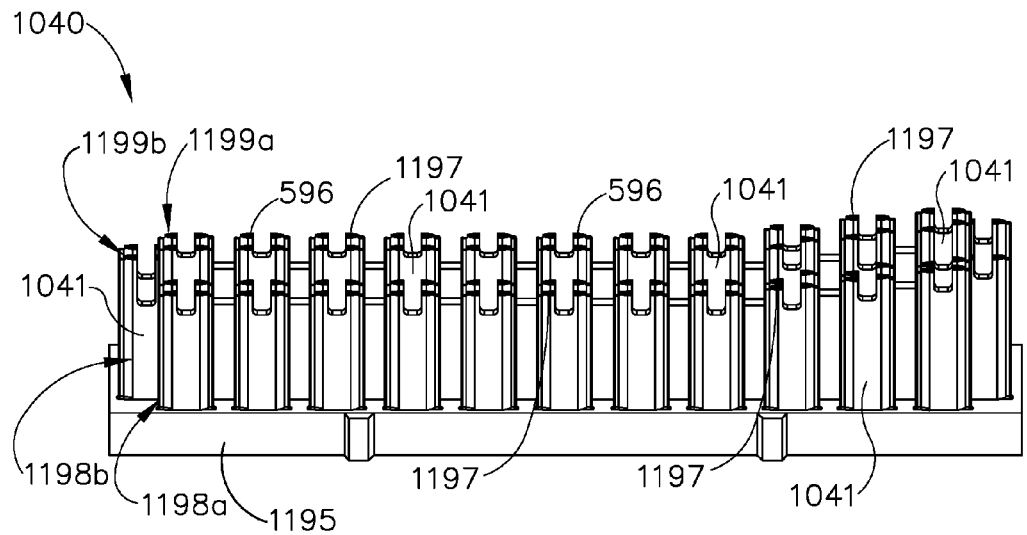
FIG. 69 depicts a right perspective view of another exemplary staple driver assembly.

3. Exemplary Linear Driver Assembly with Variable Height Drivers in a Third Predetermined Pattern Another exemplary driver assembly (1040) shown in FIG. 69 includes two pairs of offset rows of drivers (1041) that are configured to direct two pairs of offset rows of staples in tissue for fluidly sealing tissue and inhibit fluid, such as blood, from leaking between the paired rows of staples. To this end, driver assembly (1040) of FIG. 69 includes a front outer row (1198a) of drivers positioned proximate to a front inner row (1198b) on one side of slot (not shown) and a rear outer row (1199a) positioned proximate to a rear inner row (1199b) on an opposing side of slot (not shown). Drivers (1041) are thereby configured to form cooperating staple rows in tissue on each side of knife (32) (not shown) to fluidly seal the severed tissue on each severed end. In the present example, rows (1198a, 1198b, 1199a, 1198b) are arranged along a predetermined linear pattern. However, it will be appreciated that drivers (1041) may be alternatively arranged in other various predetermined patterns, such as another linear pattern, an arcuate pattern, or some combination thereof. It will be further appreciated that knife (not shown) and slot (not shown) may be configured to extend linearly but function similarly to slot (150) and knife (32) as shown in FIG. 6 and discussed above in greater detail.

Figure 70:
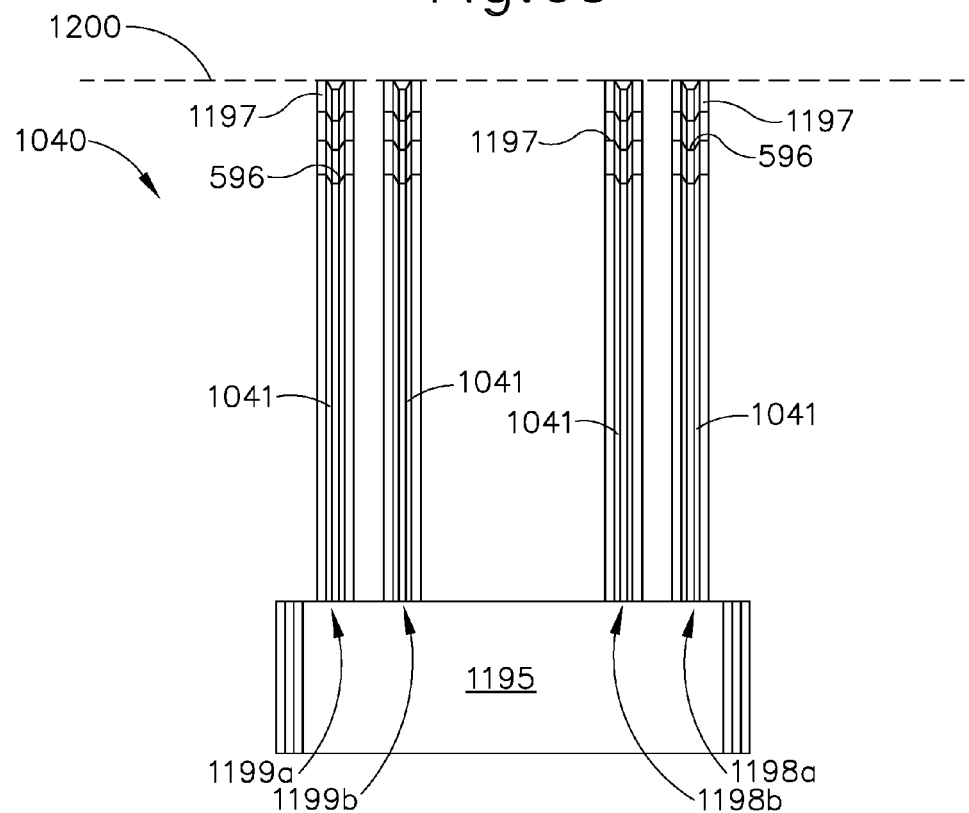
FIG. 70 depicts an upper side view of the staple driver assembly of FIG. 69.

As shown in FIGS. 70-72, drivers (1041) extend upwardly from driver base (1195) with varying heights such that distal driver surfaces (1197) collectively define a predetermined curvature that is configured to drive staples to various depths and/or offset a predetermined deflection relative to anvil (not shown). Such predetermined curvature may extend in one dimension, two dimensions, or three dimensions along distal driver surfaces (1197) of driver assembly (1040). In other words, at least one driver (1141) has a height larger or smaller than another driver (1141).

For example, FIGS. 70-72 illustrate a reference plane (1200) to more clearly show height differences among drivers (1141). FIG. 70 shows a side of driver assembly (1040) having front outer and inner rows (1198a, 1198b) and rear outer and inner rows (1199a, 1199b) with a generally uniform height, respectively, from the front side to the rear side despite having varying heights from left to right. As shown in FIGS. 71-72, each row (1198a, 1198b, 1199a, 1198b) of drivers (1041) is generally larger on the right side, tapers down toward the middle, and remains uniform from the middle to the right side.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of using an instrument to manipulate tissue of a patient, wherein the instrument has an end effector, the method comprising: (a) positioning the tissue within a gap between a cartridge and an anvil of the end effector, wherein the cartridge includes a knife and a plurality of staples, wherein the anvil is located in a distal end portion of the end effector, and wherein the end effector is in an open configuration during the act of positioning the tissue between the anvil and the cartridge; (b) positioning the tissue against a guide pin to laterally position the tissue relative to the cartridge and the anvil, (c) moving a retaining pin from an open position toward a closed position across the gap, thereby capturing the tissue between the cartridge, the anvil, the guide pin, and the retaining pin; (d) moving the cartridge toward the anvil such that the end effector is in a closed configuration; (e) inhibiting deflection of the distal end portion of the end effector for aligning the cartridge and the anvil, wherein at least one of the guide pin or the retaining pin connects to the distal end portion to secure the distal end portion relative to a proximal end portion of the end effector to thereby inhibit deflection of the distal end portion of the end effector; (f) forming the plurality of staples within the tissue and fluidly sealing the tissue; and (g) cutting the tissue with the knife, thereby severing the tissue.

Example 2

The method of Example 1, wherein inhibiting deflection is provided by the guide pin connected to the distal end portion and the proximal end portion to secure the distal end portion relative to the proximal end portion of the end effector.

Example 3

The method of any one or more of Examples 1 through 2, further comprising increasing tension in the guide pin such that guide pin further inhibits deflection of the distal end portion of the end effector relative to the proximal end portion of the end effector.

Example 4

The method of any one or more of Examples 1 through 3, wherein inhibiting deflection is provided by the retaining pin connected to the distal end portion and the proximal end portion to secure the distal end portion relative to the proximal end portion of the end effector.

Example 5

The method of any one or more of Examples 1 through 4, further comprising locking the retaining pin to the distal end portion in a locked closed position.

Example 6

The method of Example 5, wherein the distal end portion includes a first ledge, the retaining pin includes a second ledge, and the method further comprises overlapping the second ledge with the first ledge to lock the retaining pin in the locked closed position.

Example 7

The method of any one or more of Examples 5 through 6, wherein locking the retaining pin further includes expanding a portion of the retaining pin within the distal end portion of the end effector.

Example 8

The method of Example 7, wherein expanding a portion of the retaining pin further includes sliding the knife toward the anvil such that the knife forces the portion of the retaining pin to expand.

Example 9

The method of Example 7, wherein expanding a portion of the retaining pin further includes sliding a closure rod through the retaining pin toward the distal end portion such that the closure rod forces the portion of the retaining pin to expand.

Example 10

The method of any one or more of Examples 5 through 9, wherein the end effector includes a cam mechanism having a cam tab and a cam slot, and the method further comprises guiding the cam tab through the cam slot and rotating the retaining pin therewith to the locked closed position.

Example 11

The method of any one or more of Examples 1 through 10, wherein the guide pin is rotatably supported in a support cradle, and the method further comprises translating the support cradle and the retaining pin toward the distal end portion.

Example 12

The method of Example 5, wherein the distal end portion includes a first plurality of threads, the retaining pin includes a second plurality of threads, and the method further comprises threading the second plurality of threads with the first plurality of threads to lock the retaining pin in the locked closed position.

Example 13

The method of Example 12, wherein the end effector includes a cam mechanism having a cam tab and a spiral cam slot, and the method further comprises guiding the cam tab through the spiral cam slot and rotating the retaining pin therewith to the locked closed position.

Example 14

The method of any one or more of Examples 1 through 13, wherein the cartridge includes a driver assembly and a plurality of staple slots, wherein the driver assembly has a plurality of drivers respectively supporting the plurality of staples thereon within the plurality of staple slots, wherein at least one driver of the plurality of drivers has a variable distal height relative to at least another driver of the plurality of drivers in a predetermined variable height pattern, and the method further comprises directing the plurality of drivers with the respective plurality of staples toward the anvil in the predetermined variable height pattern.

Example 15

The method of Example 14, further comprising deflecting the distal end portion of end effector with the anvil relative to the plurality of drivers a predetermined deflection such that the predetermined variable height pattern accommodates the predetermined deflection, and wherein forming the plurality of staples further includes uniformly forming the plurality of staples within the tissue.

Example 16

The method of Example 14, wherein forming the plurality of staples further includes non-uniformly forming the plurality of staples within the tissue.

Example 17

The method of any one or more of Examples 1 through 16, wherein the end effector is operatively attached to a body having a firing member configured to selectively actuate a firing stroke and move the cartridge from an unfired cartridge position to a fired cartridge position for forming the plurality of staples and cutting the tissue, wherein the method further comprises simultaneously communicating an audible sound and a visual indicia with a feedback generator to the operator to indicate that the firing member completed the firing stroke for actuating the cartridge to the fired cartridge position.

Example 18

The method of any one or more of Examples 1 through 17, wherein the tissue is a colon tissue, and the method further comprises performing a lower anterior resection of the colon tissue.

Example 19

The method of Example 18, wherein the distal end portion of the end effector includes, a first end, a second end laterally opposite from the first end, a distal crest laterally positioned between the first and second ends, wherein the distal crest projects distally beyond the first and second ends; and an arcuate distal surface extending along the distal crest and laterally between the first and second ends, wherein the arcuate distal surface at the distal crest has a radius of curvature configured to be received against a pelvic bowl of the patient to position the end effector relative to the colon tissue of the patient for manipulating the colon tissue with the cartridge, wherein the method further comprises positioning the arcuate distal surface of the distal end portion of the end effector against the pelvic bowl such that the end effector is in a predetermined orientation relative to the colon tissue thereby positioning the cartridge relative to the colon tissue for performing the lower anterior resection of the colon tissue.

Example 20

A method of using an instrument to manipulate colon tissue of a patient, wherein the instrument has an end effector, the method comprising: (a) positioning the colon tissue within a gap between a cartridge and an anvil of an end effector, wherein the cartridge includes a knife and a plurality of staples, wherein the anvil is received within a distal end portion of the end effector, and wherein the end effector is in an open configuration during the act of positioning the colon tissue between the anvil and the cartridge; (b) positioning the colon tissue against a guide pin, (c) moving a retaining pin from an open position toward a closed position across the gap, thereby capturing the colon tissue between the cartridge, the anvil, the guide pin, and the retaining pin; (d) moving the cartridge toward the anvil such that the end effector is in a closed configuration; (e) inhibiting deflection of the distal end portion of the end effector for aligning the cartridge and the anvil, wherein at least one of the guide pin and the retaining pin connects to the distal end portion to secure the distal end portion relative to a proximal end portion of the end effector; (f) forming the plurality of staples within the colon tissue and fluidly sealing the colon tissue; and (g) cutting the colon tissue with the knife, thereby providing a lower anterior resection of the colon tissue.

Example 21

A surgical instrument comprising: (a) a body; (b) a shaft assembly extending distally from the body; and (c) an end effector extending distally from the shaft assembly and configured to receive a cartridge for manipulating tissue of a patient, the end effector including: (i) a distal end portion, (ii) a proximal end portion, (iii) a gap between the distal end portion and the proximal end portion, and (iv) a retaining pin having a distal head, wherein the retaining pin is selectively movable from an open position to a locked closed position, wherein the retaining pin in the open position is proximally positioned relative to the gap such that the gap is configured to receive the tissue, wherein the retaining pin in the locked closed position extends across the gap such that retaining pin is configured to capture the tissue within the gap, wherein the distal head of the retaining pin is configured engage the distal end portion of the end effector and secure the distal end portion of the end effector relative to the proximal end portion of the end effector via the retaining pin projecting therebetween.

Example 22

The surgical instrument of Example 21, further comprising a cartridge having a cartridge housing, wherein the retaining pin is at least partially contained within the cartridge housing in the open position.

Example 23

The surgical instrument of Example 22, wherein the cartridge includes at least one of a knife or a plurality of staples, wherein the knife is configured to cut the tissue, and wherein the plurality of staples are configured to fasten the tissue.

Example 24

The surgical instrument of any one or more of Examples 21 through 23, wherein the distal end portion of the end effector includes a bore configured to receive the distal head of the retaining pin in the locked closed position.

Example 25

The surgical instrument of Example 24, wherein the distal end portion of the end effector has a first ledge within the bore, wherein the distal head of the retaining pin has a second ledge, wherein the second ledge is configured to overlap within the first ledge to lock distal head of the retaining pin to the distal end portion of the end effector.

Example 26

The surgical instrument of Example 25, wherein the distal head of the retaining pin is configured to expand from a contracted state to an expanded state for overlapping the first and second ledges.

Example 27

The surgical instrument of Example 26, wherein the end effector further includes a knife configured to move from a proximal knife position toward a distal knife position, wherein at least a portion of the knife is slidably received within the retaining pin, wherein the knife is configured to expand the distal head from the contracted state to the expanded state when the knife is moved from the proximal knife position toward the distal knife position.

Example 28

The surgical instrument of Example 27, wherein the knife is configured to move from the distal knife position toward the proximal knife position, and wherein the knife is configured to contract the distal head from the expanded state to the contracted state and unlock the distal head of the retaining pin from the distal end portion of the end effector when the knife is moved from the distal knife position toward the proximal knife position.

Example 29

The surgical instrument of Example 26, wherein the end effector further includes a closure member configured to move from a proximal member position toward a distal member position, wherein the closure member is slidably received within the retaining pin, wherein the closure member is configured to expand the distal head from the contracted state to the expanded state when the closure member is moved from the proximal member position toward the distal member position.

Example 30

The surgical instrument of Example 29, wherein the closure member is configured to move from the distal member position toward the proximal member position, and wherein the closure member is configured to contract the distal head from the expanded state to the contracted state and unlock the distal head of the retaining pin from the distal end portion of the end effector when the closure member is moved from the distal member position toward the proximal member position.

Example 31

The surgical instrument of Example 25, wherein the end effector includes a cam mechanism having a cam tab and a cam slot, wherein the cam tab extends from the retaining pin within the cam slot, and wherein the cam slot is configured to guide movement of the retaining pin such that the second ledge rotatably overlaps with the first ledge into the locked closed position.

Example 32

The surgical instrument of Example 31, further comprising a cartridge having a cartridge housing, wherein the cam slot is defined by the cartridge housing.

Example 33

The surgical instrument of Example 31, wherein the cam slot is defined by a cam tube, and wherein the retaining pin is received within the cam tube.

Example 34

The surgical instrument of Example 24, wherein the distal end portion of the end effector has a first plurality of threads within the bore, the distal head of the retaining pin has a second plurality of threads, and the second plurality of threads is configure to threadably engage the first plurality of threads to lock the distal head of the retaining pin to the distal end portion of the end effector.

Example 35

The surgical instrument of Example 34, wherein the end effector includes a cam mechanism having a cam tab and a spiral cam slot, wherein the cam tab extends from the retaining pin within the spiral cam slot, and wherein the spiral cam slot is configured to guide movement of the retaining pin such that the second plurality of threads is rotatably driven into engagement with the first plurality of threads into the locked closed position.

Example 36

The surgical instrument of Example 24, wherein the distal head of the retaining pin includes a resilient snap, wherein the distal end portion of the end effector has a first ledge within the bore, wherein the resilient snap of the retaining pin has a second ledge, wherein the second ledge is configured to overlap within the first ledge to lock distal head of the retaining pin to the distal end portion of the end effector.

Example 37

A cartridge for an end effector of a surgical instrument, wherein the end effector has a distal end portion, a proximal end portion, and a gap therebetween for receiving the tissue, the cartridge comprising: (a) a cartridge housing configured to be received by the end effector, wherein the cartridge housing contains at least one of a knife or a plurality of staples, wherein the knife is configured to cut tissue, and wherein the plurality of staples are configured to fasten tissue; and (b) a retaining pin having a distal head, wherein the retaining pin is selectively movable from an open position to a locked closed position, wherein the retaining pin in the open position is configured to be proximally positioned relative to the gap for receiving tissue, wherein the retaining pin in the locked closed position is configured to extend across the gap such that retaining pin is configured to capture tissue within the gap, wherein the retaining pin is configured engage the distal end portion of the end effector and secure the distal end portion of the end effector relative to the proximal end portion of the end effector.

Example 38

The cartridge of Example 37, wherein the retaining pin is at least partially contained within the cartridge housing in the open position.

Example 39

A method of manipulating tissue of a patient with a surgical instrument, wherein the surgical instrument includes a body, a shaft assembly extending distally from the body, and an end effector extending distally from the shaft assembly, wherein the end effector includes a cartridge configured to manipulate the tissue, a distal end portion, a proximal end portion, a gap between the distal and proximal end portions configured to receive the tissue, and a retaining pin, the method comprising: (a) positioning the tissue within the gap; (b) moving the retaining pin from an open position toward a locked closed position to capture the tissue within the gap; (c) engaging a distal head of the retaining pin with the distal end portion of the end effector in the locked closed position to secure the distal end portion of the end effector relative to the proximal end portion of the end effector; and (d) manipulating the tissue of the patient with the cartridge.

Example 40

The method of Example 39, further comprising inhibiting deflection of the distal end portion of the end effector with the retaining pin in the locked closed position.

Example 41

A surgical instrument comprising: (a) a body having a firing mechanism configured to be selectively manipulated by an operator; (b) a shaft assembly extending distally from the body; and (c) an end effector extending distally from the shaft assembly and configured to receive a cartridge for manipulating tissue of a patient, the end effector including: (i) a distal end portion, (ii) a proximal end portion, (iii) a gap between the distal end portion and the proximal end portion, and (iv) a guide pin extending from the distal end portion to the proximal portion, wherein the guide pin is configured to receive the tissue thereagainst for positioning tissue within the gap, wherein the guide pin is connected to each of the distal and proximal end portions to secure the distal end portion relative to the proximal end portion and inhibit deflection of the distal end portion relative to the proximal end portion.

Example 42

The surgical instrument of Example 41, wherein the distal end portion extends distally from the proximal end portion

39 in the form of a hook-shape supporting structure with the gap therebetween configured to receive the tissue.

Example 43

The surgical instrument of any one or more of Examples 41 through 42, wherein the guide pin is connected to each of the distal and proximal end portions in tension to secure the distal end portion relative to the proximal end portion.

Example 44

The surgical instrument of any one or more of Examples 41 through 43, wherein the guide pin is in the form of a threaded fastener.

Example 45

The surgical instrument of any one or more of Examples 41 through 44, wherein the distal end portion has a distal pin bore and the proximal end portion has a proximal pin bore, wherein the distal and proximal pin bores are positioned opposite each other and receive the guide pin therein.

Example 46

The surgical instrument of Example 45, wherein the proximal pin bore includes a threaded nut, and wherein the guide pin is threaded into the threaded nut to be connected therein.

Example 47

The surgical instrument of Example 46, wherein the guide pin is in the form of a threaded fastener.

Example 48

The surgical instrument of any one or more of Examples 44 through 47, wherein the threaded fastener is connected to each of the distal and proximal end portions in tension to secure the distal end portion relative to the proximal end portion.

Example 49

The surgical instrument of any one or more of Examples 41 through 48, further comprising a cartridge received against the guide pin, wherein the cartridge is configured to be guided from the proximal end portion toward the distal end portion along the guide pin.

Example 50

The surgical instrument of Example 49, wherein the cartridge includes at least one of a knife or a plurality of staples, wherein the knife is configured to cut the tissue, and wherein the plurality of staples are configured to fasten the tissue.

Example 51

The surgical instrument of Example 50, wherein the cartridge includes each of the knife and the plurality of staples.

Example 52

The surgical instrument of any one or more of Examples 41 through 51, wherein the distal end portion of the end effector includes an anvil, and the guide pin is configured to inhibit deflection of the anvil relative to the proximal end portion.

Example 53

The surgical instrument of any one or more of Examples 41 through 52, wherein the guide pin is a rigid guide pin.

Example 54

An end effector of a surgical instrument for manipulating tissue of a patient with a cartridge, comprising: (a) a distal end portion; (b) a proximal end portion; (c) a gap between the distal end portion and the proximal end portion; and (d) a guide pin extending from the distal end portion to the proximal portion, wherein the guide pin is configured to receive the tissue thereagainst for positioning the tissue within the gap, wherein the guide pin is connected to each of the distal and proximal end portions to secure the distal end portion relative to the proximal end portion and inhibit deflection of the distal end portion relative to the proximal end portion.

Example 55

The surgical instrument of Example 54, wherein the distal end portion extends distally from the proximal end portion in the form of a hook-shape supporting structure with the gap therebetween configured to receive the tissue.

Example 56

The surgical instrument of any one or more of Examples 54 through 55, wherein the guide pin is connected to each of the distal and proximal end portions in tension to secure the distal end portion relative to the proximal end portion.

Example 57

The surgical instrument of any one or more of Examples 54 through 56, wherein the guide pin is in the form of a threaded fastener.

Example 58

The surgical instrument of any one or more of Examples 54 through 57, further comprising a cartridge received against the guide pin, wherein the cartridge is configured to be guided from the proximal end portion toward the distal end portion along the guide pin.

Example 59

A method of manipulating tissue of a patient with a surgical instrument, the surgical instrument including a body having a firing mechanism configured to be selectively manipulated by an operator, a shaft assembly extending distally from the body, and an end effector extending distally from the shaft assembly and configured to receive a cartridge for manipulating the tissue of the patient, wherein the end effector has a distal end portion, a proximal end portion, a gap between the distal and proximal end portions, and a guide pin extending from the distal end portion to the proximal end portion, wherein the guide pin is configured to receive the tissue thereagainst for positioning the tissue within the gap, wherein the guide pin is connected to each of the distal and proximal end portions to secure the distal end portion relative to the proximal end portion and inhibit deflection of the distal end portion relative to the proximal end portion, the method comprising: (a) receiving the tissue of the patient within the gap between the distal and proximal end portions of the end effector; (b) positioning the tissue against the guide pin; (c) inhibiting deflection of the distal end portion of the end effector relative to the proximal end portion of the end effector with the guide pin; and (d) manipulating the firing mechanism to thereby manipulate the tissue of the patient.

Example 60

The method of Example 59, further comprising increasing tension in the guide pin such that guide pin further inhibits deflection of the distal end portion of the end effector relative to the proximal end portion of the end effector.

Example 61

A surgical instrument comprising: (a) an end effector receiving a cartridge, the cartridge including at least one of a knife and a plurality of staples and configured to actuate from an unfired cartridge position to a fired cartridge position, wherein the knife is configured to cut tissue when actuated from the unfired cartridge position to the fired cartridge position and the plurality of staples are configured to fasten the tissue when actuated from the unfired cartridge position to the fired cartridge position; (b) a shaft assembly connected to the end effector such that the end effector extends distally from the shaft assembly; and (c) a handle assembly connected to the shaft assembly such that the shaft assembly extends distally from the handle assembly, the handle assembly, including: (i) a handle housing, (ii) a firing member configured to selectively actuate from a first position to a second position as a firing stroke, wherein the firing member is operatively connected to the cartridge via the shaft assembly such that the firing member is configured to actuate the cartridge from the unfired cartridge position to the fired cartridge position when the firing member is actuated through the firing stroke, and (iii) a feedback generator operatively connected to the firing member and configured to communicate an audible sound and a visual indicia to an operator indicative of the firing member completing the firing stroke for actuating the cartridge to the fired cartridge position.

Example 62

The surgical instrument of Example 61, wherein the feedback generator further includes: (A) a sound generator mounted within the handle housing and configured to generate the audible sound, and (B) a feedback assembly movably mounted within the handle housing proximate to the sound generator and configured to be driven from an unfired feedback position to a fired feedback position, wherein the feedback assembly includes the visual indicia thereon, and wherein the feedback assembly is configured to strike the sound generator thereby generating the audible sound as the feedback assembly is driven from the unfired feedback position to the fired feedback position via the firing member actuating the firing stroke.

Example 63

The surgical instrument of Example 62, wherein the firing member includes a catch element, wherein the catch element is configured to engage the feedback assembly as the firing member actuates from the first position to the second position and thereby drive the feedback assembly from the unfired feedback position to the fired feedback position.

Example 64

The surgical instrument of any one or more of Examples 62 through 63, wherein the feedback assembly further includes a sled slidably mounted within the handle assembly and configured to be translatably driven from the unfired feedback position to the fired feedback position.

Example 65

The surgical instrument of Example 64, wherein the feedback assembly further includes a linkage coupling pivotally mounted within the handle assembly and pivotally connected to the sled, wherein the linkage coupling is configured to be engaged by the firing member actuating from the first position to the second position and pull the sled from the unfired feedback position to the fired feedback position, wherein a first distance between the unfired feedback position and the fired feedback position is greater than a second distance between the first position and the second position such that the linkage member is configured to magnify movement of the sled for improving resolution of the visual indicia to the operator.

Example 66

The surgical instrument of any one or more of Examples 62 through 65, further wherein the sound generator further comprises a feedback tab configured to be plucked and cause the sound generator to resonate the audible sound, wherein the feedback assembly further comprises a pick, wherein the pick is configured to pluck the feedback tab as the feedback assembly is driven from the unfired feedback position to the fired feedback position.

Example 67

The surgical instrument of any one or more of Examples 62 through 66, further comprising an indicia window extending through the handle housing and aligned with the visual indicia such that the visual indicia is visible through the indicia window.

Example 68

The surgical instrument of Example 67, wherein the visual indicia includes an unfired visual indicia and a fired visual indicia, wherein the unfired visual indicia is configured to align with the indicia window in the unfired feedback position such that the unfired visual indicia is visible through the indicia window and configured to communicate to the operator that the cartridge is in the unfired cartridge position prior to the firing stroke of the firing member, and wherein the fired visual indicia is configured to align with the indicia window in the unfired feedback position such that the unfired visual indicia is visible through the indicia window and configured to communicate to the operator that the cartridge is in the fired cartridge position after the firing stroke of the firing member.

Example 69

The surgical instrument of any one or more of Examples 62 through 68, wherein the sound generator further comprises a feedback tab configured to be plucked and cause the sound generator to resonate the audible sound, wherein the feedback assembly further comprises a pick extending therefrom, wherein the pick is configured to pluck the feedback tab as the feedback assembly is driven from the unfired feedback position to the fired feedback position.

Example 70

The surgical instrument of Example 62, wherein the feedback assembly further includes: (A) a feedback member having the unfired visual indicia and the fired visual indicia thereon and a pick extending therefrom, wherein the pick is configured to strike the sound generator as the feedback assembly is driven from the unfired feedback position to the fired feedback position, and (B) a sled slidably mounted within the handle assembly and configured to be translatably driven from the unfired feedback position to the fired feedback position, and wherein the feedback member is adjustably mounted to the sled assembly such that the position of the feedback member relative to the handle housing is configured to be calibrated to the firing member completing the firing stroke.

Example 71

The surgical instrument of any one or more of Examples 61 through 70, wherein the feedback generator is configured to simultaneously communicate the audible sound and the visual indicia to the operator.

Example 72

The surgical instrument of Example 61, wherein the visual indicia is positioned on the firing member, the surgical instrument further comprising an indicia window extending through the handle housing and aligned with the visual indicia such that the visual indicia is visible through the indicia window.

Example 73

The surgical instrument of Example 61, wherein the feedback generator includes a resilient clip, a ramp, and a drum surface, wherein the resilient clip extends from the firing member and is configured to move with the firing member from an unfired feedback position to a fired feedback position, wherein the ramp is positioned such that the resilient clip is configured to engage the ramp and resiliently bend as the resilient clip moves from the unfired feedback position toward the fired feedback position, and wherein the drum surface is positioned such that the resilient clip is configured to snap from the ramp to the drum surface in the fired position and generate the audible sound therebetween.

Example 74

The surgical instrument of Example 61, the feedback generator having a wheel rotatably mounted within the handle housing, wherein the wheel includes the visual indicia thereon, and wherein the firing member is configured to rotate the firing member from an unfired feedback position to a fired feedback position, the surgical instrument further comprising an indicia window extending through the handle housing and aligned with the visual indicia such that the visual indicia is visible through the indicia window.

Example 75

The surgical instrument of Example 61, further comprising: (a) a first raised bump operatively connected to the firing member; and (b) a second raised bump positioned proximate to the first raised bump, wherein the at first raised bump is configured to grind against the second raised bump and generate the audible sound and a tactile feedback.

Example 76

A surgical instrument comprising: (a) an end effector configured to operatively support a cartridge configured to move from a fired cartridge position to an unfired cartridge position; (b) a shaft assembly connected to the end effector such that the end effector extends distally from the shaft assembly; and (c) a handle assembly connected to the shaft assembly such that the shaft assembly extends distally from the handle assembly, the handle assembly, including: (i) a handle housing, (ii) a firing member configured to selectively actuate from a first position to a second position as a firing stroke, wherein the firing member is operatively connected to the cartridge via the shaft assembly such that the firing member is configured to actuate the cartridge from the unfired cartridge position to the fired cartridge position, and (iii) a feedback generator operatively connected to the firing member and configured to communicate an audible sound and a visual indicia to an operator indicative of the firing member completing the firing stroke for actuating the cartridge to the fired cartridge position.

Example 77

The surgical instrument of Example 76, wherein the feedback generator further includes: (A) a sound generator mounted within the handle housing and configured to generate the audible sound, and (B) a feedback assembly movably mounted within the handle housing proximate to the sound generator and configured to be driven from an unfired feedback position to a fired feedback position, wherein the feedback assembly includes the visual indicia thereon, and wherein the feedback assembly is configured to strike the sound generator thereby generating the audible sound as the feedback assembly is driven from the unfired feedback position to the fired feedback position via the firing member actuating the firing stroke.

Example 78

The surgical instrument of Example 77, wherein the sound generator comprises a feedback tab configured to be plucked and cause the sound generator to resonate the audible sound, wherein the feedback assembly comprises a pick extending therefrom, wherein the pick is configured to pluck the feedback tab as the feedback assembly is driven from the unfired feedback position to the fired feedback position.

Example 79

The surgical instrument of any one or more of Examples 77 through 78, further comprising an indicia window extending through the handle housing and aligned with the visual indicia such that the visual indicia is visible through the indicia window.

Example 80

A method of indicating that a cartridge of a surgical stapling instrument has been fired from an unfired position to a fired position, the method comprising: (a) selectively actuating a firing member a firing stroke from a first position to a second position; (b) actuating a cartridge from an unfired cartridge position to a fired cartridge position via selective actuation of the firing member to the second position; (c) simultaneously generating an audible sound and a visual indicia when the firing member completes the firing stroke to indicate firing of the cartridge to the fired position; and (d) at least one of severing tissue of a patient or fastening the tissue of the patient upon firing the cartridge to the fired position.

Example 81

A surgical instrument comprising: (a) a body having a firing mechanism configured to be selectively manipulated by an operator; (b) a shaft assembly extending distally from the body; (c) an end effector extending distally from the shaft assembly, the end effector including an anvil; and (d) a cartridge received within the end effector opposite the anvil and operatively connected to the firing mechanism, the cartridge including: (i) a cartridge housing having a plurality of staple slots, (ii) a plurality of staples respectively positioned within the plurality of staple slots, and (iii) a driver assembly having a plurality of drivers respectively supporting the plurality of staples thereon within the plurality of staple slots, wherein the firing mechanism is configured to selectively move the plurality of drivers distally toward the anvil for forming the plurality of staples therebetween, wherein at least one driver of the plurality of drivers has a variable distal height relative to at least another driver of the plurality of drivers in a predetermined variable height pattern.

Example 82

The surgical instrument of Example 81, wherein the predetermined variable height pattern of the plurality of drivers is configured to uniformly form the plurality of staples between the anvil and the driver assembly thereby accommodating deflection of the end effector.

Example 83

The surgical instrument of Example 81, wherein the predetermined variable height pattern of the plurality of drivers is configured to non-uniformly form the plurality of staples between the anvil and the driver assembly.

Example 84

The surgical instrument of any one or more of Examples 81 through 83, wherein the plurality of drivers includes a first row of drivers and a second row of drivers arranged in the predetermined variable height pattern, and wherein predetermined variable height pattern tapers down from the second row of drivers toward the first row of drivers.

Example 85

The surgical instrument of Example 84, wherein the first row of drivers has a first uniform distal height, wherein the second row of drivers has a second uniform distal height, and wherein the first uniform distal height is less than the second uniform distal height.

Example 86

The surgical instrument of Example 84, wherein the driver assembly has a knife slot configured to receive a knife therethrough, and the first and second rows of drivers are arranged on one side of the knife slot, wherein the plurality of drivers includes a third row of drivers and a fourth row of drivers arranged in the predetermined variable height pattern on another side of the knife slot, wherein the predetermined variable height pattern tapers down from the fourth row of drivers toward the third row of drivers.

Example 87

The surgical instrument of Example 86, wherein the first row of drivers has a first uniform distal height, wherein the second row of drivers has a second uniform distal height, wherein the first uniform distal height is less than the second uniform distal height, wherein the third row of drivers has a third uniform distal height, the fourth row of drivers has a fourth uniform distal height, and wherein the third uniform distal height is less than the fourth uniform distal height.

Example 88

The surgical instrument of Example 87, wherein the second uniform distal height is less than the third uniform distal height.

Example 89

The surgical instrument of any one or more of Examples 81 through 83, wherein the plurality of drivers includes a first row of drivers arranged in the predetermined variable height pattern from a first end to a second end and a middle therebetween, wherein the predetermined variable height pattern tapers down from the respective first and second ends toward the middle.

Example 90

The surgical instrument of Example 89, wherein the plurality of drivers includes a second row of drivers arranged in the predetermined variable height pattern from the first end to the second end and the middle therebetween, wherein the predetermined variable height pattern tapers down from the second row of drivers toward the first row of drivers.

Example 91

The surgical instrument of Example 90, wherein the driver assembly has a knife slot configured to receive a knife therethrough and the first and second rows of drivers are arranged on one side of the knife slot, wherein the plurality of drivers includes a third row of drivers and a fourth row of drivers arranged in the predetermined variable height pattern on another side of the knife slot from the first end to the second end and the middle therebetween, and wherein the predetermined variable height pattern tapers down from the fourth row of drivers toward the third row of drivers.

Example 92

The surgical instrument of any one or more of Examples 81 through 83, wherein the plurality of drivers includes a first row of drivers arranged in the predetermined variable height pattern from a first end to a second end and a middle therebetween, wherein the predetermined variable height pattern of the first row of drivers tapers down from the respective first end toward the middle and is generally uniform from the middle toward the second end.

Example 93

The surgical instrument of Example 92, wherein the plurality of drivers includes a second row of drivers arranged in the predetermined variable height pattern from the first end to the second end and a middle therebetween, and wherein the predetermined variable height pattern of the second row of drivers tapers down from the first end toward the middle and is generally uniform from the middle toward the second end.

Example 94

The surgical instrument of Example 93, wherein the first and second rows of drivers are identical.

Example 95

The surgical instrument of any one or more of Examples 93 through 94, wherein the driver assembly has a knife slot configured to receive a knife therethrough and the first and second rows of drivers are arranged on one side of the knife slot, wherein the plurality of drivers includes a third row of drivers and a fourth row of drivers arranged in the predetermined variable height pattern on another side of the knife slot from the first end to the second end and the middle therebetween, and wherein the predetermined variable height pattern of the third and fourth rows of drivers tapers down from the respective first end toward the middle and is generally uniform from the middle toward the second end.

Example 96

The surgical instrument of Example 95, wherein the first, second, third, and fourth rows of drivers are identical.

Example 97

A cartridge received in a surgical instrument, the cartridge comprising: (a) a cartridge housing having a plurality of staple slots; (b) a plurality of staples respectively positioned within the plurality of staple slots; and (c) a driver assembly having a plurality of drivers respectively supporting the plurality of staples thereon within the plurality of staple slots, wherein at least one driver of the plurality of drivers has a variable distal height relative to at least another driver of the plurality of drivers in a predetermined variable height pattern.

Example 98

A method of forming a plurality of staples in a tissue of a patient with a surgical instrument, the surgical instrument including a body have a firing mechanism configured to be selectively manipulated by an operator, a shaft assembly extending distally from the body, and a cartridge received within the end effector opposite the anvil and operatively connected to the firing mechanism, the cartridge having a cartridge housing with a plurality of staple slots, a plurality of staples respectively position within the plurality of staple slots, and a driver assembly with a plurality of drivers respectively supporting the plurality of staples thereon within the plurality of staple slots, wherein the firing mechanism is configured to selectively move the plurality of drivers distally toward the anvil for forming the staples therebetween, wherein at least one driver of the plurality of drivers has a variable distal height relative to at least another driver of the plurality of drivers in a predetermined variable height pattern, the method comprising: (a) selectively manipulating the firing mechanism and directing the plurality of drivers with the respective plurality of staples toward the anvil in the predetermined variable height pattern; (b) pressing the plurality of staples between the driver assembly and anvil; and (c) forming the plurality of staples within the tissue of the patient and thereby fluidly sealing the tissue along the formed plurality of staples therewith.

Example 99

The method of Example 98, further comprising deflecting a portion of the end effector with the anvil relative to the plurality of drivers a predetermined deflection such that the predetermined variable height pattern accommodates the predetermined deflection, and wherein forming the plurality of staples further includes uniformly forming the plurality of staples within the tissue.

Example 100

The method of Example 98, wherein forming the plurality of staples further includes non-uniformly forming the plurality of staples within the tissue.

Example 101

A surgical instrument comprising: (a) a body having a firing mechanism configured to be manipulated by an operator; (b) a shaft assembly extending distally from the body; and (c) an end effector operatively connected to the firing mechanism via the shaft assembly, wherein the end effector is configured to receive a cartridge selectively actuated by the selective manipulation of the firing mechanism, wherein a distal end portion of the end effector includes: (i) a first end; (ii) a second end laterally opposite from the first end; (iii) a distal crest laterally positioned between the first and second ends, wherein the distal crest projects distally beyond the first and second ends; and (iv) an arcuate distal surface extending along the distal crest and laterally between the first and second ends, wherein the arcuate distal surface at the distal crest has a radius of curvature configured to be received against a pelvic bowl of a patient to position the end effector relative to colon tissue of the patient for manipulating the colon tissue with the cartridge.

Example 102

The surgical instrument of Example 101, wherein the distal crest projects distally from the first and second ends with the radius of curvature being between approximately 1.5 inches and approximately 3 inches for being received against the pelvic bowl.

Example 103

The surgical instrument of any one or more of Examples 101 through 102, wherein the distal crest projects distally from each of the first and second ends with the radius of curvature is approximately 2 inches for being received against the pelvic bowl.

Example 104

The surgical instrument of any one or more of Examples 101 through 103, wherein the radius of curvature along the arcuate distal surface from the first end to the second end varies with a compound curvature that includes the radius of curvature of the distal crest of approximately 2 inches for being received against the pelvic bowl.

Example 105

The surgical instrument of any one or more of Examples 101 through 104, wherein the distal crest is positioned laterally approximately midway between the first and second ends.

Example 106

The surgical instrument of any one or more of Examples 101 through 105, wherein radius of curvature of the arcuate distal surface extends laterally from the first end to the second end.

Example 107

The surgical instrument of any one or more of Examples 101 through 106, wherein the first end is in the form of a first half-dome extending to the distal arcuate surface, wherein the second end is in the form of a second half-dome extending to the distal arcuate surface.

Example 108

The surgical instrument of Example 107, wherein the first and second half-domes have the radius of curvature.

Example 109

The surgical instrument of any one or more of Examples 101 through 108, wherein the distal end portion of the end effector is laterally C-shaped from the first end to the second end.

Example 110

The surgical instrument of Example 109, wherein the C-shaped distal end portion of the end effector has an inner radius of curvature of between approximately 1.0 inch and 1.2 inches and an outer radius of curvature of between approximately 1.3 inches and approximately 1.6 inches.

Example 111

The surgical instrument of Example 110, wherein the inner radius curvature is approximately 1.1 inches and the outer radius of curvature is approximately 1.5 inches.

Example 112

The surgical instrument of any one or more of Examples 101 through 111, wherein the distal arcuate surface extends continuously from the first end to the second end.

Example 113

The surgical instrument of Example 112, wherein the distal arcuate surface extends smoothly from the first end to the second end.

Example 114

The surgical instrument of any one or more of Examples 101 through 113, further comprising a cartridge configured to be received within the end effector, wherein the cartridge includes at least one of a knife or a plurality of staples, wherein the knife is configured to sever tissue, and wherein the plurality of staples are configured to fasten tissue.

Example 115

The surgical instrument of Example 114, wherein the distal end portion of the end effector is laterally C-shaped from the first end to the second end.

Example 116

The surgical instrument of any one or more of Examples 114 through 115, wherein the distal crest is positioned laterally midway between the first and second ends.

Example 117

The surgical instrument of any one or more of Examples 114 through 116, wherein the distal arcuate surface extends continuously from the first end to the second end.

Example 118

The surgical instrument of any one or more of Examples 114 through 117, wherein radius of curvature of the arcuate distal surface extends laterally from the first end to the second end.

Example 119

The surgical instrument of any one or more of Examples 114 through 118, wherein the first end is a first half-dome extending to the distal arcuate surface, and the second end is a second half-dome extending to the distal arcuate surface.

Example 120

A method of manipulating colon tissue of a patient with a surgical instrument, the surgical instrument including a body having a firing mechanism configured to be manipulated by an operator, a shaft assembly extending distally from the body, and an end effector operatively connected to the firing mechanism via the shaft assembly, wherein the end effector is configured to receive a cartridge selectively actuated by the selective manipulation of the firing mechanism, wherein the distal end portion of the end effector includes a first end, a second end laterally opposite from the first end, a distal crest, and an arcuate distal surface, the distal crest laterally positioned between the first and second ends, wherein the distal crest projects distally beyond the first and second ends, wherein the arcuate distal surface extends along the distal crest and laterally between the first and second ends, and wherein the arcuate distal surface at the distal crest has a radius of curvature configured to be received against a pelvic bowl of the patient to position the end effector relative to the colon tissue of the patient for manipulating the colon tissue with the cartridge, the method comprising: (a) inserting the end effector within the pelvic bowl of the patient; (b) positioning the arcuate distal surface of the distal end portion of the end effector against the pelvic bowl such that the end effector is in a predetermined orientation relative to the colon tissue thereby positioning the cartridge relative to the colon tissue, wherein the arcuate distal surface and the distal crest complement a curvature of tissue in the pelvic bowl that the end effector is positioned against; and (c) receiving the colon tissue within the end effector; and (d) actuating the end effector to thereby staple and sever the tissue with the end effector.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

The entire disclosures of: U.S. Pat. No. 5,403,312, entitled "Electrosurgical Hemostatic Device," which issued on Apr. 4, 1995; U.S. Pat. No. 7,000,818, entitled "Surgical Stapling Instrument having Separate Distinct Closing and Firing Systems," which issued on Feb. 21, 2006; U.S. Pat. No. 7,422,139, entitled "Motor-Driven Surgical Cutting and Fastening Instrument with Tactile Position Feedback," which issued on Sep. 9, 2008; U.S. Pat. No. 7,464,849, entitled "Electro-Mechanical Surgical Instrument with Closure System and Anvil Alignment Components," which issued on Dec. 16, 2008; U.S. Pat. No. 7,670,334, entitled "Surgical Instrument Having An Articulating End Effector," which issued on Mar. 2, 2010; U.S. Pat. No. 7,753,245, entitled "Surgical Stapling Instruments," which issued on Jul. 13, 2010 U.S. Pat. No. 8,393,514, entitled "Selectively Orientable Implantable Fastener Cartridge," which issued on Mar. 12, 2013 U.S. patent application Ser. No. 11/343,803, entitled "Surgical Instrument Having Recording Capabilities;" now U.S. Pat. No. 7,845,537; U.S. patent application Ser. No. 12/031,573, entitled "Surgical Cutting And Fastening Instrument Having RF Electrodes," filed Feb. 14, 2008; U.S. patent application Ser. No. 12/031,873, entitled "End Effectors For A Surgical Cutting And Stapling Instrument," filed Feb. 15, 2008, now U.S. Pat. No. 7,980,443; U.S. patent application Ser. No. 12/235,782, entitled "Motor-Driven Surgical Cutting Instrument," now U.S. Pat. No. 8,210,411; U.S. patent application Ser. No. 12/249,117, entitled "Powered Surgical Cutting And Stapling Apparatus With Manually Retractable Firing System," now U.S. Pat. No. 8,608,045; U.S. patent application Ser. No. 12/647,100, entitled "Motor-Driven Surgical Cutting Instrument with Electric Actuator Directional Control Assembly," filed Dec. 24, 2009; now U.S. Pat. No. 8,220,688; U.S. patent application Ser. No. 12/893,461, entitled "Staple Cartridge," filed Sep. 29, 2012, now U.S. Pat. No. 8,733,613; U.S. patent application Ser. No. 13/036,647, entitled "Surgical Stapling Instrument," filed Feb. 28, 2011, now U.S. Pat. No. 8,561,870; U.S. patent application Ser. No. 13/118,241, entitled "Surgical Stapling Instruments With Rotatable Staple Deployment Arrangements," now U.S. Pat. No. 9,072,535; U.S. patent application Ser. No. 13/524,049, entitled "Articulatable Surgical Instrument Comprising A Firing Drive," filed on Jun. 15, 2012; now U.S. Pat. No. 9,101,358; U.S. patent application Ser. No. 13/800,025, entitled "Staple Cartridge Tissue Thickness Sensor System," filed on Mar. 13, 2013, now U.S. Pat. No. 9,345,481; U.S. patent application Ser. No. 13/800,067, entitled "Staple Cartridge Tissue Thickness Sensor System," filed on Mar. 13, 2013, now U.S. Patent Application Publication No. 2014/0263552; U.S. Patent Application Publication No. 2007/0175955, entitled "Surgical Cutting And Fastening Instrument With Closure Trigger Locking Mechanism," filed Jan. 31, 2006; and U.S. Patent Application Publication No. 2010/0264194, entitled "Surgical Stapling Instrument With An Articulatable End Effector," filed Apr. 22, 2010, now U.S. Pat. No. 8,308,040, are hereby incorporated by reference herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using an instrument to manipulate tissue of a patient, wherein the instrument has an end effector, the method comprising:
   (a) positioning the tissue within a gap between a cartridge and an anvil of the end effector, wherein the cartridge includes a knife and a plurality of staples, wherein the anvil is located in a distal end portion of the end effector, and wherein the end effector is in an open configuration during the act of positioning the tissue between the anvil and the cartridge;
   (b) positioning the tissue against a guide pin to laterally position the tissue relative to the cartridge and the anvil;
   (c) moving a retaining pin from an open position toward a closed position across the gap, thereby capturing the tissue between the cartridge, the anvil, the guide pin, and the retaining pin;
   (d) moving the cartridge toward the anvil such that the end effector is in a closed configuration;
   (e) inhibiting deflection of the distal end portion of the end effector for aligning the cartridge and the anvil, wherein at least one of the guide pin or the retaining pin connects to the distal end portion secure the distal end portion relative to a proximal end portion of the end effector to thereby inhibit deflection of the distal end portion of the end effector;
   (f) forming the plurality of staples within the tissue and fluidly sealing the tissue;
   (g) sliding the knife distally toward the tissue such that the knife directs the retaining pin to lock to the distal end portion in a locked closed position; and
   (h) cutting the tissue with the knife, thereby severing the tissue.

2. The method of claim 1, wherein inhibiting deflection is provided by the guide pin connected to the distal end portion and the proximal end portion to secure the distal end portion relative to the proximal end portion of the end effector.

3. The method of claim 2, further comprising increasing tension in the guide pin such that guide pin further inhibits deflection of the distal end portion of the end effector relative to the proximal end portion of the end effector.

4. The method of claim 1, wherein inhibiting deflection is provided by the retaining pin connected to the distal end portion and the proximal end portion to secure the distal end portion relative to the proximal end portion of the end effector.

5. The method of claim 4, wherein the distal end portion includes a first ledge, the retaining pin includes a second ledge, and the method further comprises overlapping the second ledge with the first ledge to lock the retaining pin in the locked closed position.

6. The method of claim 5, wherein locking the retaining pin further includes expanding a portion of the retaining pin within the distal end portion of the end effector.

7. The method of claim 6, wherein expanding a portion of the retaining pin further includes sliding the knife toward the anvil such that the knife forces the portion of the retaining pin to expand.

8. The method of claim 6, wherein expanding a portion of the retaining pin further includes sliding a closure rod through the retaining pin toward the distal end portion such that the closure rod forces the portion of the retaining pin to expand.

9. The method of claim 5, wherein the end effector includes a cam mechanism having a cam tab and a cam slot, and the method further comprises guiding the cam tab through the cam slot and rotating the retaining pin therewith to the locked closed position.

10. The method of claim 9, wherein the guide pin is rotatably supported in a support cradle, and the method further comprises translating the support cradle and the retaining pin toward the distal end portion.

11. The method of claim 4, wherein the distal end portion includes a first plurality of threads, the retaining pin includes a second plurality of threads, and the method further comprises threading the second plurality of threads with the first plurality of threads to lock the retaining pin in the locked closed position.

12. The method of claim 11, wherein the end effector includes a cam mechanism having a cam tab and a spiral cam slot, and the method further comprises guiding the cam tab through the spiral cam slot and rotating the retaining pin therewith to the locked closed position.

13. The method of claim 1, wherein the end effector is operatively attached to a body having a firing member configured to selectively actuate a firing stroke and move the cartridge from an unfired cartridge position to a fired cartridge position for forming the plurality of staples and cutting the tissue, wherein the method further comprises simultaneously communicating an audible sound and a visual indicia with a feedback generator to the operator to indicate that the firing member completed the firing stroke for actuating the cartridge to the fired cartridge position.

14. The method of claim 1, wherein the tissue is a colon tissue, and the method further comprises performing a lower anterior resection of the colon tissue.

15. The method of claim 14, wherein the distal end portion of the end effector includes, a first end, a second end laterally opposite from the first end, a distal crest laterally positioned between the first and second ends, wherein the distal crest projects distally beyond the first and second ends; and an arcuate distal surface extending along the distal crest and laterally between the first and second ends, wherein the arcuate distal surface at the distal crest has a radius of curvature configured to be received against a pelvic bowl of the patient to position the end effector relative to the colon tissue of the patient for manipulating the colon tissue with the cartridge, wherein the method further comprises positioning the arcuate distal surface of the distal end portion of the end effector against the pelvic bowl such that the end effector is in a predetermined orientation relative to the colon tissue thereby positioning the cartridge relative to the colon tissue for performing the lower anterior resection of the colon tissue.

16. The method of claim 1, wherein the distal end portion of the end effector has a distal arcuate continuous surface.

17. A method of using an instrument to manipulate tissue of a patient, wherein the instrument has an end effector, the method comprising:
   (a) positioning the tissue within a gap between a cartridge and an anvil of the end effector, wherein the cartridge includes a knife and a plurality of staples, wherein the anvil is located in a distal end portion of the end effector, and wherein the end effector is in an open configuration during the act of positioning the tissue between the anvil and the cartridge;

(b) positioning the tissue against a guide pin to laterally position the tissue relative to the cartridge and the anvil;

(c) moving a retaining pin from an open position toward a closed position across the gap, thereby capturing the tissue between the cartridge, the anvil, the guide pin, and the retaining pin;

(d) moving the cartridge toward the anvil such that the end effector is in a closed configuration;

(e) inhibiting deflection of the distal end portion of the end effector for aligning the cartridge and the anvil, wherein at least one of the guide pin or the retaining pin connects to the distal end portion to secure the distal end portion relative to a proximal end portion of the end effector to thereby inhibit deflection of the distal end portion of the end effector;

(f) forming the plurality of staples within the tissue and fluidly sealing the tissue; and (g) cutting the tissue with the knife, thereby severing the tissue, wherein the cartridge includes a driver assembly and a plurality of staple slots, wherein the driver assembly has a plurality of drivers respectively supporting the plurality of staples thereon within the plurality of staple slots, wherein at least one driver of the plurality of drivers has a variable distal height relative to at least another driver of the plurality of drivers in a predetermined variable height pattern, and the method further comprises directing the plurality of drivers with the respective plurality of staples toward the anvil in the predetermined variable height pattern.

18. The method of claim 17, further comprising deflecting the distal end portion of end effector with the anvil relative to the plurality of drivers a predetermined deflection such that the predetermined variable height pattern accommodates the predetermined deflection, and wherein forming the plurality of staples further includes uniformly forming the plurality of staples within the tissue.

19. The method of claim 17, wherein forming the plurality of staples further includes non-uniformly forming the plurality of staples within the tissue.

20. A method of using an instrument to manipulate colon tissue of a patient, wherein the instrument has an end effector with a distal end portion having a distal arcuate continuous surface, the method comprising:

(a) engaging the distal arcuate continuous surface of the distal end portion against a pelvic bowl to stabilize the end effector within the pelvic bowl and align the end effector relative to the colon tissue in a predetermined orientation;

(b) positioning the colon tissue within a gap between a cartridge and an anvil of an end effector, wherein the cartridge includes a knife and a plurality of staples, wherein the anvil is received within the distal end portion of the end effector, and wherein the end effector is in an open configuration during the act of positioning the colon tissue between the anvil and the cartridge;

(c) positioning the colon tissue against a guide pin, (d) moving a retaining pin from an open position toward a closed position across the gap, thereby capturing the colon tissue between the cartridge, the anvil, the guide pin, and the retaining pin;

(e) moving the cartridge toward the anvil such that the end effector is in a closed configuration;

(f) inhibiting deflection of the distal end portion of the end effector for aligning the cartridge and the anvil, wherein at least one of the guide pin and the retaining pin connects to the distal end portion to secure the distal end portion relative to a proximal end portion of the end effector;

(g) forming the plurality of staples within the colon tissue and fluidly sealing the colon tissue; and (h) cutting the colon tissue with the knife, thereby providing a lower anterior resection of the colon tissue.

* * * * *